US011643429B2

(12) United States Patent
Holmes et al.

(10) Patent No.: US 11,643,429 B2
(45) Date of Patent: May 9, 2023

(54) COMPOUNDS AND METHODS FOR THE TREATMENT OF OCULAR DISORDERS

(71) Applicant: Azura Ophthalmics Ltd., Tel Aviv (IL)

(72) Inventors: Ian Holmes, Victoria (AU); Yair Alster, Tel Aviv (IL); Hila Barash, Shoham (IL); Charles Bosworth, Las Vegas, NV (US); Omer Rafaeli, Udim (IL); Marc Gleeson, Longueville (AU); Mark Richard Stewart, Cambridge (GB); Jonathan Dunn, Cambridge (GB)

(73) Assignee: AZURA OPHTHALMICS LTD., Tel Aviv (IL)

( * ) Notice: Subject to any disclaimer, the term of this patent is extended or adjusted under 35 U.S.C. 154(b) by 0 days.

(21) Appl. No.: 17/222,821

(22) Filed: Apr. 5, 2021

(65) Prior Publication Data

US 2021/0230205 A1    Jul. 29, 2021

Related U.S. Application Data

(63) Continuation of application No. PCT/IB2020/000312, filed on Apr. 16, 2020.

(60) Provisional application No. 62/966,482, filed on Jan. 27, 2020, provisional application No. 62/835,975, filed on Apr. 18, 2019.

(51) Int. Cl.
*C07H 17/00* (2006.01)
*A61P 27/04* (2006.01)
*A61K 9/00* (2006.01)
*C07H 17/08* (2006.01)

(52) U.S. Cl.
CPC .......... *C07H 17/00* (2013.01); *A61K 9/0048* (2013.01); *A61P 27/04* (2018.01); *C07H 17/08* (2013.01)

(58) Field of Classification Search
CPC .... C07H 17/08; A61K 9/0014; A61K 9/0048; A61K 31/7048; A61P 27/00–14; A61P 17/00–18
See application file for complete search history.

(56) References Cited

U.S. PATENT DOCUMENTS

| | | | |
|---|---|---|---|
| 5,350,839 A * | 9/1994 | Asaka | C07H 17/08 536/7.4 |
| 5,846,514 A | 12/1998 | Foster et al. | |
| 6,239,113 B1 | 5/2001 | Dawson et al. | |
| 6,334,997 B1 | 1/2002 | Foster et al. | |
| 6,569,443 B1 | 5/2003 | Dawson et al. | |
| 7,056,893 B2 | 6/2006 | Roy et al. | |
| 9,463,201 B2 | 10/2016 | Alster et al. | |
| 2003/0064939 A1 | 4/2003 | Sklavounos et al. | |
| 2003/0228299 A1 * | 12/2003 | Droy-Lefaix | A61P 27/14 424/94.4 |
| 2005/0171342 A1 * | 8/2005 | Burnet | A61K 49/0004 536/22.1 |
| 2009/0170791 A1 | 7/2009 | Alihodzic et al. | |
| 2011/0281812 A1 * | 11/2011 | Alihodzic | A61P 9/10 514/29 |
| 2015/0232499 A1 | 8/2015 | Burnet et al. | |
| 2020/0030268 A1 | 1/2020 | Amselem et al. | |
| 2020/0179305 A1 | 6/2020 | Alster et al. | |

FOREIGN PATENT DOCUMENTS

| | | | |
|---|---|---|---|
| CN | 1837225 A * | 9/2006 | |
| WO | WO-9518604 A1 * | 7/1995 | ............ A61K 31/54 |
| WO | WO-03070174 A2 | 8/2003 | |
| WO | WO-2011100769 A2 | 8/2011 | |
| WO | WO-2013003731 A2 | 1/2013 | |
| WO | WO-2018161039 A1 * | 9/2018 | ........... C07C 217/40 |
| WO | WO-2018215638 A1 | 11/2018 | |
| WO | WO-2020212760 A2 | 10/2020 | |

OTHER PUBLICATIONS

Postnikoff, C. et al "Leukocyte distribution in the open eye tears . . . " Curr. Eye Res., voll 43, No. 10, pp. 1253-1259. (Year: 2018).*
Ulrich, C. et al "Treatment of multiple actinic keratoses with topical diclofenac . . . " Br. J. Dermatol., vol. 156, suppl. 3, pp. 40-42. (Year : 2007).*
CN 1837225A machine translation. (Year: 2006).*
Alikhan, A. et al "Keratolytic Treatment" in Pathogenesis and Treatment of Acne and Rosacea, C. Zouboulis etal (eds.), Springer-Verlag, Berlin, pp. 397-414. (Year: 2014).*
Barabino et al. Animal Models of Dry Eye: A Critical Assessment of Opportunities and Limitations. Invest. Ophthalmol. Vis. Sci. 45:1641-1646 (2004).
Barabino et al. The Controlled-Environment Chamber: A New Mouse Model of Dry Eye. Invest. Ophthalmol. Vis. Sci. 46:2766-2771 (2005).
Berge et al. Pharmaceutical Salts. Journal of Pharmaceutical Sciences 66(1):1-19 (Jan. 1977).
Dursun et al. A Mouse Model of Keratoconjunctivitis Sicca. Invest. Ophthalmol. Vis. Sci. 43:632-638 (2002).
Evans. Synthesis of radiolabeled compounds. J Radioanal Chem 64(1-2):9-32 (1981).
Kabalka et al. The Synthesis of Radiolabeled Compounds via Organometallic Intermediates. Tetrahedron 45(21):6601-6621 (1989).

(Continued)

*Primary Examiner* — Leigh C Maier
(74) *Attorney, Agent, or Firm* — Wilson Sonsini Goodrich & Rosati

(57) ABSTRACT

Described herein are compositions and methods for the treatment of ocular surface disorders including meibomian gland dysfunction, blepharitis, dry eye disease and other inflammatory/infections disease of the anterior surface of the eye. Said compositions and methods comprise keratolytic conjugate which demonstrate keratolytic activity, and anti-inflammatory or other desirable activities. Topical administration of said compositions to the eye, ocular surface or surrounding areas provides therapeutic benefit to patients suffering from ocular surface disorders.

20 Claims, No Drawings

(56) References Cited

OTHER PUBLICATIONS

Knop et al. The International Workshop on Meibomian Gland Dysfunction: Report of the Subcommittee on Anatomy, Physiology, and Pathophysiology of the Meibomian Gland. IOVS 52(4):1938-1978 (2011).

Nichols et al. The International Workshop on Meibomian Gland Dysfunction: Executive Summary. Invest. Ophthalmol. Vis. Sci. 52(4):1922-1929 (2011).

Niederkorn et al. Desiccating Stress Induces T Cell-Mediated Sjogren's Syndrome-like Lacrimal Keratoconjunctivitis. J. Immunol. 176:3950-3957 (2006).

PCT/IB2020/000312 International Invitation to Pay Additional Fees dated Oct. 29, 2020.

PCT/IB2020/000312 International Search Report and Written Opinion dated Jan. 15, 2021.

Pflugfelder et al. A Randomized, Double-Masked, Placebo-Controlled, Multicenter Comparison of Loteprednol Etabonate Ophthalmic Suspension, 0.5%, and Placebo for Treatment of Keratoconjunctivitis Sicca in Patients With Delayed Tear Clearance. Am J Ophthalmol 138:444-57 (2004).

Pflugfelder et al. International Dry Eye Workshop, 2007. Management and Therapy of Dry Eye Disease: Report of the Management and Therapy Subcommittee of the International Dry Eye Workshop. Ocul Surf 5:163-178 (2007).

Schaumberg et al. The International Workshop on Meibomian Gland Dysfunction: Report of the Subcommittee on the Epidemiology of, and Associated Risk Factors for, MGD. Invest. Ophthalmol. Vis. Sci. 52(4):1994-2005 (2011).

Qiao et al. Emerging treatment options for meibomian gland dysfunction. Clinical Ophthalmology 7:1797-1803 (2013).

* cited by examiner

COMPOUNDS AND METHODS FOR THE TREATMENT OF OCULAR DISORDERS

CROSS-REFERENCE TO RELATED APPLICATIONS

This application is the continuation application of International Application No. PCT/IB2020/000312, filed Apr. 16, 2020, and claims the benefit of U.S. Provisional Application No. 62/835,975, filed Apr. 18, 2019, and 62/966,482, filed Jan. 27, 2020, all of which are incorporated herein by reference in their entireties.

BACKGROUND OF THE INVENTION

Restasis (0.05% cyclosporine A, Allergan) was approved by the Food and Drug Administration (FDA) to increase tear production in patients whose tear production is presumed to be suppressed due to ocular inflammation associated with keratoconjunctivitis sicca. Xiidra® (lifitegrast ophthalmic solution) 5% is indicated for the treatment of signs and symptoms of dry eye disease (DED).

SUMMARY OF THE INVENTION

Provided in certain embodiments herein are compounds, pharmaceutical (e.g., ophthalmic) compositions, and methods of treatment. In specific embodiments, methods of treatment provided herein include the treatment of ocular and/or periocular indications or abnormalities. In some embodiments, the ocular and/or periocular indications or abnormalities treated by or with a composition or compound provided herein are indications or abnormalities that have multifactorial etiologies and/or interactions. In certain embodiments provided herein are compounds (and compositions comprising such compounds) that have multifunctional efficacies, such as when administered in or around the eye (e.g., to the ocular surface, the eyelid, such as the eyelid margin or the inner surface of the eyelid, or the like).

In certain embodiments, methods provided herein involve the method of treating meibomian gland dysfunction (MGD). Currently there are no approved pharmacological agents useful for the treatment of MGD The recognition that terminal duct obstruction from hyperkeratinization of the ductal epithelium on meibomian glands is a core mechanism behind meibomian gland dysfunction (MGD) is consistent with clinical experience demonstrating that effective treatments for MGD require resolution of ductal obstruction and evacuation of glandular contents (Nichols et al, 2011; Lane et al, 2012; Blackie et al, 2015). Warm compresses and thermal/mechanical devises (e.g., LipiFlow) are used in an attempt to raise the internal temperature of the meibomian glands over the normal melting point for meibum (i.e., 32° C. to 40° C.) in an attempt to resolve terminal duct obstruction (Lane et al, 2012). Unfortunately, warm compresses are unable to achieve this benefit for severely obstructed glands which can having a melting point >40° C. Current technology for removing keratinized obstruction of the meibomian gland also includes physical removal methods (e.g., debridement and gland probing), which are quite painful to patients.

Subsequent to a period of MGD, various stages of inflammatory or bacterial disease at the ocular surface are frequently observed because meibomian gland obstruction can cause a cascade of events that include further deterioration of the glands (Knop, IOVS, 2011) from stasis of the meibum in the secretory glands, mechanical pressure and stress from glandular obstruction, and increased bacterial growth that is associated with the downstream release of bacterial lipases, toxic mediators, and/or inflammatory mediators. All these factors reduce the quality and/or quantity of meibum the glands can release which in turn can cause chronic mechanical traumatization of the conjunctival, corneal and eyelid tissues which will lead to further tissue damage and the release of inflammatory mediators. Thus, many patients suffering from MGD also have inflammatory disease affecting their conjunctiva, cornea, larcrimal gland, lids or goblet cells causing comorbid conditions such as dry eye syndrome or blepharitis for which there is an unmet medical need.

For example, literature has used the terms posterior blepharitis and MGD as if they were synonymous, but these terms are not interchangeable. Posterior blepharitis describes inflammatory conditions of the posterior lid margin, of which MGD is only one possible cause. In its earliest stages, MGD may not be associated with clinical signs characteristic of posterior blepharitis. At this stage, affected individuals may be symptomatic, but alternatively, they may be asymptomatic, and the condition regarded as subclinical. As MGD progresses, symptoms develop and lid margin signs, such as changes in meibum expressibility and quality and lid margin redness, may become more visible. At this point, an MGD-related posterior blepharitis is said to be present.

In certain embodiments, provided herein are methods of treating ocular (or dermatological) disorders associated with keratosis (e.g., lid keratosis, surface ocular keratosis, and/or gland blockage—such as in MGD), microbial infiltration/infection (e.g., bacterial infiltration/infection), and/or inflammation (such as inflammation associated keratosis or not associated with keratosis). In certain instances, disorders of the skin and/or eye (and/or surround tissue/skin) are difficult to differentially diagnose and/or have multiple etiologies. For example, in some instances, it can be difficult to distinguish between ocular disorders that involve (1) inflammation only, (2) inflammation associated with keratolytic activity, (3) inflammation associated with both keratolytic activity (e.g., inducing keratosis) and microbial infiltration, (4) keratolytic activity, but not inflammation and/or microbial infiltration, or various other combinations. In some instances, compounds and compositions provided herein can be used in such ocular and/or dermatological indications without the need for differential diagnosis (which can be difficult, e.g., because of similar symptom scores, etc.). Further, many ocular and/or dermatological disorders involve multiple etiologies, such inflammation, microbial infiltration, keratolytic activity, or various combinations thereof. As a result, therapeutic agents, such as those described herein, that target multiple etiologies are beneficial in providing therapeutic efficacy, such as by targeting both an underlying condition (e.g., keratolytic activity and/or microbial infiltration) and a symptom, such as inflammation or dry eye.

Topical azithromycin is anti-inflammatory, inhibiting proinflammatory cytokines, and is potent against gram-negative microorgansims. It is believed to penetrate into the ocular surface where it remains at therapeutic levels days after the therapy has stopped.

As such, provided herein are compounds, compositions and methods and formulations for treating ocular (e.g., periocular) or dermatological disorders, such as those having abnormalities having multifactorial etiologies. In specific embodiments, ocular disorders include, by way of non-limiting example, surface disorders, such as MGD, dry eye and associated inflammatory and bacterial disease.

In certain embodiments, provided herein are compounds having the structure of Formula (Ia):

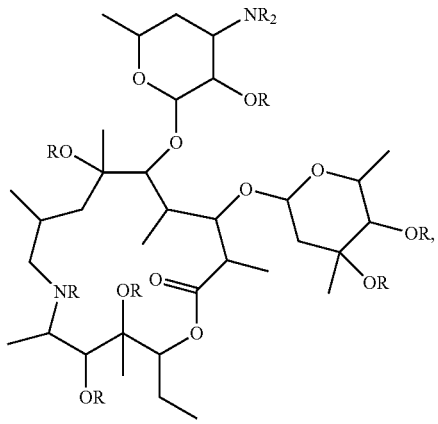

Formula (Ia)

wherein, each R is independently H, R', substituted or unsubstituted alkyl, or substituted or unsubstituted heteroalkyl, wherein at least one R is R';

R' is D-L-;

D is a keratolytic agent (e.g., radical thereof);

L is a linker, or a pharmaceutically acceptable salt or solvate thereof.

In some embodiments, each R is independently H, R', substituted or unsubstituted alkyl, or substituted or unsubstituted heteroalkyl, wherein one R is R'. In some embodiments, each R is independently H, R', substituted alkyl, or unsubstituted alkyl. In specific embodiments, at least one R is R'. In some embodiments, each R is independently H, R', or unsubstituted alkyl, wherein one R is R'. In some embodiments, the unsubstituted alkyl is methyl, ethyl, or propyl. In some embodiments, each R is independently H, R', or unsubstituted heteroalkyl, wherein one R is R'. In some embodiments, the unsubstituted heteroalkyl is selected from the group consisting of (C=O)alkyl, (C=O)Oalkyl, (C=O)Salkyl, (C=O)Sheteroalkyl, or (C=O)amino, wherein the alkyl or amino is optionally substituted. In some embodiments, each R is independently H, methyl, or R', wherein one R is R'.

In some embodiments, alkyl is optionally substituted with one or more selected from the group consisting of —OH, —SH, substituted or unsubstituted alkyl (alkylene), unsubstituted or substituted aryl, substituted or unsubstituted heteroalkyl, —NHCOMe, —O(C=O)CH$_2$OH, —O(C=O)CH(CH$_3$)OH, —O(C=O)alkyl, and —(C=O)Oalkyl (e.g., where alkyl is methyl, ethyl, propyl, isopropyl, or t-butyl). In some embodiments, the alkyl is substituted with one or more selected from the group consisting of alkyl, heterocycloalkyl, —NHCOMe, —O(C=O)alkyl, and —(C=O)Oalkyl (e.g., where alkyl is methyl, ethyl, propyl, isopropyl, or t-butyl). In some embodiments, the heterocycloalkyl is dithiolane.

In some embodiments, R is H, methyl, ethyl, propyl, iso-propyl, t-butyl, —(C=O)alkyl, —(C=O)CH$_2$(OCH$_2$CH$_2$)$_4$OH, —(C=O)CH$_2$CH$_2$(OCH$_2$CH$_2$)$_4$OH,

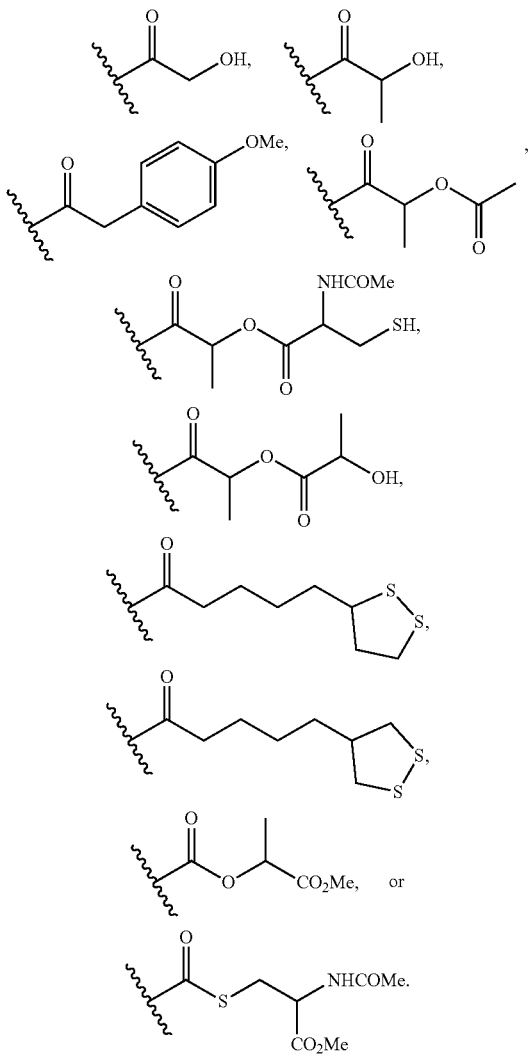

In some embodiments, R' is —(C=O)CH$_2$(OCH$_2$CH$_2$)$_4$OH, —(C=O)CH$_2$CH$_2$(OCH$_2$CH$_2$)$_4$OH,

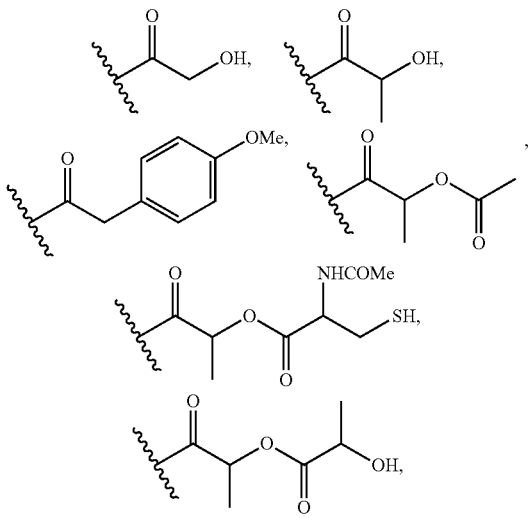

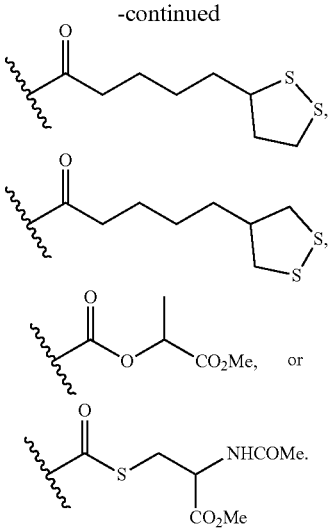

One embodiment provides a compound, having the structure of Formula (Ib):

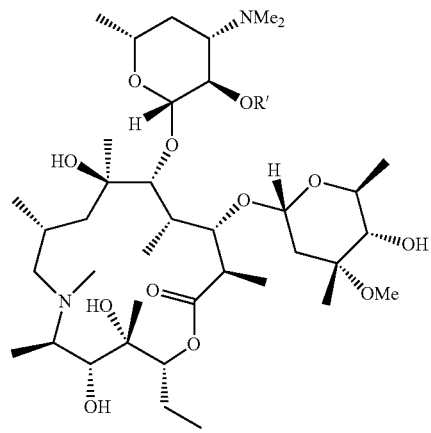

Formula (Ib)

wherein,
R' is D-L-;
D is a keratolytic agent (e.g., radical thereof);
L is a linker,
or a pharmaceutically acceptable salt or solvate thereof.

In some embodiments, L comprises one or more linker groups, each linker group being selected from the group consisting of a bond, —O—, —S—, halo, alkyl (alkylenyl), heteroalkyl (heteroalkylenyl), disulfide, ester, and carbonyl (>C═O). In some embodiments, each linker group is selected from the group consisting of a bond, —O—, —S—, halo, alkyl (alkylenyl), heteroalkyl (heteroalkylenyl), and ester. In some embodiments, each linker group is selected from alkyl (alkylene) and heteroalkyl (heteroalkylene), the alkyl (alkylene) or heteroalkyl (heteroalkylene) being optionally substituted. In some embodiments, L is alkyl (alkylene) substituted with oxo and one or more of alkyl and heteroalkyl. In some embodiments, the alkyl or heteroalkyl is substituted with one or more halo, alkyl, or haloalkyl. In some embodiments, the alkyl or heteroalkyl is substituted with one or more alkyl or haloalkyl. In some embodiments, L is a bond, —O—, —S—, (C═O), —(C═O)alkyl-, —(C═O)heteroalkyl-, —(C═O)O—, —(C═O)Oalkyl-, —(C═O)Oheteroalkyl-, —(C═O)S—, —(C═O)Salkyl-, —(C═O)Sheteroalkyl-, alkylene, or heteroalkylene, where each alkyl, heteroalkyl, alkylene, or heteroalkyl is optionally substituted. In some embodiments, L is (C═O), —(C═O)alkyl-, —(C═O)heteroalkyl-, —(C═O)O—, —(C═O)Oalkyl-, —(C═O)Oheteroalkyl-, —(C═O)S—, —(C═O)Salkyl-, —(C═O)Sheteroalkyl-, alkylene, or heteroalkylene.

In some embodiments, D is selected from alkyl and heteroalkyl, the alkyl or heteroalkyl being optionally substituted. In some embodiments, D is alkyl substituted with oxo and one or more of the group selected from substituted alkyl and substituted heteroalkyl. In some embodiments, the alkyl is substituted with one or more of the group selected from —SH, —OH, substituted or unsubstituted aryl, substituted or unsubstituted heteroalkyl, or substituted or unsubstituted heterocycloalkyl. In some embodiments, D is heteroalkyl substituted with oxo and one or more of the group selected from substituted alkyl and substituted heteroalkyl. In some embodiments, the heteroalkyl is substituted with one or more of the group selected from —SH, —OH, or substituted or unsubstituted heteroalkyl. In some embodiments, the heteroalkyl is substituted with one or more of the group selected from —SH, —OH, alkyl, (C═O)alkyl, (C═O)heteroalkyl, and —NH(C═O)alkyl.

In some embodiments, the compound comprises more than one keratolytic agent. In some embodiments, the keratolytic agent is selected from one or more of the group consisting of —(C═O)CH$_2$(OCH$_2$CH$_2$)$_4$OH, —O(C═O)CH$_2$(OCH$_2$CH$_2$)$_4$OH, —(C═O)CH$_2$CH$_2$(OCH$_2$CH$_2$)$_4$OH, —O(C═O)CH$_2$CH$_2$(OCH$_2$CH$_2$)$_4$OH, —CO$_2$alkyl(e.g., methyl, ethyl, propyl, isopropyl, or t-butyl),

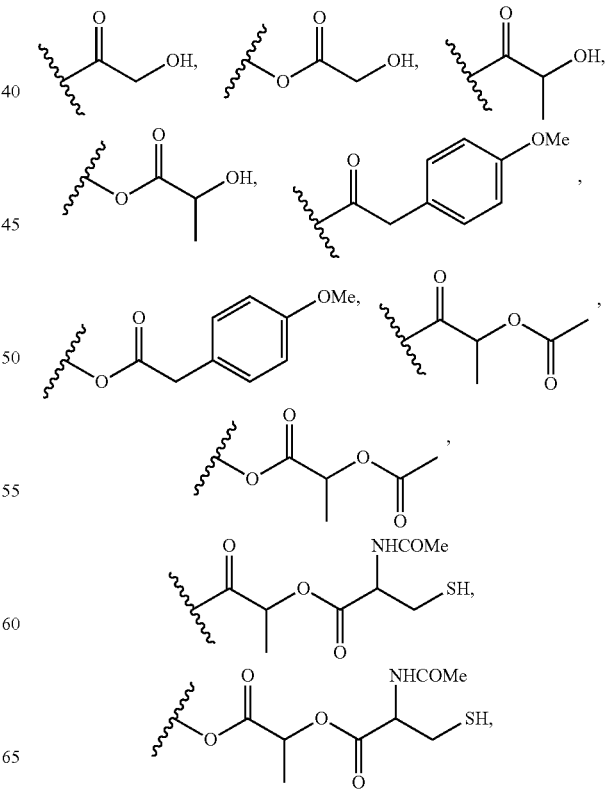

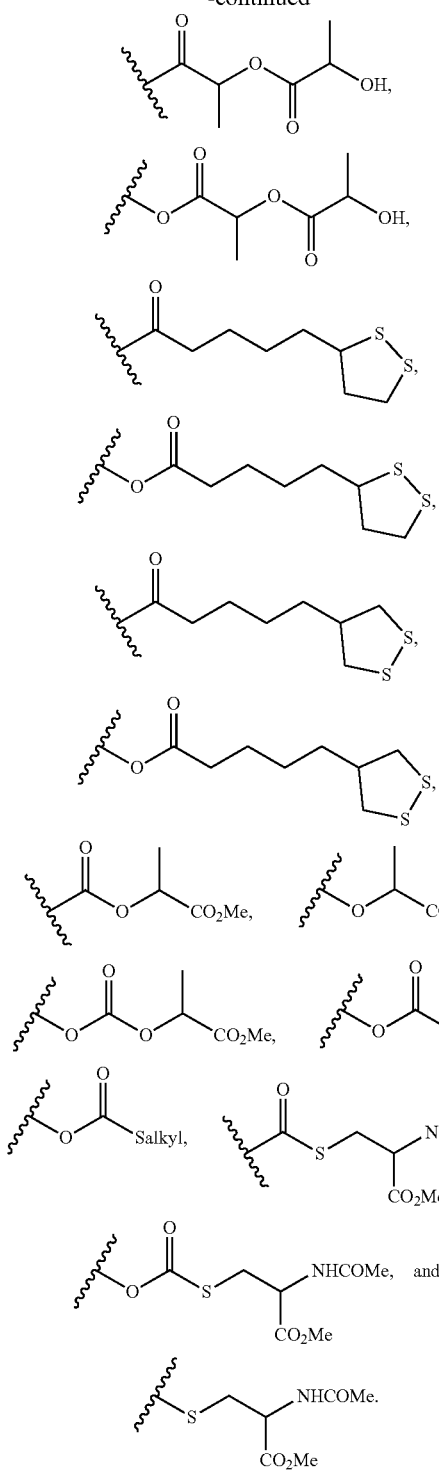
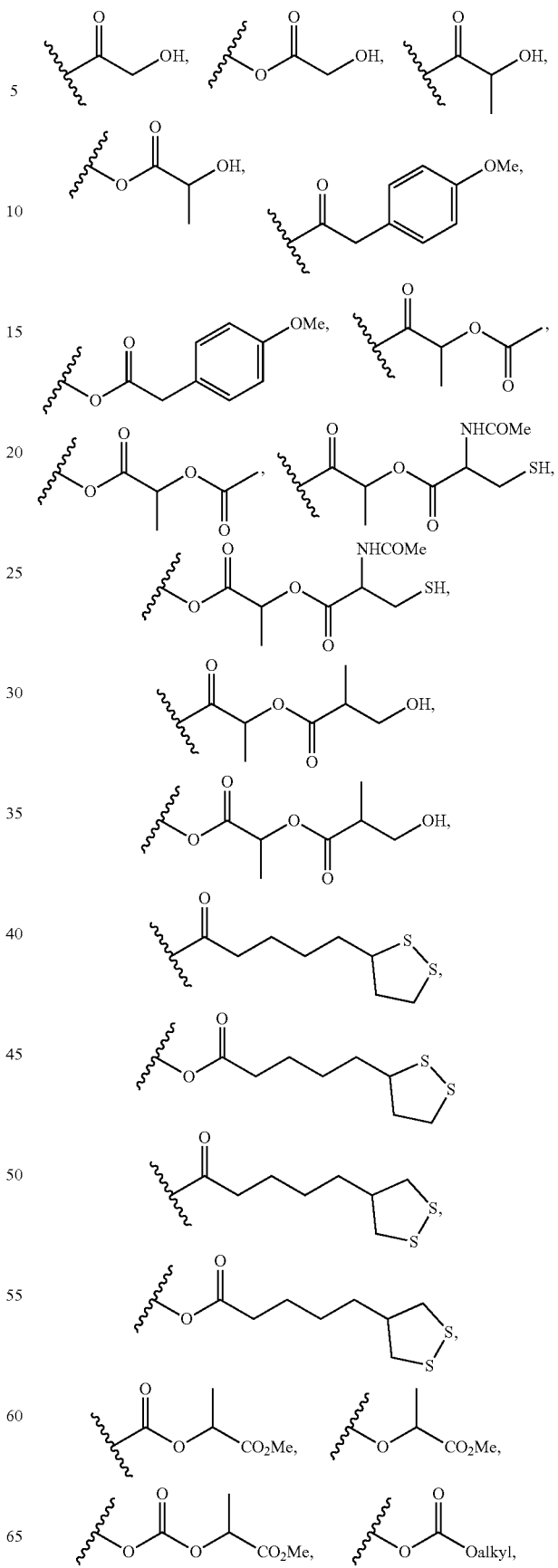
In some embodiments, the keratolyitic agent is —(C=O)$CH_2(OCH_2CH_2)_4OH$, —O(C=O)$CH_2(OCH_2CH_2)_4OH$, —(C=O)$CH_2CH_2(OCH_2CH_2)_4OH$, —O(C=O)$CH_2CH_2$ $(OCH_2CH_2)_4OH$, —$CO_2$alkyl(e.g., methyl, ethyl, propyl, isopropyl, or t-butyl),

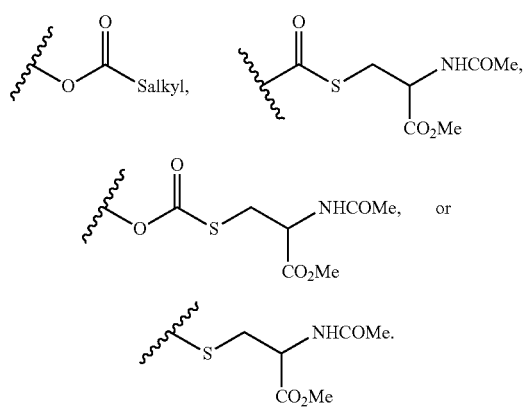

In some embodiments, the keratolytic agent is —O(C=O)CH₂(OCH₂CH₂)₄OH, —O(C=O)CH₂CH₂(OCH₂CH₂)₄OH, —CO₂alkyl (e.g., methyl, ethyl, propyl, isopropyl, or t-butyl),

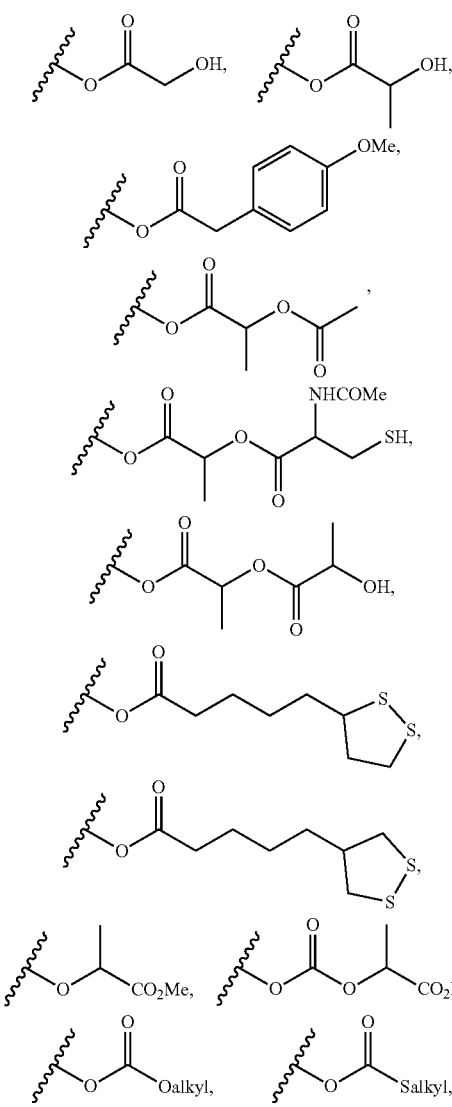

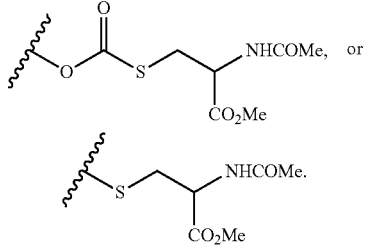

In some embodiments, the keratolytic agent is —C(O)CH₂OH, —C(O)CH(CH₃)OH, —C(O)CH₂(OCH₂CH₂)₄OH, —C(O)CH₂CH₂(OCH₂CH₂)₄OH,

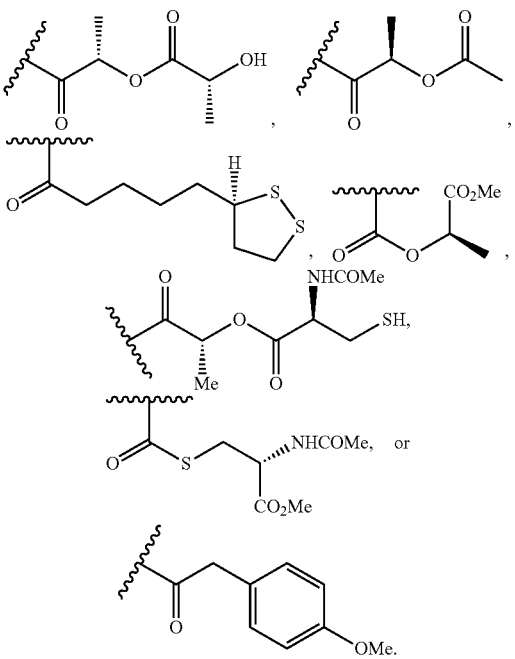

In some embodiments, D is a "keratolytic agent" radical that, upon release, hydrolysis, or other mechanism metabolizes or otherwise produces (e.g., when administered to an individual or patient, such as in or around the eye, such as the eyelid margin) an active keratolytic agent. In some instances, upon release (e.g., by hydrolysis or other mechanism), D produces a plurality of active keratolytic agents. In some instances, the active keratolytic agent comprises one or more of —SH, —OH, COOH (or COO—), or disulfide. In some embodiments, the active keratolytic agent is a carboxylic acid. In some embodiments, the active keratolytic agent is selected from the group consisting of acetic acid, glycolic acid, lactic acid, lipoic acid, pivalic acid, isobutryic acid, butyric acid, propionic acid, formic acid, and carbonic acid. In some embodiments, the active keratolytic agent is a thiol.

In certain instances, combination of an anti-inflammatory and/or anti-microbial moiety (e.g., having a structure of any formula provided herein, minus the R') with a keratolytic moiety (e.g., being represented by and/or having a structure of D). In certain embodiments, such moieties are radicals connected by a linker that is a bond, with the keratolytic moiety being hydrolyzable to produce both (1) an anti-inflammatory and/or anti-microbial agent and (2) one or more active keratolytic agent. In some embodiments, such moieties are radicals connected by a hydrolyzable linker, with the hydrolyzable linker being hydrolyzable, such that both (1) an anti-inflammatory and/or anti-microbial agent and (2) one or more active keratolytic agent are released (e.g., in vivo, such as after therapeutic (e.g., topical) delivery to the eye and/or skin).

In some embodiments, L is attached to D by a bond.

In some embodiments, R' is:

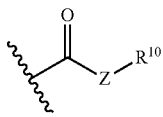

wherein:
Z is —O—, —S—, or —$(CR^8R^9)_m$—;
m is 1-6;
$R^8$ and $R^9$ are each independently H, halo, alkoxy, alkyl, heteroalkyl, or haloalkyl;
$R^{10}$ is H, —OH, alkyl, or heteroalkyl, the alkyl or heteroalkyl being optionally substituted,
or a pharmaceutically acceptable salt or solvate thereof.

In some embodiments, Z is —O— and $R^{10}$ is alkyl or heteroalkyl, the alkyl or heteroalkyl being optionally substituted. In some embodiments, Z is —O— and $R^{10}$ is —$CR^8R^9CO_2$alkyl. In some embodiments, $R^8$ and $R^9$ are each independently H, halo, alkyl, or haloalkyl. In some embodiments, $R^8$ and $R^9$ are each independently H or alkyl. In some embodiments, $R^8$ is methyl and $R^9$ is H. In some embodiments, Z is —O— and $R^{10}$ is —$CH(CH_3)CO_2$alkyl. In some embodiments, Z is —O— and $R^{10}$ is —$CH(CH_3)CO_2CH_3$. In some embodiments, if Z is —O— or —S—, $R^{10}$ is not —OH.

In some embodiments, Z is —S— and $R^{10}$ is alkyl or heteroalkyl, the alkyl or heteroalkyl being optionally substituted. In some embodiments, Z is —S— and $R^{10}$ is —$CR^8R^9CH(NHCOalkyl)(CO_2alkyl)$. In some embodiments, $R^8$ and $R^9$ are each independently H, halo, alkyl, or haloalkyl. In some embodiments, $R^8$ and $R^9$ are each independently H or alkyl. In some embodiments, $R^8$ and $R^9$ are each H. In some embodiments, Z is —S— and $R^{10}$ is —$CH_2CH(NHCOalkyl)(CO_2alkyl)$. In some embodiments, Z is —O— and $R^{10}$ is —$CH_2CH(NHCOCH_3)(CO_2CH_3)$.

In some embodiments, R' is:

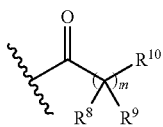

wherein:
m is 1-6;
$R^8$ and $R^9$ are each independently H, halo, alkoxy, alkyl, heteroalkyl, or haloalkyl;
$R^{10}$ is H, —OH, alkyl, heteroalkyl, —O(C=O)heteroalkyl, —O(C=O)alkyl, or aryl, the alkyl, heteroalkyl, —O(C=O)heteroalkyl, —O(C=O)alkyl, or aryl optionally substituted,
or a pharmaceutically acceptable salt or solvate thereof.

In some embodiments, $R^{10}$ is —OH, alkyl (e.g., methyl), heteroalkyl, —O(C=O)alkyl, or aryl, wherein the alkyl (e.g., methyl), heteroalkyl, aryl, or the alkyl of —O(C=O) alkyl is substituted with one or more substituent(s). In some embodiments, each substituent is independently selected from the group consisting of —OH, alkyl (e.g., alkylene), oxo, halo, alkoxy, alkylamide, thiol, and heterocycle, wherein the alkyl, alkoxy, alkylamide, or heterocycle are each independently optionally substituted. In some embodiments, the alkoxy is methoxy. In some embodiments, the alkylamide is methylamide. In some embodiments, the heterocycle comprises a disulfide. In some embodiments, the heterocycle is a dithiolane. In certain embodiments, at least one substituent is oxo. In some embodiments, at least one substituent is alkyl (e.g., methyl). In certain embodiments, at least one substituent is hydroxyl.

In some embodiments, $R^{10}$ is —O(C=O)alkylene, wherein the alkylene is substituted with one or more substituent(s). In specific embodiments, each substituent independently selected from the group consisting of methyl, —SH, —OH, and —NHCOCH_3. In some embodiments, $R^{10}$ is aryl, the aryl being substituted with methoxy. In some embodiments, $R^{10}$ is alkyl or heteroalkyl, wherein the alkyl or heteroalkyl is substituted with one or more substituent(s). In specific embodiments, each substituent is independently selected from the group consisting of —OH, heteroalkylene (e.g., $OCH_2CH_2$), and heterocycloalkyl (e.g., dithiolane).

In some embodiments, the alkyl or heteroalkyl of $R^{10}$ is substituted with one or more substituent, each substituent being independently selected from the group consisting of alkyl, heteroalkyl, hydroxyl, thiol, thioether, disulfide, seleno, selenol, sulfone, amide, ester, halo, oxo, heterocyclyl, and cycloalkyl, wherein the heterocyclyl and cycloalkyl is optionally substituted. In some embodiments, the heterocyclyl and cycloalkyl is substituted with one or more substituent selected from the group consisting of alkyl, heteroalkyl, hydroxyl, thiol, thioether, disulfide, selenol, sulfone, amide, ester, halo, and oxo. In some embodiments, the alkyl or heteroalkyl of $R^{10}$ is —C(O)alkyl or —C(O)heteroalkyl, the alkyl or heteroalkyl is optionally substituted with one or more substituent, each substituent being independently selected from the group consisting of alkyl, heteroalkyl, hydroxyl, thiol, thioether, disulfide, amide, halo, oxo, heterocyclyl, and cycloalkyl, wherein the heterocyclyl or cycloalkyl is optionally substituted.

In some embodiments, $R^8$ and $R^9$ are each independently hydrogen, halo, or alkyl. In some embodiments, $R^8$ is alkyl and $R^9$ is hydrogen. In some embodiments, $R^8$ is haloalkyl and $R^9$ is hydrogen. In some embodiments, $R^8$ is methyl and $R^9$ is hydrogen. In some embodiments, $R^8$ is halo and $R^9$ is hydrogen. In some embodiments, $R^8$ and $R^9$ are each halo. In some embodiments, $R^8$ and $R^9$ are each alkyl. In some embodiments, $R^8$ and $R^9$ are each hydrogen. In some embodiments, m is 1-3. In some embodiments, m is 1 or 2. In some embodiments, m is 1.

In some embodiments, $R^{10}$ is selected from the group consisting of —OH, alkyl, aryl, or heteroalkyl, the alkyl, aryl, or heteroalkyl being optionally substituted. In some embodiments, $R^{10}$ is —OH. In some embodiments, $R^{10}$ is alkyl substituted with oxo and further substituted with one or more substituents selected from the group consisting of substituted alkyl and substituted heteroalkyl. In some embodiments, the alkyl is substituted with one or more of the group selected from —SH, —OH, substituted or unsubstituted heteroalkyl, and substituted or unsubstituted heterocycloalkyl. In some embodiments, the alkyl is substituted with one or more of the group selected from halo, alkyl, alkoxy, or heteroalkyl. In some embodiments, the alkoxy is methoxy. In some embodiments, $R^{10}$ is heteroalkyl substituted with oxo and one or more of the group selected from substituted alkyl and substituted heteroalkyl. In some embodiments, the heteroalkyl is substituted with one or more of the group selected from —SH, —OH, and substituted or unsubstituted heteroalkyl. In some embodiments, the heteroalkyl is substituted with one or more of the group selected from —SH, —OH, alkyl, (C=O)alkyl, (C=O)heteroalkyl, and —NH(C=O)alkyl.

In some embodiments, $R^{10}$ comprises one or more of the group selected from —O— (ether), —SH, —S— (thioether), —OH, COOH, ester (e.g., in-line ester, such as —C(=O)O— or —OC(=O)—), carbonate, selenium, or disulfide. In some embodiments, $R^{10}$ comprises one or more of the group selected from —SH, —OH, sulfide, and —COOH. In some embodiments, $R^{10}$ comprises —SH, —OH, sulfide, or —COOH. In some embodiments, $R^{10}$ comprises —SH. In some embodiments, $R^{10}$ comprises —OH. In some embodiments, $R^{10}$ comprises sulfide.

In some embodiments, $R^{10}$ comprises one or more of the group selected from —OH, —(OCH$_2$CH$_2$)$_4$OH, —CH$_2$(OCH$_2$CH$_2$)$_4$OH, —O(C=O)alkyl, —CHCH$_3$, CO$_2$alkyl,

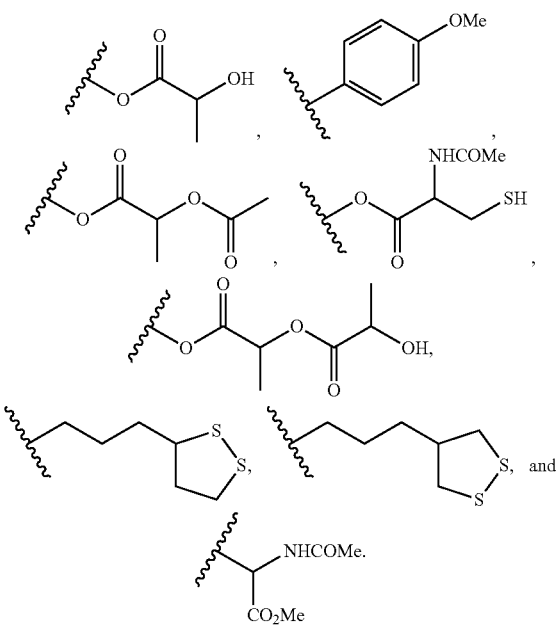

In some embodiments, $R^{10}$ is —OH, —(OCH$_2$CH$_2$)$_4$OH, —CH$_2$(OCH$_2$CH$_2$)$_4$OH, —O(C=O)alkyl, —CHCH$_3$, CO$_2$alkyl,

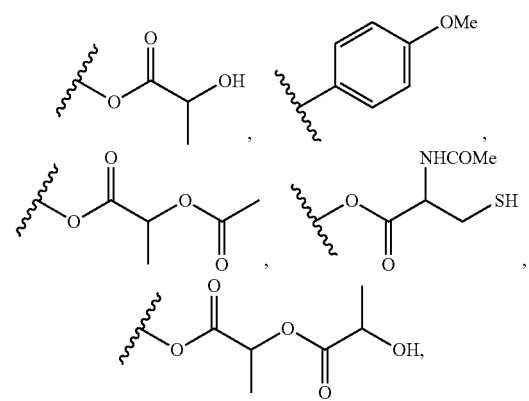

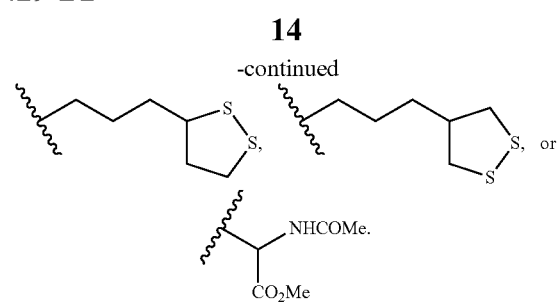

In some embodiments, R' is —OH, —C(O)CH$_2$OH, —C(O)CH(CH$_3$)OH, —C(O)CH$_2$(OCH$_2$CH$_2$)$_4$OH, —C(O)CH$_2$CH$_2$(OCH$_2$CH$_2$)$_4$OH,

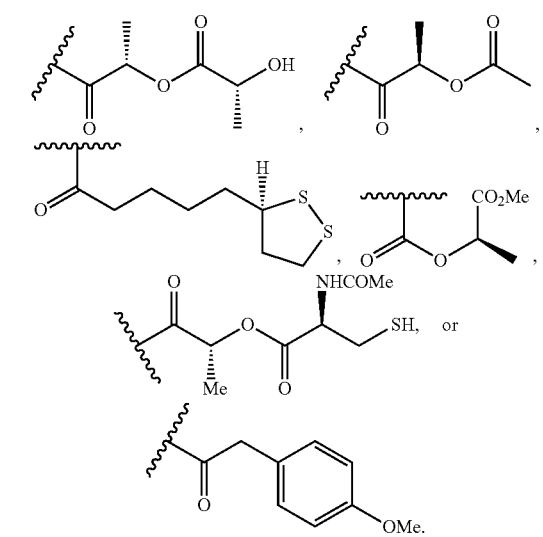

One embodiment provides a compound, or a pharmaceutically acceptable salt thereof, having the structure of Formula (I'):

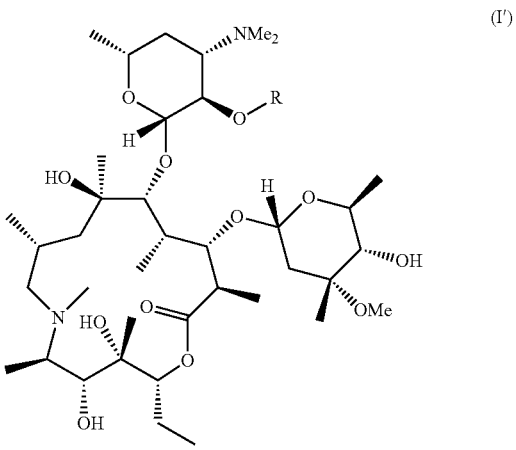

wherein

R is —C(O)CH(R$^1$)(R$^2$), wherein

R$^1$ is —OH, optionally substituted —O—C(O)alkyl, optionally substituted phenyl, —X(OCH$_2$CH$_2$)$_n$OR$^3$, or

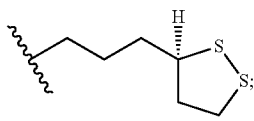 [SMILES: *CCC[C@@H]1CCSS1]

R² is selected from hydrogen or C1-C4 alkyl;
X is a direct bond, or an optionally substituted C1-C3 alkylene;
R³ is H or optionally substituted C1-C3 alkyl; and
n is 1 to 20.

In some embodiments, R¹ is —OH, optionally substituted phenyl, —X(OCH₂CH₂)$_n$OR³, or alkyl-heterocyclyl. In some embodiments, R¹ is substituted phenyl. In some embodiments, the phenyl is substituted with one or more of the group selected from halo, alkyl, heteroalkyl, cyano, cycloalkyl, and heterocycloalkyl. In some embodiments, the phenyl is substituted with halo, alkyl, heteroalkyl, cyano, cycloalkyl, or heterocycloalkyl. In some embodiments, the heteroalkyl is alkoxy. In some embodiments, the heteroalkyl is methoxy.

In some embodiments, R¹ is alkyl-heterocyclyl. In some embodiments, the heterocyclyl comprises a disulfide in the ring structure thereof. In some embodiments, R¹ is alkyl-heterocyclyl and the heterocyclyl comprises a disulfide in the ring structure thereof. In some embodiments, the heterocyclyl is a dithiolane.

In some embodiments, R¹ is X(OCH₂CH₂)$_n$OR³. In some embodiments, R³ is hydrogen. In some embodiments, R³ is substituted methylene, substituted ethylene, or substituted propylene. In some embodiments, R³ is methylene, ethylene, or propylene. In some embodiments, X is a bond. In some embodiments, X is substituted methylene, substituted ethylene, or substituted propylene. In some embodiments, X is methylene, ethylene, or propylene.

In some embodiments, n is 1-15. In some embodiments, n is 1-10. In some embodiments, n is 1-5. In some embodiments, n is 1. In some embodiments, n is 2.

In some embodiments, R¹ is optionally substituted —O—C(O)alkyl. In some embodiments, the optionally substituted alkyl of the optionally substituted —O—C(O)alkyl comprises one or more group selected from —SH, —OH, alkyl (e.g., alkylene), and —NHCOalkyl. In some embodiments, the alkyl is methyl, ethyl, propyl, isopropyl, and tert-butyl. In some embodiments, the optionally substituted alkyl of the optionally substituted —O—C(O)alkyl is methyl, CH(—NHCOalkyl)(CH₂SH), or CH(CH₃)OH.

In some embodiments, R² is H. In some embodiments, R² is methyl, ethyl, propyl, isopropyl, or t-butyl.

In some embodiments, R is —(C═O)CH₂(OCH₂CH₂)₄OH, —(C═O)CH₂CH₂(OCH₂CH₂)₄OH, —CO₂alkyl (e.g., methyl, ethyl, propyl, isopropyl, or t-butyl),

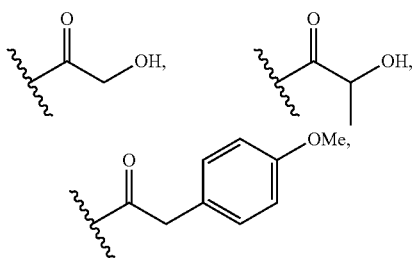

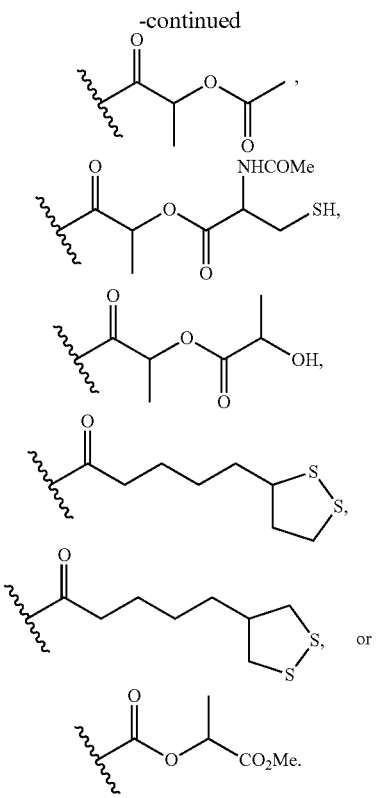

One embodiment provides a pharmaceutical composition comprising any compound provided herein, such as a compound of any one of Formulas (I), (Ia), (Ib), or (I'), or a pharmaceutically acceptable salt thereof, and at least one pharmaceutically acceptable excipient. Another embodiment provides the pharmaceutical composition, wherein the pharmaceutical composition is suitable for ophthalmic administration. Another embodiment provides the pharmaceutical composition, wherein the pharmaceutical composition is suitable for topical ophthalmic administration. In some embodiments, topical ophthalmic administration is administration in and/or around the eye, such as to the eyelid margin. In some embodiments, topical ophthalmic administration is administration to the ocular surface and the inner surface to the eyelid.

In some embodiments, a compound or a pharmaceutical composition comprising any compound provided herein, such as a compound of any one of Formulas (I), (Ia), (Ib), or (I'), or a pharmaceutically acceptable salt thereof, is substantially susceptible to hydrolysis. In some embodiments, the compound or the pharmaceutical composition comprises a non-polar vehicle. In some embodiments, the compound or the pharmaceutical composition is formulated and stored in a non-polar vehicle.

In some embodiments, a compound or a pharmaceutical composition comprising any compound provided herein, such as a compound of any one of Formulas (I), (Ia), (Ib), or (I'), or a pharmaceutically acceptable salt thereof, has a $T_{1/2}$ in or when exposed to an aqueous composition (e.g., an aqueous biological environment (e.g., the eye), or buffer (e.g., HEPES)) of any suitable time, such as less than 2 hours, less than 60 minutes (min), 50 mins, 40 mins, 30 mins, 20 mins, 10 mins, 9 mins, 8 mins, 7 mins, 6 mins, 5 mins, 3 mins, 2 mins, 1 min, or less. In certain instances, rapid decomposition of the compound allows for the rapid release of active agent(s) (e.g., a free form of a radical of any one of the formulas provided herein, such as wherein R' is H, and one or more keratolytic agent into the local environment). In some embodiments, the compound (e.g., alone or in a pharmaceutical composition) has a $T_{1/2}$ in or when exposed to an aqueous composition (e.g., an aqueous biological environment (e.g., an eye) or buffer (e.g., HEPES)) of least 1 min, 2 mins, 3 mins, 4 mins, 5 mins, 6 mins, 7 mins, 8 mins, 9 mins, 10 mins, 20 mins, 30 mins, 40 mins, 50 mins, 60 mins, or more. In some embodiments, the compound or the pharmaceutical composition has a $T_{1/2}$ in aqueous buffer from 1 min to 60 mins, 1 min to 20 mins, 1 min to 20 mins, or 1 min to 5 min. In some embodiments, the compound (e.g., alone or in a pharmaceutical composition) has a $T_{1/2}$ in or when exposed to an aqueous composition of at most about 3 mins.

In some embodiments, a compound or a pharmaceutical composition comprising any compound provided herein, such as a compound of any one of Formulas (I), (Ia), (Ib), or (I'), or a pharmaceutically acceptable salt thereof, is hydrolyzed to an active pharmaceutical agent and a keratolytic agent. In some embodiments, the compound is hydrolyzed to an active pharmaceutical agent and a keratolytic agent in an ocular space. In some embodiments, the active pharmaceutical agent is an anti-inflammatory and/or anti-microbial agent. In some embodiments the anti-inflammatory and/or anti-microbial agent is azithromycin. In some embodiments, the keratolytic agent is a carboxylic acid. In some embodiments, the carboxylic acid is selected from the group consisting of acetic acid, glycolic acid, lactic acid, lipoic acid, pivalic acid, isobutryic acid, butyric acid, propionic acid, formic acid, and carbonic acid. In some embodiments, the active keratolytic agent is a thiol.

A compound or a pharmaceutical composition comprising any compound provided herein, such as a compound of any one of Formulas (I), (Ia), (Ib), (I'), (II), Table 1, Table 2, or Table 3, or a pharmaceutically acceptable salt thereof, is incorporated in the summary and the detailed description by reference. The results of Table 3 are incorporated in the summary and the detailed description by reference.

One embodiment provides a method of treating an ophthalmic disease or disorder in a patient in need of thereof, comprising administering to the patient a composition comprising any compound provided herein, such as a compound of any one of Formulas (I), (Ia), (Ib) or (I'), or a pharmaceutically acceptable salt thereof. Another embodiment provides the method wherein the ophthalmic disease or disorder is selected from dry eye, lid wiper epitheliopathy (LWE), contact lens discomfort (CLD), contact lens discomfort, dry eye syndrome, evaporative dry eye syndrome, aqueous deficiency dry eye syndrome, blepharitis, keratitis, meibomian gland dysfunction, conjunctivitis, lacrimal gland disorder, inflammation of the anterior surface of the eye, infection of the anterior surface of the eye, infection of the lid, demodex lid infestation, lid wiper epitheliopathy and autoimmune disorder of the anterior surface of the eye.

In certain embodiments, provided herein is a method of treating an ocular (e.g., peri-ocular) or dermatological indication (e.g., associated with keratolytic activity, inflammation, and/or microbial infiltration), the method comprising administering a therapeutically effective amount of a compound or composition provided herein. In some embodiments, a composition provided herein (e.g., used in a method provided herein) comprises a compound provided herein in a therapeutically effective amount (e.g., at a concentration effective to treat keratosis/keratolytic activity, inflammation, and/or microbial infiltration), in the eye, surrounding tissue, or skin. In certain embodiments, a (e.g., pharmaceutical and/or ophthalmic) composition provided herein comprises about 0.1 wt. % to about 10 wt. % of a compound provided herein.

Ocular and/or dermatological disorders include inflammatory conditions of the eyelids (e.g., hordeolum (stye), blepharitis, and chalazion), ocular surface (e.g., dry eye disease and anterior uveitis) and posterior eye (e.g., posterior and pan-uveitis), abnormalities of the peri-ocular glands (e.g., meibomian gland dysfunction (MGD)), allergic-type conditions, (e.g., eczema, atopic dermatitis, atopic keratoconjunctivitis refractory to topical steroid treatment, and vernal keratoconjunctivitis), surgical complications (e.g., corneal transplant rejection, post-corneal transplant glaucoma, cataracts secondary to phakic corneal transplant, fungal infections in keratoplasty patients, and post-LASIK dry eye and/or poor refractive outcomes), corneal abnormalities (e.g., inflammatory corneal ulceration, rheumatoid corneal ulcers, and Thygeson's superficial punctate keratitis), conjunctival abnormalities (e.g., iridocyclitis, ligneous conjunctivitis), ocular complications from systemic treatments and/or autoimmune diseases (e.g., pauciarticular juvenile rheumatoid arthritis, graft versus host disease, and sjogren's syndrome) and/or infectious disease of the anterior surface of the eye. Provided herein are compositions and methods for the treatment of ocular and periocular abnormalities that are known to have multifactorial etiologies and interactions.

INCORPORATION BY REFERENCE

All publications, patents, and patent applications mentioned in this specification are herein incorporated by reference for the specific purposes identified herein.

DETAILED DESCRIPTION OF THE INVENTION

Certain Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The terms "treat," "treating," or "treatment" as used herein, include reducing, alleviating, abating, ameliorating, relieving, or lessening the symptoms associated with a disease, disease state, or indication (e.g., MGD) in either a chronic or acute therapeutic scenario. In one embodiment, treatment includes a reduction of a terminal duct obstruction. Also, treatment of a disease or disease state described herein includes the disclosure of use of such compound or composition for the treatment of such disease, disease state, or indication.

The term "opening" refers to the clearing (at least in part) of an obstructed meibomian gland canal or orifice and/or maintaining the patency of the meibomian gland canal or orifice.

The term "keratolytic agent" and/or "keratoplastic agent" as used herein refers to an agent that softens, disrupts, dissolves, solubilizes, or loosens a keratinized obstruction, or prevents the formation of a keratinized obstruction. Specifically, the term "keratolytic agents" refers to agents used to promote softening and dissolution of keratin and the term "keratoplastic agents" refers to agents used to reduce keratin production.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.

"Alkyl" generally refers to a straight or branched hydrocarbon chain radical consisting solely of carbon and hydrogen atoms, such as having from one to fifteen carbon atoms (e.g., $C_1$-$C_{15}$ alkyl). Unless otherwise stated, alkyl is saturated or unsaturated (e.g., an alkenyl, which comprises at least one carbon-carbon double bond). Disclosures provided herein of an "alkyl" are intended to include independent recitations of a saturated "alkyl," unless otherwise stated. Alkyl groups described herein are generally monovalent, but may also be divalent (which may also be described herein as "alkylene" or "alkylenyl" groups). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. In general, alkyl groups are each independently substituted or unsubstituted. Each recitation of "alkyl" provided herein, unless otherwise stated, includes a specific and explicit recitation of an unsaturated "alkyl" group. Similarly, unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is optionally substituted as described for "alkyl" groups.

"Alkylene" or "alkylene chain" generally refers to a straight or branched divalent alkyl group linking the rest of the molecule to a radical group, such as having from one to twelve carbon atoms, for example, methylene, ethylene, propylene, i-propylene, n-butylene, and the like. Unless stated otherwise specifically in the specification, an alkylene chain is optionally substituted as described for alkyl groups herein.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)R^a$ (where t is 1 or 2), —$R^b$—$S(O)OR^a$ (where t is 1 or 2) and —$R^b$—$S(O)_tN$ (R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" or "aryl-alkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" or "cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl or cycloalkyl is saturated (i.e., containing single C—C bonds only) or unsaturated (i.e., containing one or more double bonds or triple bonds). Examples of saturated cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)R$^a$ (where t is 1 or 2), —R$^b$—S(O)OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Carbocyclylalkenyl" refers to a radical of the formula —R$^c$-carbocyclyl where R$^c$ is an alkynylene chain as defined above. The alkenylene chain and the carbocyclyl radical is optionally substituted as defined above.

"Carbocyclylalkynyl" refers to a radical of the formula —R$^c$-carbocyclyl where R$^c$ is an alkynylene chain as defined above. The alkynylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

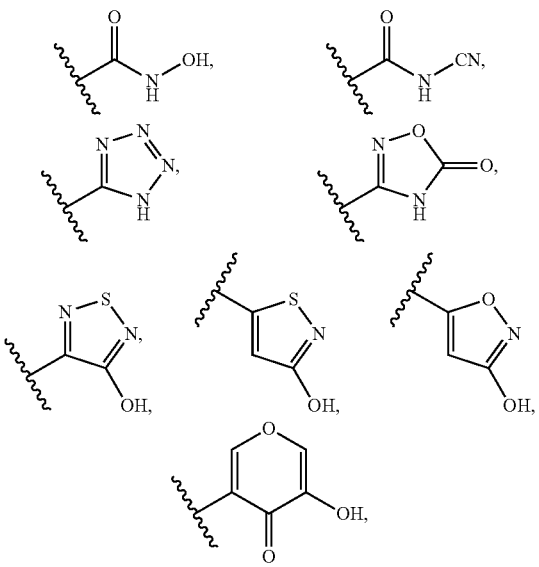

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

The term "heteroalkyl" refers to an alkyl group as defined above in which one or more skeletal carbon atoms of the alkyl are substituted with a heteroatom (with the appropriate number of substituents or valencies—for example, —$CH_2$— may be replaced with —NH— or —O—). For example, each substituted carbon atom is independently substituted with a heteroatom, such as wherein the carbon is substituted with a nitrogen, oxygen, selenium, or other suitable heteroatom. In some instances, each substituted carbon atom is independently substituted for an oxygen, nitrogen (e.g. —NH—, —N(alkyl)-, or —N(aryl)- or having another substituent contemplated herein), or sulfur (e.g. —S—, —S(=O)—, or —S(=O)$_2$—). In some embodiments, a heteroalkyl is attached to the rest of the molecule at a carbon atom of the heteroalkyl. In some embodiments, a heteroalkyl is attached to the rest of the molecule at a heteroatom of the heteroalkyl. In some embodiments, a heteroalkyl is a $C_1$-$C_{18}$ heteroalkyl. In some embodiments, a heteroalkyl is a $C_1$-$C_{12}$ heteroalkyl. In some embodiments, a heteroalkyl is a $C_1$-$C_6$ heteroalkyl. In some embodiments, a heteroalkyl is a $C_1$-$C_4$ heteroalkyl. Representative heteroalkyl groups include, but are not limited to —$OCH_2OMe$, or —$CH_2CH_2OMe$. In some embodiments, heteroalkyl includes alkoxy, alkoxyalkyl, alkylamino, alkylaminoalkyl, aminoalkyl, heterocycloalkyl, heterocycloalkyl, and heterocycloalkylalkyl, as defined herein. Unless stated otherwise specifically in the specification, a heteroalkyl group is optionally substituted as defined above for an alkyl group.

"Heteroalkylene" refers to a divalent heteroalkyl group defined above which links one part of the molecule to another part of the molecule. Unless stated specifically otherwise, a heteroalkylene is optionally substituted, as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

In general, optionally substituted groups are each independently substituted or unsubstituted. Each recitation of an optionally substituted group provided herein, unless otherwise stated, includes an independent and explicit recitation of both an unsubstituted group and a substituted group (e.g., substituted in certain embodiments, and unsubstituted in certain other embodiments). Unless otherwise stated, substituted groups may be substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

The compounds disclosed herein, reference to any atom includes reference to isotopes thereof. For example reference to H includes reference to any isotope thereof, such as a $^1$H, $^2$H, $^3$H, or mixtures thereof. "Pharmaceutically acceptable salt" includes both acid and base addition salts. A pharmaceutically acceptable salt of any one of the keratolytic conjugates described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Meibomian Gland

The meibomian glands are large sebaceous glands located in the eyelids, and unlike skin, are unassociated with hair. The meibomian glands produce the lipid layer of the tear film that protects it against evaporation of the aqueous phase. The meibomian gland orifice is located on the epithelial side of the lid margin, and is only a few hundred microns from the mucosal side. The glands are located on both upper and lower eyelids, with higher amounts of the glands on the upper eyelid. A single meibomian gland is composed of clusters of secretory acini that are arranged circularly around a long central duct and connected to it by short ductules. The terminal part of the central duct is lined by an ingrowth of the epidermis that covers the free lid margin and forms a short excretory duct that opens as an orifice at the posterior part of the lid margin just anterior to the mucocutaneous junction near the inner lid border. The oily secretion composed of lipids is synthesized within the secretory acini. The lipid secretion is a liquid at near body temperature and is delivered to the skin of the lid margin as a clear fluid, called "meibum." It forms shallow reservoirs on the upper and lower lid margins, and consists of a complex mixture of cholesterol, wax, cholesteryl esters, phospholipids, with small amounts of triglycerides, triacylglycerols, and hydrocarbons. The separate meibomian glands are arranged in parallel, and in a single row throughout the length of the tarsal plates in the upper and lower lids. The extent of the glands corresponds roughly to the dimensions of the tarsal plates.

The term "keratinized obstruction" as used herein refers to a blockage of the meibomian gland, regardless of the location of the blockage. In some embodiments, the blockage is complete, whereas in other embodiments, the blockage is partial. Regardless of the degree of blockage, such keratinized obstruction leads to meibomian gland dysfunction. In some embodiments, the keratinized obstruction is composed of keratinized material and lipids. In some embodiments, the keratinized obstruction is a blockage at the meibomian gland orifice and excretory duct. In some embodiments, the keratinized obstruction is caused by keratinization of the epithelium at the lid margin and meibomian gland. In certain instances, the keratin obstruction is influenced by the migration or aberrant differentiation of stem cells. In some embodiments, the keratinized obstruction results in reduced delivery of oil to the lid margin and tear film, and stasis inside the meibomian gland that causes increased pressure, resultant dilation, acinar atrophy, and low secretion. In certain instances, keratinization of the meibomian gland causes degenerative gland dilation and atrophy.

Ocular Surface Diseases or Disorders

Ocular surface diseases is a group of diseases including, but not limited to, dry eye syndrome (including evaporative DES and/or aqueous deficiency DES), blepharitis, keratitis, meibomian gland dysfunction, conjunctivitis, lacrimal gland disorder, contact lens related conditions and inflammatory, infectious, or autoimmune diseases or disorders of the anterior surface of the eye. The term, "meibomian gland dysfunction," as used herein, refers to chronic, diffuse abnormality of the meibomian glands, that is characterized by terminal duct obstruction or qualitative or quantitative changes in the glandular secretion, or both. MGD may result in alteration of the tear film, eye irritation symptoms, inflammation, or ocular surface disease. The most prominent aspects of MGD are obstruction of the meibomian gland orifices and terminal ducts and changes in the meibomian gland secretions.

In some instances, meibomian gland dysfunction (MGD) is a chronic, diffuse abnormality of the meibomian glands, commonly characterized by terminal duct obstruction and/or qualitative/quantitative changes in the glandular secretion. Terminal duct obstruction is caused by hyperkeratinization of the ductal epithelium (Nichols et al, Inv. Oph. & Vis. Sci. (2011); 52(4):1922-1929). These alterations in both meibum quality and expression may result in alteration of the tear film, symptoms of eye irritation, and ocular surface disease such as evaporative dry eye. The principal clinical consequence of MGD is evaporative dry eye syndrome and large population based studies (i.e., Bankok Study and the Shihpai Eye Study) estimate that over 60% of patients with dry eye symptoms also have MGD (Schaumberg et al, Investigative Ophthalmology and Visual Science. (2011); 52(4):1994-2005).

MGD is a leading contributor of dry eye syndrome. The occurrence of dry eye syndrome is widespread and affects about 20 million patients in the United States alone. Dry eye syndrome is a disorder of the ocular surface resulting from either inadequate tear production or excessive evaporation of moisture from the surface of the eye. Tears are important to corneal health because the cornea does not contain blood vessels, and relies on tears to supply oxygen and nutrients. Tears and the tear film are composed of lipids, water, and mucus, and disruption of any of these can cause dry eye. An inadequate amount of lipids flowing from the meibomian glands as caused by a keratinized obstruction, may cause excessive evaporation, thereby causing dry eye syndrome.

In some embodiments, altered meibomian gland secretion is detected by physically expressing the meibomian glands by applying digital pressure to the tarsal plates. In subjects without MGD, the meibum is a pool of clear oil. In MGD, both the quality and expressibility of the expressed material is altered. The altered meibum is also known as meibomian excreta and is made up of a mixture of altered secretions and keratinized epithelial material. In MGD, the quality of expressed lipid varies in appearance from a clear fluid, to a viscous fluid containing particulate matter and densely opaque, toothpaste-like material. The meibomian orifices may exhibit elevations above surface level of the lid, which is referred to as plugging or pouting, and is due to obstruction of the terminal ducts and extrusion of a mixture of meibomian lipid and keratinized material.

Obstructive MGD is characterized by all or some of the following: 1) chronic ocular discomfort, 2) anatomic abnormalities around the meibomian gland orifice (which is one or more of the following: vascular engorgement, anterior or posterior displacement of the mucocutaneous junction, irregularity of the lid margin) and 3) obstruction of the meibomian glands (obstructive findings of the gland orifices by slit lamp biomicroscopy (pouting, plugging or ridge), decreased meibum expression by moderate digital pressure).

Current methods for assessing and monitoring MGD symptoms include, but are not limited to patient questionnaires, meibomian gland expression, tear stability break up time, and determining the number of patent glands as seen by digital expression.

In some embodiments, the symptoms of a patient are assessed by asking the patient a series of questions. Questionnaires allow the assessment of a range of symptoms associated with ocular discomfort. In some embodiments, the questionnaire is the SPEED questionnaire. The SPEED questionnaire assesses frequency and severity of a patient's dry eye symptoms. It examines the occurrence of symptoms on the current day, past 72 hours and past three months. A SPEED score is tallied based on the patient's answers to the questions, to give a range of severity of the patient's symptoms. The SPEED questionnaire includes questions such as the following: 1) what dry eye symptoms are you experiencing, and when do they occur? 2) how frequently do you experience dryness, grittiness, or scratchiness in your eyes? 3) how often do you experience soreness or irritation of the eyes? 4) how often do you experience burning or watering of the eyes? 5) how often do you experience eye fatigue? and 6) how severe are the symptoms?

Meibomian gland expressibility is optionally determined to assess the meibomian gland function. In normal patients, meibum is a clear to light yellow oil. Meibum is excreted from the glands when digital pressure is placed on the glands. Changes in meibomian gland expressibility are one potential indicator of MGD. In some embodiments, during expression, quantifying the amount of physical force applied during expression is monitored in addition to assessing lipid volume and lipid quantity.

Tear stability break up time (TBUT) is a surrogate marker for tear stability. Tear film instability is a core mechanism in dry eye and MGD. Low TBUT implies a possibility of lipid layer compromise and MGD. TBUT is optionally measured by examining fluorescein breakup time, as defined as the time to initial breakup of the tear film after a blink. Fluorescein is optionally applied by wetting a commercially available fluorescein-impregnated strip with saline, and applied to the inferior fornix or bulbar conjuctiva. The patient is then asked to blink several times and move the eyes. The break up is then analyzed with a slit lamp, a cobalt blue filter, and a beam width of 4 mm. The patient is instructed to blink, and the time from upstroke of the last blink to the first tear film break or dry spot formation is recorded as a measurement.

Other methods for assessing MGD symptoms, include but are not limited to, Schirmer test, ocular surface staining, lid morphology analysis, meibography, meibometry, interferometry, evaporimetry, tear lipid composition analysis, fluorophotometry, meiscometry, osmolarity analysis, indices of tear film dynamics, evaporation and tear turnover.

Current treatments for MGD include lid warming, lid massage, lid hygiene, lid expression and meibomian gland probing. Pharmacological methods, prior to those described herein, have not been used.

Lid hygiene is considered the primary treatment for MGD and consists of three components: 1) application of heat, 2) mechanical massage of eyelids and 3) cleansing the eyelid. Eyelid warming procedures improve meibomian gland secretion by melting the pathologically altered meibomian lipids. Warming is achieved by warm compresses or devices. Mechanical lid hygiene includes the use of scrubs, mechanical expression and cleansing with various solutions of the eyelashes and lid margins. Lid margins are optionally also cleansed with hypoallergenic bar soap, dilute infant shampoo or commercial lid scrubs. Physical expression of meibomian glands is performed in a physician's office or is performed by the patient at home. The technique varies from gentle massage of the lids against the eyeball to forceful squeezing of the lids either against each other or between a rigid object on the inner lid surface and a finger, thumb, or rigid object (such as a glass rod, cotton swab, or metal paddle) on the outer lid surface. The rigid object on the inner lid surface protects the eyeball from forces transferred through the eyelid during expression and to offer a stable resistance, to increase the amount of force that is applied to the glands.

Eyelid warming is limited because the warming melts the lipids, but does not address movement of the keratinized material. Further, eyelid warming induces transient visual degradation due to corneal distortion. Mechanical lid hygiene is also limited because the force needed to remove an obstruction can be significant, resulting in significant pain to the patient. The effectiveness of mechanical lid hygiene is limited by the patient's ability to tolerate the associated pain during the procedure. Other treatments for MGD are limited.

Physical opening of meibomian glands obstruction by meibomian gland expression is an acceptable method to improve meibomian gland secretion and dry eye symptoms. In addition probing of the meibomian gland canal has been used to open the obstructed canal. Both methods, expression and probing, are limited, however, by the pain induced by the procedure, the possible physical insult to the gland and canal structures and their short lived effect estimated at days and weeks. Therefore, methods are needed to improve patient comfort, which will not cause harm to the meibomian glands and canals, that will reduce the dependency on frequent office visits and improve secretion of meibum.

U.S. Pat. No. 9,463,201 entitled, "Compositions and methods for the treatment of meibomian gland dysfunction" describes a method for treating meibomian gland dysfunction involving the topical administration of a therapeutically-effective amount of at least one keratolytic agent in an ophthalmically-acceptable carrier. The patent includes keratolytic agents that are inorganic selenium (Se) compounds such as selenium disulfide ($SeS_2$) or organoselenium compounds such as Ebselen (2-Phenyl-1,2-benzoselenazol-3-one). This agent would treat the underlying cause of MGD, but not a "plus" inflammatory disease as described by the DEWS report on MGD.

The role of inflammation in the etiology of MGD is controversial. The terms posterior blepharitis and MGD are not synonymous. Posterior blepharitis describes inflammatory conditions of the posterior lid margin and has various causes, of which MGD is only one possible cause (Nichols et al 2011). In its earliest stages, MGD is not associated with clinical signs characteristic of posterior blepharitis. As MGD progresses, an MGD-related posterior blepharitis is said to be present. MGD-related posterior blepharitis affects the meibomian glands and meibomian gland orifices. MGD-related posterior blepharitis is characterized by flora changes, esterase and lipase release, lipid changes, and eyelid inflammation. Hyperkeratinization of the meibomian gland epithelium (thickening of the lining of the glands) may lead to obstruction and a decrease in the quantity of meibomian gland secretions and may be responsible for MGD-related posterior blepharitis. Diagnosis of MGD-related posterior blepharitis includes meibomian gland expression with demonstration of an altered quality of expressed secretions, and/or by a loss of gland functionality (decreased or absent expressibility). The TFOS report on Meibomian Gland Disease specifically notes that anterior blepharitis and exacerbated inflammatory ocular surface disease are "plus" diseases to MGD which are managed by topical, ocular steroids (Nichols et al 2011). Since these "plus" conditions can be present in various levels of severity from early to late MGD there is a need for treatments and/or combinations of treatments that can target both the underlying non-inflammatory pathophysiology of MGD and inflammation associated with these comorbid conditions.

MGD-related inflammatory eye disease may comprise a different mechanism than blepharitis-related MGD. MGD-related inflammatory eye disease is characterized by an inflammatory cascade involving activation and migration of T lymphocytes to the inflamed tissue. T lymphocyte infiltration may result in lacrimal gland stimulation and upregulation of cytokines. Exemplary cytokines that may be involved in MGD-related inflammatory eye disease include, but are not limited to, interleukin-1, interleukin-4, interleukin-6, inteleukin-8, interferon gamma, macrophage inflammatory protein 1 alpha, and tumor necrosis factor alpha. Kinase pathways including the mitogen activated protein kinase (MAPK) pathway are also activated in the inflammatory cascade. The inflammatory process results in loss of mucin-producing goblet cells and destruction of the ocular surface that can lead to further damage.

Dry eye syndrome, also known as keratoconjunctivitis sicca (KCS), is considered a self-sustaining disease that is progressively disconnected from its initial cause. Dry eye syndrome is associated with inflammation at the ocular surface and periocular tissue. Inflammation is characterized by the activation and migration of T lymphocytes to the inflamed tissue including in the conjunctiva and lacrimal glands. Inflammatory cytokines, chemokines, and matrix metalloproteinase have also been identified as being increased.

Animal models of dry eye disease have been established and reviewed (Barabino, et al, (Invest. Ophthalmol. Vis. Sci. 2004, 45:1641-1646)). Barabino, et al, (Invest. Ophthalmol. Vis. Sci. 2005, 46:2766-2771) described a model wherein exposure of normal mice to a low-humidity environment in a controlled-environment chamber leads to significant alterations in tear secretion, goblet cell density, and acquisition of dry eye-related ocular surface signs. However, no single animal model adequately accounts for the immune, endocrine, neuronal and environmental factors which contribute to dry eye pathogenesis.

Anti-inflammatory agents may be used to treat ocular surface diseases or disorders including dry eye syndrome.

Corticosteroids are an effective anti-inflammatory therapy in dry eye disease. For example, in a 4-week, double-masked, randomized study in 64 patients with dry eye and delayed tear clearance, loteprednol etabonate 0.5% ophthalmic suspension (Lotemax [Bausch and Lomb, Rochester, N.Y.]), QID, was found to be more effective than its vehicle in improving some signs and symptoms (Pflugfelder et al, Am J Ophthalmol (2004); 138:444-57). The TFOS 2007 report on dry eye disease went so far as to conclude that, "In the US Federal Regulations, ocular corticosteroids receiving "class labeling" are indicated for the treatment " . . . of steroid responsive inflammatory conditions of the palpebral and bulbar conjunctiva, cornea and anterior segment of the globe such as allergic conjunctivitis, acne rosacea, superficial punctate keratitis, herpes zoster keratitis, iritis, cyclitis, selected infective conjunctivitis, when the inherent hazard of steroid use is accepted to obtain an advisable diminution in edema and inflammation." KCS, in some instances, is included in this list of steroid-responsive inflammatory conditions (Therapy Subcommittee of the International Dry Eye WorkShop, 2007. Management and Therapy of Dry Eye Disease: Report of the Management and Therapy Subcommittee of the International Dry Eye WorkShop (2007). 2007; 5: 163-178)." While the US FDA does not agree with this conclusion, short courses of steroids, especially Lotemax, are commonly used to treat inflammation associated with dry eye disease.

Other anti-inflammatory agents include nonsteroidal anti-inflammatory drugs (NSAIDs). NSAIDs inhibit the activity of cyclooxygenases including cyclooxygenase-1 (COX-1) and cyclooxygenase-2 (COX-2), which are enzymes involved in the synthesis of prostaglandins and thromboxanes from arachidonic acid. Prostaglandin and thromboxane signaling are involved in inflammation and immune modulation. In some cases, NSAIDs are used for treating dry eye disease by treating the inflammation at the ocular surface.

Treatment of dry eye is also accomplished through agents that enhance tear fluid and mucin production. For example, agonists of the $P2Y_2$ receptor have been shown to increase tear fluid and mucin secretion. The mechanism is thought to involve $P2Y_2$ signaling to raise intracellular calcium and open chloride channels in the apical membrane. The $P2Y_2$ receptor belongs to the family of purinergic receptors, which have been classified into P1 receptors and P2 receptors on the basis of their native agonism by purine nucleosides and purine and pyrimidine nucleotides, respectively. P2 receptors are further distinguished physiologically into two types: P2X receptors and P2Y receptors. The P2Y receptors are involved in diver signaling including platelet aggregation, immunity, lipid metabolism, and bone activity. Several studies have also demonstrated the presence of P2X and P2Y receptors in ocular tissues, including the retina, ciliary body, and lens. These studies indicate that $P2Y_2$ receptors appear to be the main subtype of purinergic receptor located at the ocular surface. $P2Y_2$ receptors have also been demonstrated to be localized in ocular tissues in the conjunctival epithelial goblet and serous cells and meibomian gland acinus and ductal epithelial cells of the rhesus macaque.

Azithromycin

Azithromycin is a macrolide antibiotic with a 15-membered ring. Its chemical name is (2R,3S,4R,5R,8R,10R,11R, 12S,13S,14R)-13-[(2,6-dideoxy-3-C-methyl-3-O-methyla-L-ribo-hexopyranosyl)oxy]-2-ethyl-3,4,10-trihydroxy-3,5, 6,8,10,12,14-heptamethyl11-[[3,4,6-trideoxy-3-(dimethylamino)-b-D-xylo-hexopyranosyl]oxy]-1-oxa-6-azacyclopentadecan-15-one having a molecular weight of 749, and an empirical formula is $C_{38}H_{72}N_2O_{12}$. The structural formula is:

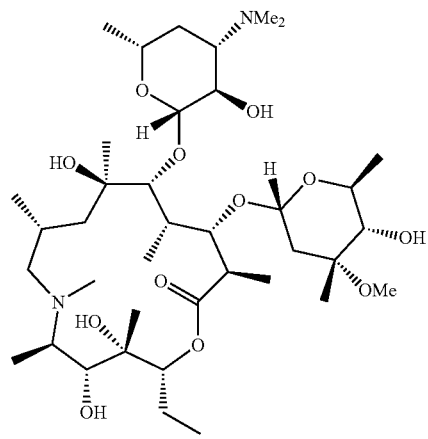 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2O)[C@](C)(O)C[C@@H](C)CN(C)[C@H](C)[C@@H](O)[C@]1(C)O]

Azithromycin acts by binding to the 50S ribosomal subunit of susceptible microorganisms and interfering with microbial protein synthesis. In the topical ophthalmic setting, Azithromycin is formulated as a 1% solution of pH 6.3 comprising benzalkonium chloride. Azithromycin is indicated for the treatment of bacterial conjunctivitis caused by susceptible isolates of the following microorganisms: *Haemophilus influenzae, Staphylococcus aureus, Streptococcus mitis* group, or *Streptococcus pneumoniae*. Further information about azithromycin ophthalmic solution can be found in U.S. Pat. Nos. 6,239,113, 6,569,443, or 7,056,893.

Meibomian Gland Dysfunction and Dry Eye Disease Pharmacological Agents

Keratolytic Conjugates

Described herein are keratolytic conjugates which address simultaneously the non-inflammatory keratolytic blockage component of meibomian gland dysfunction and the inflammation associated dry eye disease including aqueous deficiency. The keratolytic conjugates described herein are useful as either an acute therapy (e.g., by a trained specialist or physician) or as a chronic therapy (e.g., in the hands of a patient, or alternatively, by a trained specialist or physician). The agents are tested, in certain embodiments, using the assays and methods described herein (e.g., as described in the examples). The keratolytic conjugate described herein represent a significant advance in the art as the first-order metabolites obtained from metabolism of the agents are operative against both the keratolytic and the inflammatory component of dry eye disease.

One embodiment provides a compound, having the structure of Formula (Ia):

Formula (Ia)

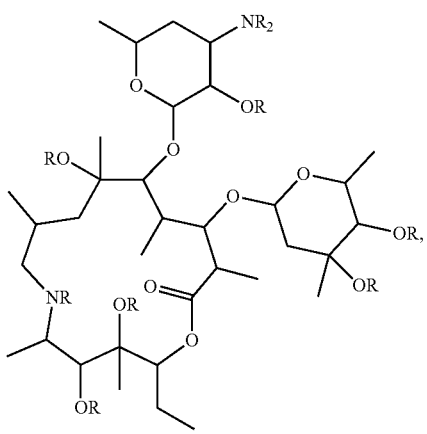

wherein,
each R is independently H, R', substituted or unsubstituted alkyl, or substituted or unsubstituted heteroalkyl, wherein at least one R is R';
R' is D-L-;
D is a keratolytic agent;
L is a linker,
or a pharmaceutically acceptable salt or solvate thereof.

One embodiment provides a compound, having the structure of Formula (Ib):

Formula (Ib)

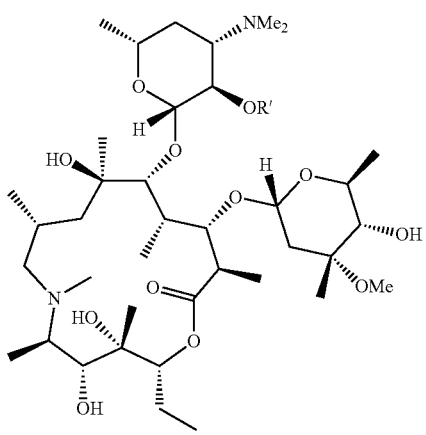

wherein,
R' is D-L-;
D is a keratolytic agent;
L is a linker,
or a pharmaceutically acceptable salt or solvate thereof.

In certain embodiments, a compound of Formula (Ia) or (Ib), wherein L comprises one or more linker groups, each linker group being selected from the group consisting of a bond, —O—, —S—, alkyl (alkylenyl), heteroalkyl (heteroalkylenyl), disulfide, ester, and carbonyl (>C=O). Another embodiment provides the compound of Formula (Ia) or (Ib), wherein the keratolytic agent comprises one or more groups of the group (e.g., keratolytic group, such as a group conferring keratolytic activity), each group (e.g., keratolytic group) being independently selected from the group consisting of thiol, disulfide, selenium (e.g., selenide, diselenide), carboxylic acid or a group which can be metabolized to a carboxylic acid.

Another embodiment provides the compound of Formula (Ia) or (Ib), where R' is alkyl or heteroalkyl substituted with at least one oxo, and further optionally substituted. Another embodiment provides the compound of Formula (Ia) or (Ib), wherein R' is:

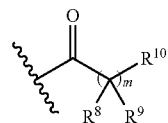

wherein:
m is 1-6;
$R^8$ and $R^9$ are each independently H, halo, alkoxy, alkyl, heteroalkyl, or haloalkyl;
$R^{10}$ is H, alkyl, aryl or heteroalkyl, the alkyl, aryl, or heteroalkyl being optionally substituted,
or a pharmaceutically acceptable salt or solvate thereof.

Another embodiment provides the compound of Formula (Ia) or (Ib), wherein the alkyl or heteroalkyl of $R^{10}$ is substituted with one or more substituent, each substituent being independently selected from the group consisting of alkyl, heteroalkyl, hydroxyl, thiol, thioether, disulfide, seleno, selenol, sulfone, amide, halo, oxo, heterocyclyl, and cycloalkyl, wherein the heterocyclyl and cycloalkyl is optionally substituted (e.g., with one or more substituent selected from the group consisting of alkyl, heteroalkyl, hydroxyl, thiol, thioether, disulfide, selenol, sulfone, amide, halo, and oxo).

Another embodiment provides the compound of Formula (Ia) or (Ib), wherein R' is selected from the group consisting of
—C(O)CH$_2$OH, —C(O)CH(CH$_3$)OH, —C(O)CH$_2$(OCH$_2$CH$_2$)$_4$OH, —C(O)CH$_2$CH$_2$(OCH$_2$CH$_2$)$_4$OH,

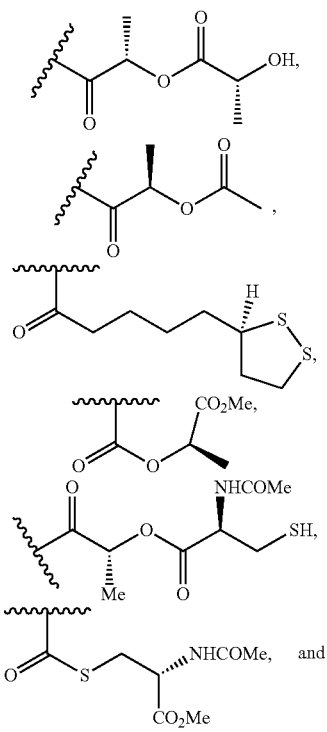

(I)

wherein
R is —C(O)CH(R¹)(R²), wherein
R¹ is —OH, optionally substituted —O—C(O)alkyl, optionally substituted —O—C(O)heteroalkyl, optionally substituted phenyl, —X(OCH$_2$CH$_2$)$_n$OR³, or R² is selected from hydrogen or C1-C4 alkyl;
X is a direct bond, or an optionally substituted C1-C3 alkylene;
R³ is H or optionally substituted C1-C3 alkyl; and
n is 1 to 20.

One embodiment provides a compound, or a pharmaceutically acceptable salt thereof, having the structure of Formula (Ia'):

(Ia')

wherein
R is —CH(R')(R²), wherein
R¹ is —OH, optionally substituted phenyl, or —X(OCH$_2$CH$_2$)$_n$OR³;

Another embodiment provides the compound of Formula (I) or (Ia), wherein R' is —C(O)CH(R¹)(R²);
R¹ is H, —OH, optionally substituted —O—C(O)alkyl, optionally substituted phenyl, —X(OCH$_2$CH$_2$)$_n$OR³, or optionally substituted alkyl-heterocyclyl;
R² is H or C$_1$-C$_4$ alkyl;
X is a direct bond, or an optionally substituted C1-C3 alkylene;
R³ is H or optionally substituted C1-C3 alkyl; and
n is 1 to 20,
or a pharmaceutically acceptable salt or solvate thereof.

Another embodiment provides the compound of Formula (I) or (Ia), wherein R¹ is alkyl-heterocyclyl and the heterocyclyl comprises a disulfide in the ring structure thereof. In some embodiments, the heterocyclyl is a dithiolane. In some embodiments, R¹ is Another embodiment provides the compound of Formula (I) or (Ia), wherein R¹ is —OH. Another embodiment provides the compound of Formula (I) or (Ia), wherein R¹ is optionally substituted phenyl. Another embodiment provides the compound of Formula (I) or (Ia), wherein R¹ is —X(OCH$_2$CH$_2$)$_n$OR³. In some embodiments, X is a direct bond. In some embodiments, X is an optionally substituted C$_1$-C$_3$ alkylene.

Another embodiment provides the compound of Formula (I) or (Ia), wherein R³ is hydrogen. In some embodiments, R³ is optionally substituted C1-C3 alkyl.

Another embodiment provides the compound of Formula (I) or (Ia), wherein n is 20.

Another embodiment provides the compound of Formula (I) or (Ia), wherein R² is H. In some embodiments, R² is C1-C4alkyl. In some embodiments, R² is CH$_3$.

One embodiment provides a compound, or a pharmaceutically acceptable salt thereof, having the structure of Formula (I):

R² is selected from hydrogen or C1-C4 alkyl;

X is a direct bond, or an optionally substituted C1-C3 alkylene;

R³ is H or optionally substituted C1-C3 alkyl; and n is 1 to 20.

Another embodiment provides the compound of Formula (I') or (Ia'), or a pharmaceutically acceptable salt thereof, wherein R¹ is —OH. Another embodiment provides the compound of Formula (I') or (Ia'), or a pharmaceutically acceptable salt thereof, wherein R¹ is optionally substituted phenyl. Another embodiment provides the compound of Formula (I') or (Ia'), or a pharmaceutically acceptable salt thereof, wherein R¹ is —X(OCH₂CH₂)$_n$OR³.

Another embodiment provides the compound of Formula (I') or (Ia'), or a pharmaceutically acceptable salt thereof, wherein X is a direct bond. Another embodiment provides the compound of Formula (I') or (Ia'), or a pharmaceutically acceptable salt thereof, wherein R³ is hydrogen. Another embodiment provides the compound of Formula (I') or (Ia'), or a pharmaceutically acceptable salt thereof, wherein R³ is optionally substituted C1-C3 alkyl. Another embodiment provides the compound of Formula (I') or (Ia'), or a pharmaceutically acceptable salt thereof, wherein n is 20.

Another embodiment provides the compound of Formula (I') or (Ia'), or a pharmaceutically acceptable salt thereof, wherein X is an optionally substituted C1-C3 alkylene. Another embodiment provides the compound of Formula (I') or (Ia'), or a pharmaceutically acceptable salt thereof, wherein R³ is hydrogen. Another embodiment provides the compound of Formula (I') or (Ia'), or a pharmaceutically acceptable salt thereof, wherein R³ is optionally substituted C₁-C₃ alkyl. Another embodiment provides the compound of Formula (I') or (Ia'), or a pharmaceutically acceptable salt thereof, wherein n is 20.

Another embodiment provides the compound of Formula (I') or (Ia'), or a pharmaceutically acceptable salt thereof, wherein R² is hydrogen. Another embodiment provides the compound of Formula (I') or (Ia'), or a pharmaceutically acceptable salt thereof, wherein R² is C1-C4 alkyl. Another embodiment provides the compound of Formula (I') or (Ia'), or a pharmaceutically acceptable salt thereof, wherein R² is CH₃.

One embodiment provides a compound having the structure of Formula (II):

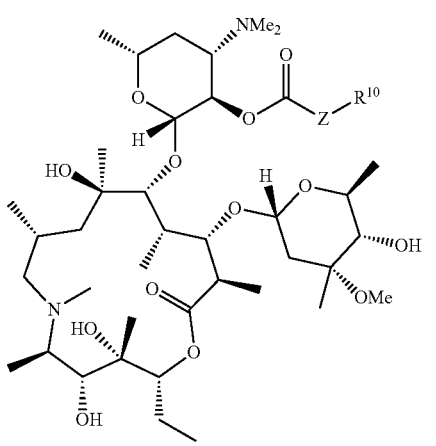

Formula (II)

wherein,

Z is —O— or —(CR⁸R⁹)$_m$—;

m is 1-6;

R⁸ and R⁹ are each independently H, halo, alkoxy, alkyl, heteroalkyl, or haloalkyl;

R¹⁰ is H, —OH, alkyl, or heteroalkyl, the alkyl or heteroalkyl being optionally substituted, or a pharmaceutically acceptable salt or solvate thereof.

In some embodiments, Z is —CR⁸R⁹—. In some embodiments, R⁸ is H or methyl and R⁹ is H. In some embodiments, R¹⁰ is —OH, —(OCH₂CH₂)₄OH, —CH₂(OCH₂CH₂)₄OH, —O(C=O)CH₃,

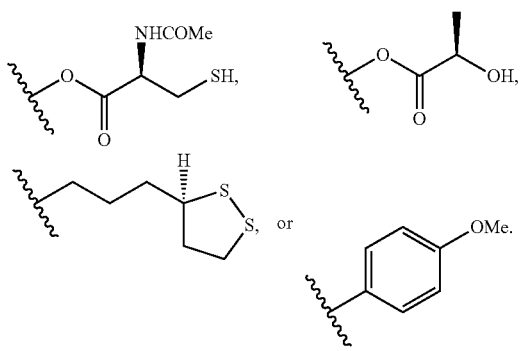

In some embodiments, Z is —O—. In some embodiments, R¹⁰ is

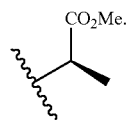 [SMILES: *[C@H](C)C(=O)OC]

One embodiment provides a keratolytic conjugate, or a pharmaceutically acceptable salt thereof, having a structure provided in Table 1.

TABLE 1

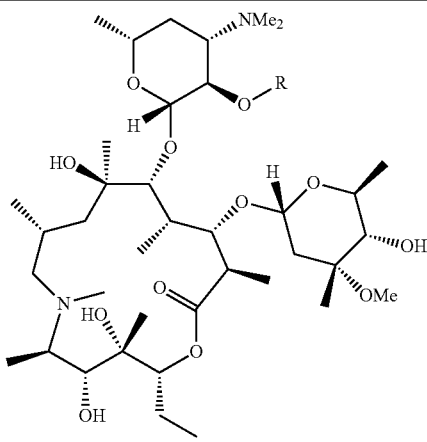

| Chemistry Example | R |
|---|---|
| 1 | —C(O)CH₂OH |

TABLE 1-continued

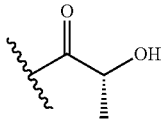

| Chemistry Example | R |
|---|---|
| 2 | 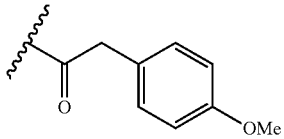 [SMILES: *C(=O)Cc1ccc(OC)cc1] |
| 3 | 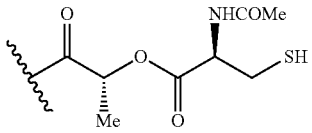 |
| 4 | —C(O)CH$_2$(OCH$_2$CH$_2$)$_4$OH |
| 5 | —C(O)CH$_2$CH$_2$(OCH$_2$CH$_2$)$_4$OH |
| 6 | 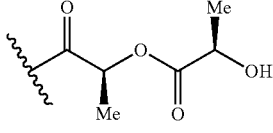 [SMILES: *C(=O)[C@H](C)OC(=O)[C@@H](C)O] |
| 7 | 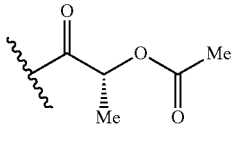 [SMILES: *C(=O)[C@@H](C)OC(C)=O] |
| 8 | 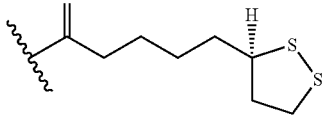 |
| 9 | 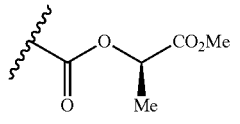 [SMILES: *C(=O)O[C@H](C)C(=O)OC] |

Additional examples having a structure provided in Table 2 were also prepared.

TABLE 2

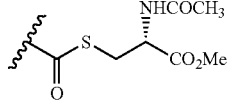

| Chemistry Example | R | R$^{11}$ | R$^{12}$ |
|---|---|---|---|
| 10 | (structure with O-CO$_2$Me, Me) | H | H |
| 11 | H | —C(O)CH$_2$OH | H |
| 12 | H | —C(O)CH$_3$ | H |
| 13 | H | H | —C(O)CH$_3$ |
| 14 | (structure with S, NHCOCH$_3$, CO$_2$Me) | H | H |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the keratolytic conjugate described herein is P. H. Stahl & C. G. Wermuth "Handbook of Pharmaceutical Salts", Verlag Helvetica Chimica Acta, Zurich, 2002.

Pharmaceutical Compositions

In some embodiments, the keratolytic conjugate described herein has a structure provided in Formula (I), Formula (Ia), Formula (I'), Formula (Ia'), or Formula (II). In certain embodiments, the keratolytic conjugate as described herein is administered as a pure chemical. In other embodiments, the keratolytic conjugate described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Provided herein is a pharmaceutical composition comprising at least one keratolytic conjugate, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

In certain embodiments, the keratolytic conjugate as described by any one of Formula (I), Formula (Ia), Formula (I'), Formula (Ia'), or Formula (II), is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

One embodiment provides a pharmaceutical composition comprising a compound of Formula (I), Formula (Ia), Formula (I'), Formula (Ia'), or Formula (II), or a pharmaceutically acceptable salt thereof, and at least one pharmaceutically acceptable excipient. Another embodiment provides the pharmaceutical composition, wherein the pharmaceutical composition is suitable for ophthalmic administration. Another embodiment provides the pharmaceutical composition, wherein the pharmaceutical composition is suitable for topical ophthalmic administration. In some embodiments, topical ophthalmic administration is administration in and/or around the eye, such as to the eyelid margin. In some embodiments, topical ophthalmic administration is administration to the ocular surface and the inner surface to the eyelid.

In some embodiments, the keratolytic conjugate as described by Formula (I), Formula (Ia), Formula (I'), Formula (Ia'), or Formula (II), is formulated as a solution or suspension for topical administration to the eye.

In some embodiments, the keratolytic conjugate as described by Formula (I), Formula (Ia), Formula (I'), Formula (Ia'), or Formula (II), is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one keratolytic conjugate as described herein differ, depending upon the patient's (e.g., human) condition, that is, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. The optimal dose depends upon the body mass, weight, or blood volume of the patient.

In other embodiments, the topical compositions described herein are combined with a pharmaceutically suitable or acceptable carrier (e.g., a pharmaceutically suitable (or acceptable) excipient, physiologically suitable (or acceptable) excipient, or physiologically suitable (or acceptable) carrier). Exemplary excipients are described, for example, in *Remington: The Science and Practice of Pharmacy* (Gennaro, 21$^{st}$ Ed. Mack Pub. Co., Easton, Pa. (2005)).

Methods of Treatment Utilizing Keratolytic Conjugates

One embodiment provides a method of treating an ophthalmic disease or disorder in a patient in need of thereof, comprising administering to the patient a composition comprising a compound, or a pharmaceutically acceptable salt thereof, of Formula (I), Formula (Ia), Formula (I'), Formula (Ia'), or Formula (II). Another embodiment provides the method wherein the pharmaceutical composition is in the form of a solution or suspension suitable for topical ophthalmic administration.

Another embodiment provides the method wherein the ophthalmic disease or disorder is selected from dry eye, lid wiper epitheliopathy (LWE), contact lens discomfort (CLD), contact lens discomfort, dry eye syndrome, evaporative dry eye syndrome, aqueous deficiency dry eye syndrome, blepharitis, keratitis, meibomian gland dysfunction, conjunctivitis, lacrimal gland disorder, inflammation of the anterior surface of the eye, infection of the anterior surface of the eye, infection of the lid, demodex lid infestation, lid wiper epitheliopathy and autoimmune disorder of the anterior surface of the eye.

Described herein are methods for treating ocular surface disorders in a patient in need comprising topical administration of a keratolytic conjugate to the patient. There are two potential categories of administration. One occurs with the assistance of a health-care provider: this category includes both acute and maintenance uses of the keratolytic conjugate. An acute use, in one embodiment, requires a stronger keratolytic conjugate (either in terms of concentration of the agent or the inherent activity of the agent). A maintenance use, in one embodiment, allows for the use of lower concentrations of the agent, or agents with lower inherent activity. A maintenance use, in one embodiment, involves a patient at a routine visit to the health care provider. Both acute uses and maintenance uses optionally involve use of an eye-protecting device or apparatus. In one embodiment, the acute use is performed by the health care provider, and the maintenance use is performed by the patient or non-health care provider. The second potential category of administration does not occur with the active assistance of a health care provider, but rather involves the patient applying the keratolytic conjugate to his/her own eyelid margin. In one embodiment, such administration occurs over an extended period of time; one way of describing this patient-administered multi-administration mode is as a chronic use. In general, different or second formulations of the keratolytic conjugate are recommended for chronic or patient-administered uses. In one embodiment the different or second formulation utilizes a lower concentration of the keratolytic conjugate. In another embodiment, the second or different formulation utilizes a keratolytic conjugate that has a lower activity than the first formulation.

It should be understood that the present methods also include the physical removal of the obstruction in the meibomian gland, followed by chronic and/or maintenance administration of the keratolytic conjugate described herein.

One embodiment provides a method for treating meibomian gland dysfunction in a patient in need thereof, comprising topically administering to the patient a composition comprising a therapeutically-effective amount of at least one keratolytic conjugate in an ophthalmically-acceptable carrier. In some embodiments, the topical administration of the composition comprising a therapeutically-effective amount of at least one keratolytic conjugate in an ophthalmically-acceptable carrier results in enhanced meibum production.

In some embodiments, the topical administration of the composition comprising a therapeutically-effective amount of at least one keratolytic conjugate in an ophthalmically-acceptable carrier occurs until the keratinized obstruction is relieved. In some embodiments, the topical administration of the composition comprising a therapeutically-effective amount of at least one keratolytic conjugate in an ophthalmically-acceptable carrier occurs periodically after relieving of the keratinized obstruction. In some embodiments, the topical administration of the composition comprising a therapeutically-effective amount of at least one keratolytic conjugate in an ophthalmically-acceptable carrier is a single administration. In some embodiments, the topical administration of the composition comprising a therapeutically-effective amount of at least one keratolytic conjugate in an ophthalmically-acceptable carrier is a periodic administration. In some embodiments, the topical administration of the composition comprising a therapeutically-effective amount of at least one keratolytic conjugate in an ophthalmically-acceptable carrier occurs once a day. In some embodiments, the topical administration of the composition comprising a therapeutically-effective amount of at least one keratolytic conjugate in an ophthalmically-acceptable carrier occurs twice a day. In some embodiments, the topical administration of the composition comprising a therapeutically-effective amount of at least one keratolytic conjugate in an ophthalmically-acceptable carrier occurs more than twice a day.

In some embodiments, the composition for topical administration, comprising a therapeutically-effective amount of at least one keratolytic conjugate in an ophthalmically-acceptable carrier is a solution. In some embodiments, the composition for topical administration, comprising a therapeutically-effective amount of at least one keratolytic conjugate in an ophthalmically-acceptable carrier is a solution suitable for topical administration as eye drops. In some embodiments, the composition for topical administration, comprising a therapeutically-effective amount of at least one keratolytic conjugate in an ophthalmically-acceptable carrier is a gel, ocular insert, spray, or other topical ocular delivery method. In some embodiments, the composition for topical administration, comprising a therapeutically-effective amount of at least one keratolytic conjugate in an ophthalmically-acceptable carrier is a semi-solid. In some embodiments, the composition for topical administration, comprising a therapeutically-effective amount of at least one keratolytic conjugate in an ophthalmically-acceptable carrier is homogenous. In some embodiments, the composition for topical administration, comprising a therapeutically-effective amount of at least one keratolytic conjugate in an ophthalmically-acceptable carrier is a dispersion. In some embodiments, the composition for topical administration, comprising a therapeutically-effective amount of at least one keratolytic conjugate in an ophthalmically-acceptable carrier is hydrophilic. In some embodiments, the composition for topical administration, comprising a therapeutically-effective amount of at least one keratolytic conjugate in an ophthalmically-acceptable carrier has an oleaginous base. In some embodiments, the composition for topical administration, comprising a therapeutically-effective amount of at least one keratolytic conjugate in an ophthalmically-acceptable carrier has at least one ophthalmically-acceptable excipient.

One embodiment provides a method for treating MGD in a patient in need thereof comprising topical administration of a composition comprising a keratolytic conjugate. In some embodiments, the topical administration of the composition comprising a keratolytic conjugate occurs once a week. In some embodiments, the topical administration of the composition comprising a keratolytic conjugate occurs twice a week. In some embodiments, the topical administration of the composition comprising a keratolytic conjugate occurs every other day. In some embodiments, the topical administration of the composition comprising a keratolytic conjugate occurs every day. In some embodiments, the topical administration of the composition comprising a keratolytic conjugate occurs several times a day.

In some embodiment, the method comprises treatment in an acute treatment scenario. In another embodiment, the method comprises treatment of a patient naïve to treatment. In another embodiment, the method comprises treatment in a chronic treatment scenario. In another embodiment, the method comprises treatment in a maintenance therapy scenario. In an acute treatment scenario, the administered dosage of keratolytic conjugate may be higher than the administered dosage of keratolytic conjugate employed in a chronic treatment scenario or a maintenance therapy scenario. In an acute treatment scenario, the keratolytic conjugate may be different from the keratolytic conjugate employed in a chronic treatment scenario. In some embodiments, the course of therapy begins in the initial phase of therapy as an acute treatment scenario and later transitions into a chronic treatment scenario or a maintenance therapy scenario. In some embodiments, the meibomian gland opening pharmacological agent administered in the acute treatment scenario is a keratolytic agent and/or keratoplastic agent, and the pharmacological agent administered in the chronic treatment scenario or a maintenance therapy scenario is a keratolytic conjugate.

In certain clinical presentations, patients may require an initial treatment administered by a physician or healthcare professional, to initially open the blockage of the meibomiam gland, such as by placing a more highly concentrated formulation of one of the keratolytic conjugate described herein. In the event the higher concentration formulations are required, the application thereof may require ocular shielding or other activity to minimize the impact of irritation or disruption of the ocular surface or surrounding tissues. Following such a procedure, a patient may be given a different formulation of keratolytic conjugate to take home to apply periodically to the lid margin to maintain the patency of the meibomian gland. Such application may occur twice daily, once a day, weekly or monthly, depending on the formulation activity and the desired product profile of the therapy.

One aspect of the methods of treatment described herein is the location of the topical administration of the composition. In one embodiment, the composition comprising a keratolytic conjugate is administered such that no irritation to eye occurs. In one embodiment, the composition comprising a keratolytic conjugate is administered to the eye lid margin.

One additional embodiment of the methods of treatment described herein is the use of a protective element provided to the eye to avoid irritation to the eye. Although the formulations described herein are generally non-irritating, in some embodiments (e.g., high concentration of agent or when used on a sensitive eye) a protective element provides an additional layer of safety and comfort for the patient. In one embodiment, the composition comprising a keratolytic conjugate is administered while an eye shield is placed on the eye to reduce contact of the pharmacological agent with the cornea and/or conjunctiva such that reduced irritation to eye occurs. In some embodiments, the eye shield is a contact lens or an eye covering. In some embodiments, the eye covering comprises a self-adhesive. In one embodiment, the composition comprising a keratolytic conjugate is administered while the lid is pulled away from the globe to reduce contact of the pharmacological agent with the cornea and/or conjunctiva such that reduced irritation to eye occurs.

EXAMPLES

I. Chemical Synthesis

Solvents, reagents and starting materials were purchased from commercial vendors and used as received unless otherwise described. All reactions were performed at room temperature unless otherwise stated. Starting materials were purchased from commercial sources or synthesised according to the methods described herein or using literature procedures.

Abbreviations

The following abbreviations are used in the Examples and other parts of the description:
$CD_2Cl_2$: Deuterodichloromethane
$CDCl_3$: Deuterochloroform
COMU: (1-Cyano-2-ethoxy-2-oxoethylideneaminooxy)dimethylamino-morpholino-carbenium hexafluorophosphate
DCC: N,N'-Dicyclohexylcarbodiimide
DCM: Dichloromethane
DMF: N,N-Dimethylformamide
$Et_2O$: Diethyl ether
EtOAc: Ethyl acetate
$H_2O$: Water
HPLC: High performance liquid chromatography
MeCN: Acetonitrile
MeOH: Methanol
$MgSO_4$: Magnesium sulfate
mins: Minutes
$NaHCO_3$: Sodium bicarbonate
Rt: Retention time
sat.: Saturated
TBDPS: tert-butyl diphenyl silyl
TEA: Triethylamine
TFA: Trifluoroacetic acid
THF: Tetrahydrofuran
Analytical Methods Method A: Phenomenex Luna C18 (2) 3 μm, 50×4.6 mm; A=water+0.1% formic acid; B=MeCN+0.1% formic acid; 50° C.; % B: 0.0 min 10% 1.2 mL/min, 3.0 min 95% 1.3 mL/min, 3.5 min 97% 1.3 mL/min, 3.51 min 10% 1.5 mL/min, 4.45 min 10% 1.5 mL/min, 4.5 min 10% 1.2 mL/min.

Method B: Waters Sunfire C18 3.5 m, 50×4.6 mm; A=water+0.1% formic acid; B=MeCN; 45° C.; % B: 0.0 min 5% 2.25 mL/min, 1.0 min 37.5% 2.2 mL/min, 3.0 min 95% 2.2 mL/min, 3.5 min 95% 2.3 mL/min, 3.51 min 0% 2.3 mL/min, 4.0 min 0% 2.25 mL/min.

Method C: Waters Sunfire C18 5 m, 100×4.6 mm; A=water+0.1% formic acid; B=MeCN+0.1% formic acid; 45° C.; % B: 0.0 min 5%, 0.50 min 5%, 7.5 min 95%, 10.0 min 95%, 10.1 min 5%, 13.0 min 5%; 1.5 mL/min.

Method D: Phenomenex Luna C18 (2) 3 m, 50×4.6 mm; A=water+0.1% formic acid; B=MeOH+0.1% formic acid; 45° C.; % B: 0.0 min 5% 2.25 mL/min, 1.0 min 37.5% 2.2 mL/min, 3.0 min 95% 2.2 mL/min, 3.5 min 95% 2.3 mL/min, 3.51 min 5% 2.3 mL/min, 4.0 min 5% 2.25 mL/min.

Method E: AnalpH2_MeCN_AZ_25 cm: Phenomenex Luna C18 (2) 5 m, 250×4.6 mm; A=water+0.1% formic acid; B=MeCN; 40° C.; % B: 0.0 min 5% 1.20 mL/min, 0.5 min 5% 1.2 mL/min, 13.0 min 60% 1.2 mL/min, 15 min 95% 1.2 mL/min, 18 min 95% 1.2 mL/min, 18.10 min 5% 1.20 mL/min, 24.0 min 5% 1.2 mL/min.

Method F: AnalpH2_JD2MECN_4MIN: Waters Sunfire C18 3.5 m, 50×4.6 mm; A=water+0.1% formic acid; B=MeCN; 45° C.; % B: 0.0 min 5% 2.25 mL/min, 1.0 min 20% 2.2 mL/min, 3.0 min 50% 2.2 mL/min, 3.25 min 95% 2.2 mL/min, 3.50 min 95% 2.3 mL/min, 3.51 min 100% 2.30 mL/min, 4.0 min 100% 2.25 mL/min.

Chemical Synthesis Example 1

Step 1: Methyl 2-((tert-butyldiphenylsilyl)oxy)acetate

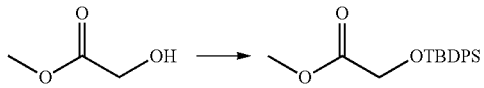

To a stirred solution of methyl glycolate (0.77 mL, 10.0 mmol) in anhydrous DMF (14 mL) were added imidazole (803 mg, 11.8 mmol) and tert-butylchlorodiphenylsilane (3.12 mL, 12.0 mmol) and the mixture stirred at room temperature for 3 hours. The solvent was evaporated in vacuo and the residue diluted with DCM and washed with ice-cold water. The organic layer was dried (MgSO$_4$) and the solvent evaporated in vacuo to give the crude product which was purified by flash chromatography (Biotage SP1; 100 g SNAP cartridge) eluting with isohexane→10% EtOAc-isohexane to yield the title compound as a colourless oil (3.26 g, 99%). LCMS (Method B): Rt=3.50 min; [M+Na]+=351.2. $^1$H-NMR (400 MHz, CDCl$_3$) δ 7.67-7.69 (m, 4H), 7.37-7.43 (m, 6H), 4.24 (s, 2H), 3.68 (s, 3H), 1.09 (t, J=3.0 Hz, 9H)

Step 2: 2-((tert-Butyldiphenylsilyl)oxy)acetic acid

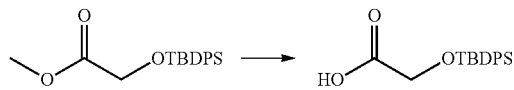

To a stirred solution of methyl 2-((tert-butyldiphenylsilyl)oxy) (1.00 g, 3.04 mmol) in THF (2.75 mL) and water (0.92 mL) was added 0.75 M lithium hydroxide$_{(aq)}$ (4.06 mL, 3.05 mmol) and the mixture stirred at room temperature for 20 hours. The reaction mixture was diluted with water (10 mL) and extracted with Et$_2$O (3×20 mL). The aqueous phase was acidified to pH3 with 5 M HCl$_{(aq)}$ and the solution extracted with EtOAc (3×20 mL). The combined organics were dried (MgSO$_4$), filtered and the solvent evaporated in vacuo. The crude product was purified by flash chromatography (Biotage SP1; 25 g SNAP cartridge) eluting with isohexane→EtOAc to yield the title compound as a colourless oil (0.65 g, 68%). LCMS (Method B): Rt=2.77 mis; [M−H]−=313.3. $^1$H-NMR (400 MHz, CDCl$_3$) δ 7.61-7.66 (m, 4H), 7.39-7.47 (m, 6H), 4.22 (s, 2H), 1.08-1.12 (m, 9H)

Step 3: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 2-((tert-butyldiphenylsilyl)oxy)acetate

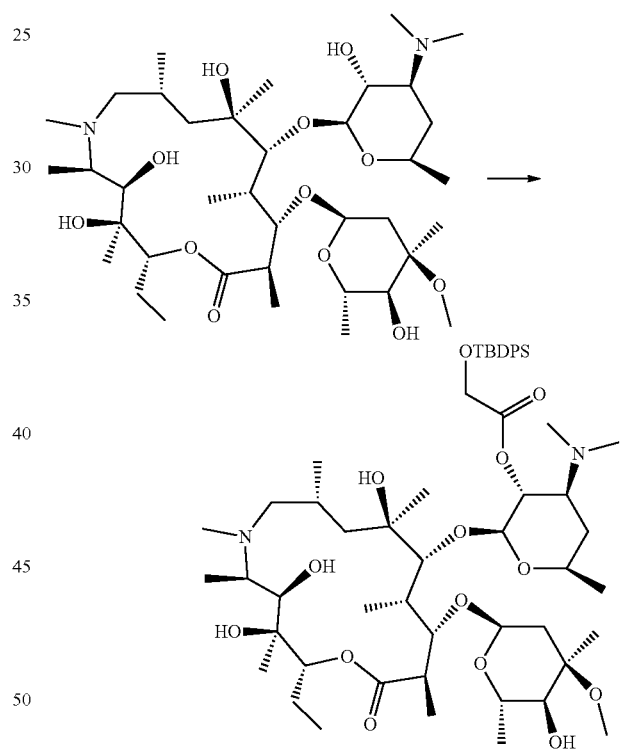

To a solution of 2-((tert-butyldiphenylsilyl)oxy)acetic acid (97 mg, 0.308 mmol) and azithromycin dihydrate (291 mg, 0.370 mmol) in toluene (15 mL) at room temperature was added TEA (155 µL, 1.11 mmol), 4-(dimethylamino)pyridine (286 mg, 2.34 mmol) and 2,4,6-trichlorobenzoyl chloride (162 µL, 1.05 mmol). The mixture was stirred at room temperature for 121 hours. The resulting mixture was diluted with DCM (10 mL), sat. NaHCO$_{3(aq)}$ (10 mL) and H$_2$O (10 mL) and the layers separated. The aqueous phase was extracted with DCM (3×10 mL). The combined organics were dried (MgSO$_4$), filtered, and the solvent evaporated in vacuo. The crude product was purified by flash chromatography (Biotage SP1; 10 g SNAP cartridge) eluting with 4:1 isohexane-acetone (1% TEA)→acetone (1% TEA) and further purified by flash chromatography (Biotage SP1; 10 g SNAP cartridge) eluting with isohexane→acetone (1% TEA). The crude product was then purified by reversed-phase preparative HPLC. Fractions containing product were combined, diluted with DCM and neutralised with sat. NaHCO$_{3(aq)}$. The organic layer was separated and the aqueous phase extracted with DCM. The combined organics were washed with sat. brine solution, dried (MgSO$_4$) and evaporated in vacuo to yield the title compound as a colourless gum (40 mg, 12%). LCMS (Method B): Rt=1.72 min; [M+H]+=1046.0

Step 4: (2S,3R,4S,6R)-4-(Dimethylamino)-2-(((2R, 3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 2-hydroxyacetate

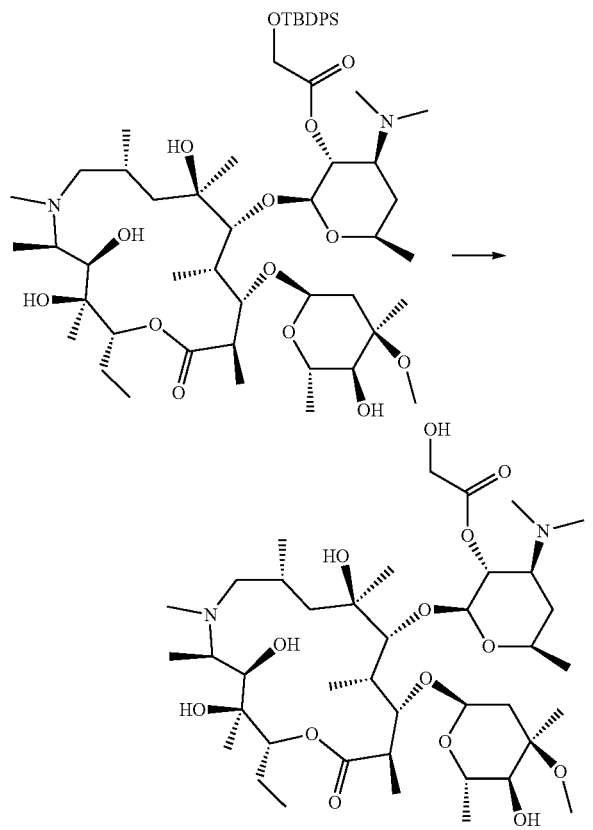

To a stirred solution of (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 2-((tert-butyldiphenylsilyl)oxy)acetate (40 mg, 0.0383 mmol) in anhydrous THF (1 mL) under N$_2$ was added 1 M tetrabutylammonium fluoride hydrate (115 μL, 0.115 mmol) in THF. The reaction was stirred at room temperature for 2 hours then quenched with sat. NaHCO$_{3(aq)}$ and extracted with EtOAc. The organic layer was washed with sat. brine solution and the layers separated. The organic phase was dried (MgSO$_4$), filtered and the solvent evaporated in vacuo. The crude product was purified by flash chromatography (Biotage SP1; 10 g SNAP cartridge) eluting with isohexane (2% TEA)→acetone (2% TEA) to yield the title compound as a white solid (12 mg, 39%). LCMS (Method C): Rt=3.04 min; [M+H]+=807.9

Chemical Synthesis Example 2

The following building block was made by an analogous method to that described above for 2-((tert-butyldiphenylsilyl)oxy)acetic acid.

| Structure | Analytical Data |
|---|---|
| ![HO-C(=O)-CH(OTBDPS)-CH3] | LCMS (Method B): Rt = 2.01 mins; [M − H]− = 327.1 |

Step 1: (2S,3R,4S,6R)-4-(Dimethylamino)-2-(((2R, 3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (R)-2-((tert-butyldiphenylsilyl)oxy)propanoate

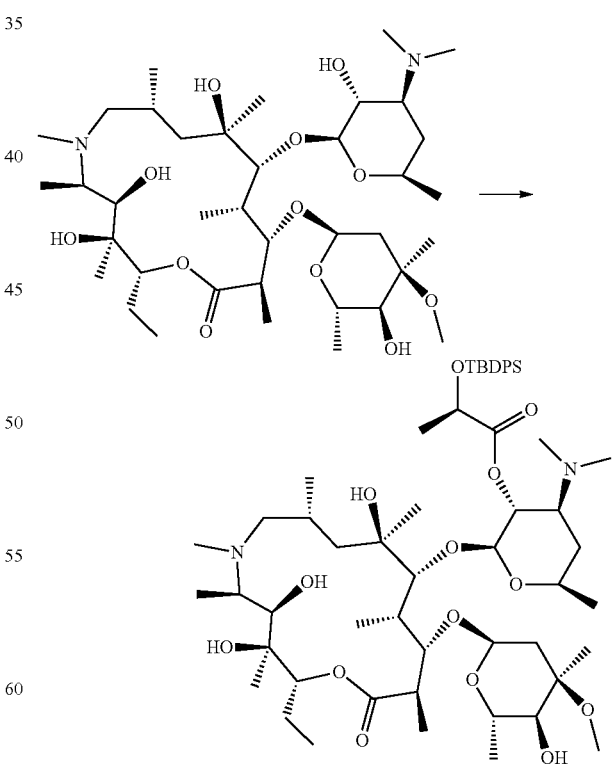

To a stirred solution of (R)-2-((tert-butyldiphenylsilyl)oxy)propanoic acid (361 mg, 1.10 mmol) in DCM (10.7 mL) at 0° C. was added DCC (227 mg, 1.10 mmol) and the mixture allowed to warm to room temperature and stirred for 2 hours. Azithromycin dihydrate (393 mg, 0.500 mmol) was added, and the mixture stirred at room temperature for 112 hours. The resulting mixture was diluted with DCM and sat. NaHCO$_{3(aq)}$ and the layers separated. The organic phase was washed with sat. NaHCO$_{3(aq)}$. The combined aqueous layers were extracted with DCM and the combined organics washed with sat. brine solution, dried (MgSO$_4$), filtered and the solvent evaporated in vacuo. The crude product was purified by flash chromatography (Biotage SP1; 25 g) eluting with isohexane (1% TEA)→acetone (1% TEA) to yield the title compound as a white gum which solidified on standing (149 mg, 28%). LCMS (Method B): Rt=1.93 min; [M+H]+=1059.8

Step 2: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (R)-2-hydroxypropanoate fluoride hydrate (411 μL, 0.411 mmol) in THF. The reaction was stirred at room temperature for 16 hours. The resulting mixture was diluted with sat. NaHCO$_{3(aq)}$ and EtOAc and the layers separated. The organic phase was washed with sat. brine solution, dried (MgSO$_4$), filtered and the solvent evaporated in vacuo. The crude product was purified by reversed-phase preparative HPLC. Fractions containing product were combined, diluted with EtOAc and neutralised with sat. NaHCO$_{3(aq)}$. The organic phase was washed with sat. brine solution, dried (MgSO$_4$), filtered and the solvent evaporated in vacuo. The title compound was obtained as a white solid (12 mg, 11%). LCMS (Method B): Rt=3.18 min; [M+H]+=821.9

Alternatively, Example 2 May be Prepared Via the Following Method:

Step 1: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (R)-2-(benzyloxy)propanoate

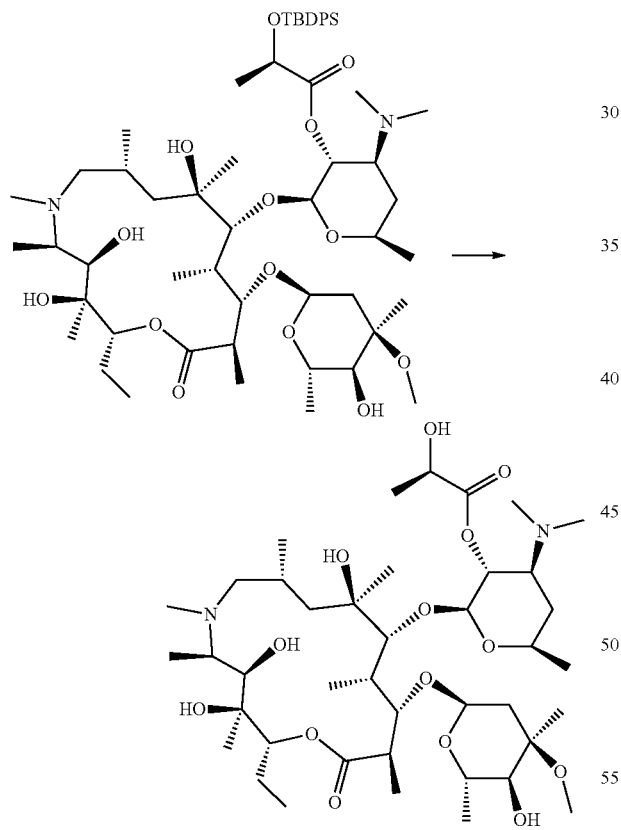

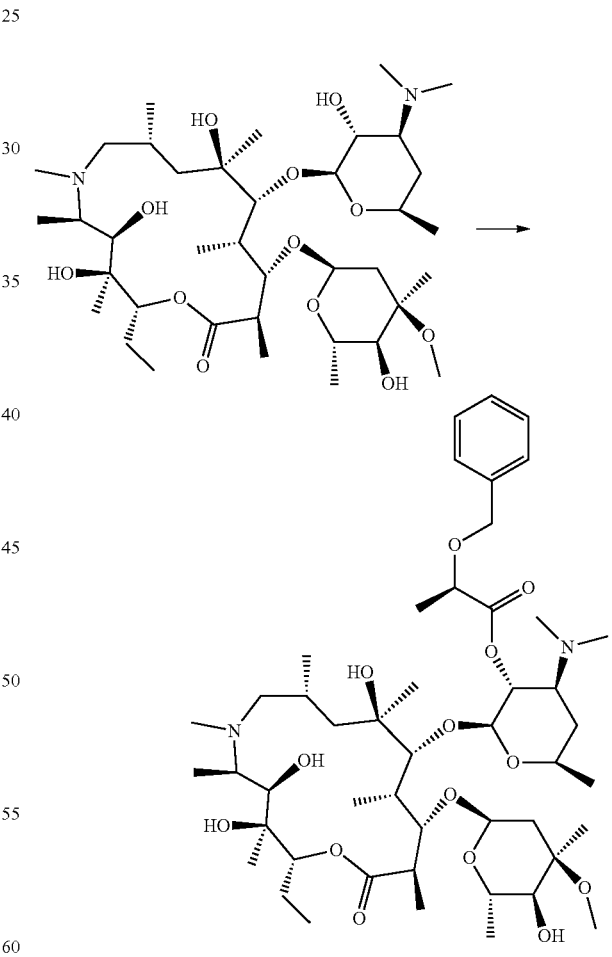

To a stirred solution of (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (R)-2-((tert-butyldiphenylsilyl)oxy)propanoate (145 mg, 0.135 mmol) in anhydrous THF (3.4 mL) at room temperature under N$_2$ was added 1 M tetrabutylammonium To a stirred solution of (R)-(+)-2-benzyloxypropionic acid (115 mg, 0.640 mmol) in anhydrous DCM (25 mL) was added DIPEA (0.83 mL, 4.78 mmol), COMU (1.36 g, 3.18 mmol) and azithromycin dihydrate (500 mg, 0.640 mmol). The mixture was stirred at room temperature for 19 hours. The resulting mixture was diluted with DCM (50 mL) and the solution washed with sat. NaHCO$_{3(aq)}$ (2×20 mL) followed by water (2×20 mL). The organic phase was dried (MgSO$_4$), filtered and the solvent evaporated in vacuo. The crude product was purified by flash chromatography (Biotage SP1; 50 g SNAP cartridge) eluting with isohexane (1% TEA)→acetone (1% TEA) and further purified by flash chromatography (Biotage SP1; 25 g SNAP cartridge) eluting with isohexane (1% TEA)→40% acetone-isohexane (1% TEA) to give the title compound as a yellow gum (424 mg, 73%). LCMS (Method B): Rt=1.55 min; [M+H]+=911.5 Approximately half the material was further purified by flash chromatography (Biotage SP1; 50 g SNAP cartridge) eluting with isohexane (1% TEA)→25% acetone-isohexane (1% TEA) to yield the title compound as a yellow gum (192 mg, 33%). LCMS (Method B): Rt=1.55 min; [M+H]=911.6

Step 2: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (R)-2-hydroxypropanoate

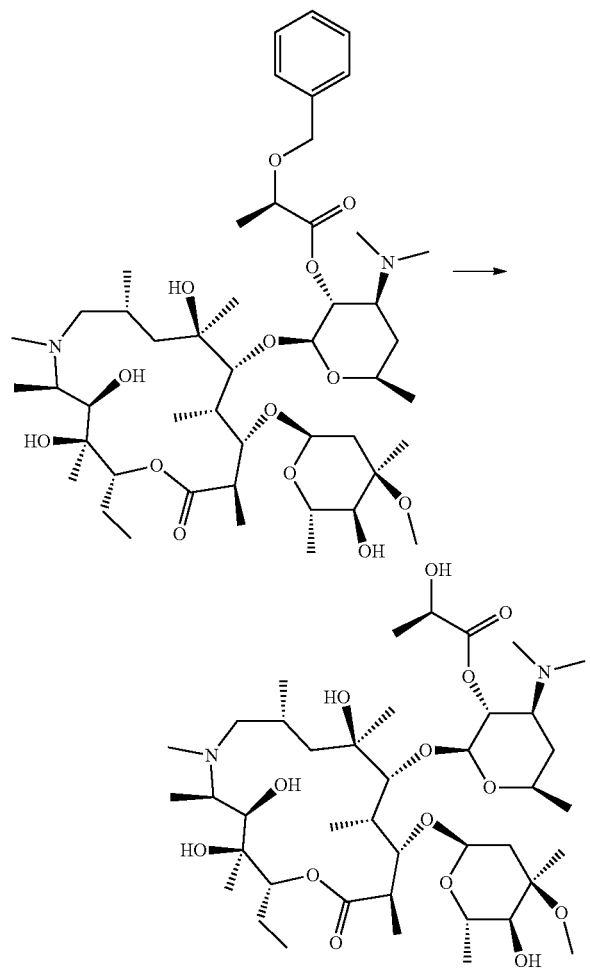

A solution of (2S,3R,4S,6R)-4-(dimethylamino)-2-(((2R,3 S,4R,5R,8R,10R,11R,12S,13 S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (R)-2-(benzyloxy) propanoate (50 mg, 0.060 mmol) in EtOAc (2 mL) was added to a stirred suspension of palladium hydroxide on carbon 20 wt % (11.6 mg, 0.0200 mmol) in EtOAc (0.5 mL) under an atmosphere of nitrogen. The reaction was placed under an atmosphere of hydrogen and stirred for 44 hours. The resulting mixture was diluted with EtOAc and passed through a celite cartridge (2.5 g) washing with EtOAc, the filtrate evaporated in vacuo.

In a separate flask a solution of (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (R)-2-(benzyloxy)propanoate (106 mg, 0.120 mmol) in EtOAc (4 mL) was added to a stirred suspension of palladium 10% wt on carbon (37.1 mg, 0.0300 mmol) in EtOAc (1 mL) under an atmosphere of nitrogen. The reaction was placed under an atmosphere of hydrogen and stirred for 76 h. The resulting mixture was diluted with EtOAc, passed through a celite cartridge, washing with EtOAc, and the filtrate evaporated in vacuo.

The two individual reaction mixtures were combined and the product purified by flash chromatography (Biotage SP1; 10 g SNAP cartridge) eluting with isohexane (1% TEA)→acetone (1% TEA) to yield the title compound as a white solid (58 mg, 41%). LCMS (Method C): Rt=3.21 min; [M+H]=821.9. $^1$H-NMR (400 MHz, CDCl$_3$) δ 5.06 (d, J=4.8 Hz, 1H), 4.59-4.75 (m, 3H), 4.21-4.27 (m, 2H), 4.02 (m, 1H), 3.49-3.68 (m, 3H), 3.21-3.37 (m, 3H), 3.00-3.08 (m, 1H), 2.87 (s, 1H), 2.59-2.73 (m, 3H), 2.30-2.33 (m, 4H), 2.14-2.24 (m, 7H), 1.82-2.07 (m, 4H), 1.66-1.74 (m, 2H), 1.01-1.59 (m, 31H), 0.83-0.91 (m, 10H)

Chemical Synthesis Example 3

(2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-1-yl)oxy)-6-methyltetrahydro-2H-pyran-3-yl 2-(4-methoxyphenyl)acetate

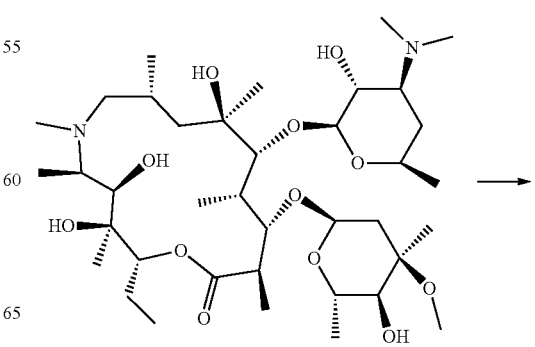

-continued

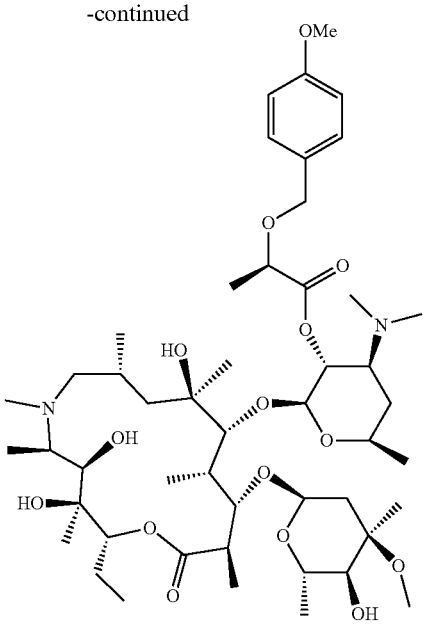

Azithromycin dihydrate (250 mg, 0.3200 mmol) was dissolved in dry DCM (5 mL). 4-Methoxyphenylacetyl chloride (65 µL, 0.425 mmol) and pyridine (50 µL, 0.618 mmol) were added and the mixture stirred at room temperature for 20 hours. The resulting mixture was diluted with DCM (30 mL) and the solution washed with sat. NaHCO$_{3(aq)}$ (40 mL) followed by sat. brine solution (40 mL). The organic phase was dried (MgSO$_4$), filtered and the solvent evaporated in vacuo. The crude product was purified by flash chromatography (Biotage SP1; 10 g SNAP cartridge) eluting with isohexane→3:1 isohexane-acetone (1% TEA) to yield the title compound as a colourless gum, which formed a colourless solid upon scratching (97 mg, 34%). LCMS (Method A): Rt=2.04 min; [M+H]+=897.50. $^1$H-NMR (400 MHz, CD$_2$Cl$_2$) δ 7.12-7.15 (m, 2H), 6.78-6.83 (m, 2H), 4.96 (d, J=4.6 Hz, 1H), 4.63-4.69 (m, 2H), 4.53 (d, J=7.3 Hz, 1H), 4.17-4.27 (m, 1H), 3.92-4.01 (m, 1H), 3.74 (s, 3H), 3.42-3.59 (m, 4H), 3.22-3.36 (m, 3H), 2.95-3.00 (m, 1H), 2.47-2.83 (m, 5H), 2.29-2.34 (m, 4H), 1.79-2.16 (m, 9H), 1.41-1.69 (m, 4H), 1.00-1.37 (m, 26H), 0.80-0.90 (m, 11H)

Chemical Synthesis Example 4

Step 1: 2,2-Dimethyl-3,3-diphenyl-4,7,10,13-tetraoxa-3-silapentadecan-15-ol

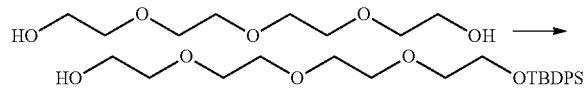

Tetraethylene glycol (889 µL, 5.15 mmol) and imidazole (425 mg, 6.24 mmol) were dissolved in dry DMF (15 mL). tert-Butylchlorodiphenylsilane (1.0 mL, 3.85 mmol) was added dropwise and the mixture stirred at room temperature for 16 hours. The solvent was evaporated in vacuo and the residue dissolved in DCM (50 mL). The solution was washed with sat. brine solution (2×40 mL) and the organic phase evaporated in vacuo. The crude product was purified by flash chromatography (Biotage SP1; 50 g SNAP cartridge) eluting with isohexane→EtOAc to yield the title compound as a colourless oil (767 mg, 46%). $^1$H-NMR (400 MHz, CD$_2$Cl$_2$) δ 7.65-7.68 (m, 4H), 7.34-7.41 (m, 6H), 3.78 (t, J=5.3 Hz, 2H), 3.51-3.64 (m, 14H), 1.02 (s, 9H)

Step 2: Methyl 2,2-dimethyl-3,3-diphenyl-4,7,10,13,16-pentaoxa-3-silaoctadecan-18-oate

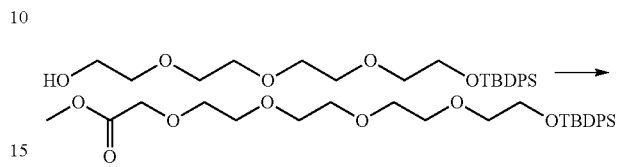

2,2-Dimethyl-3,3-diphenyl-4,7,10,13-tetraoxa-3-silapentadecan-15-ol (755 mg, 1.75 mmol) was dissolved in dry THF (10 mL). Sodium hydride (60% dispersion in oil, 90 mg, 2.25 mmol) was added at room temperature and the mixture stirred at room temperature for 20 minutes. Methyl bromoacetate (250 µL, 2.64 mmol) was added dropwise at room temperature and the mixture stirred at room temperature for 16 hours. The resulting mixture was quenched with MeOH (10 mL) and the solvent evaporated in vacuo. The residue was dissolved in DCM and the solution washed with sat. brine solution (40 mL). The aqueous phase was back extracted with DCM (30 mL) and the combined organics dried (MgSO$_4$), filtered and the solvent evaporated in vacuo. The crude product was purified by flash chromatography eluting with isohexane→60% EtOAc-isohexane to yield the title compound as a colourless oil (327 mg, 37%). $^1$H-NMR (400 MHz, CD$_2$Cl$_2$) δ 7.65-7.67 (m, 4H), 7.34-7.40 (m, 6H), 4.08 (d, J=8.7 Hz, 2H), 3.78 (t, J=5.3 Hz, 2H), 3.68 (s, 2H), 3.54-3.64 (m, 15H), 1.02 (s, 9H)

Step 3: 2,2-Dimethyl-3,3-diphenyl-4,7,10,13,16-pentaoxa-3-silaoctadecan-18-oic acid

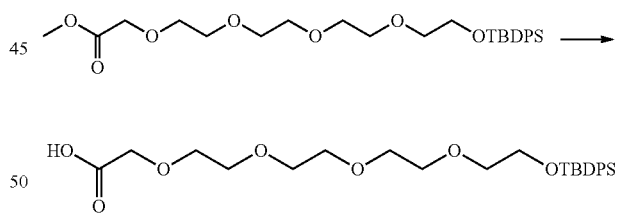

Methyl 2,2-dimethyl-3,3-diphenyl-4,7,10,13,16-pentaoxa-3-silaoctadecan-18-oate (312 mg, 0.620 mmol) was dissolved in 3:1 THF-H$_2$O(8 mL) and the mixture stirred at room temperature for 64 hours. The mixture was acidified to pH 3 (2 N HCl) and the solution extracted with DCM (4×30 mL). The organic phase was dried (MgSO$_4$), filtered and the solvent evaporated in vacuo. The crude product was purified by flash chromatography (Biotage SP1; 10 g SNAP cartridge) eluting with isohexane→DCM→10% MeOH-DCM to reveal the title compound as a colourless oil (101 mg, 34%). LCMS (Method D): Rt=3.72 min (98.3%) [M−H]−=489.3

Step 4: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 2,2-dimethyl-3,3-diphenyl-4,7,10,13,16-pentaoxa-3-silaoctadecan-18-oate Step 5: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 14-hydroxy-3,6,9,12-tetraoxatetradecanoate

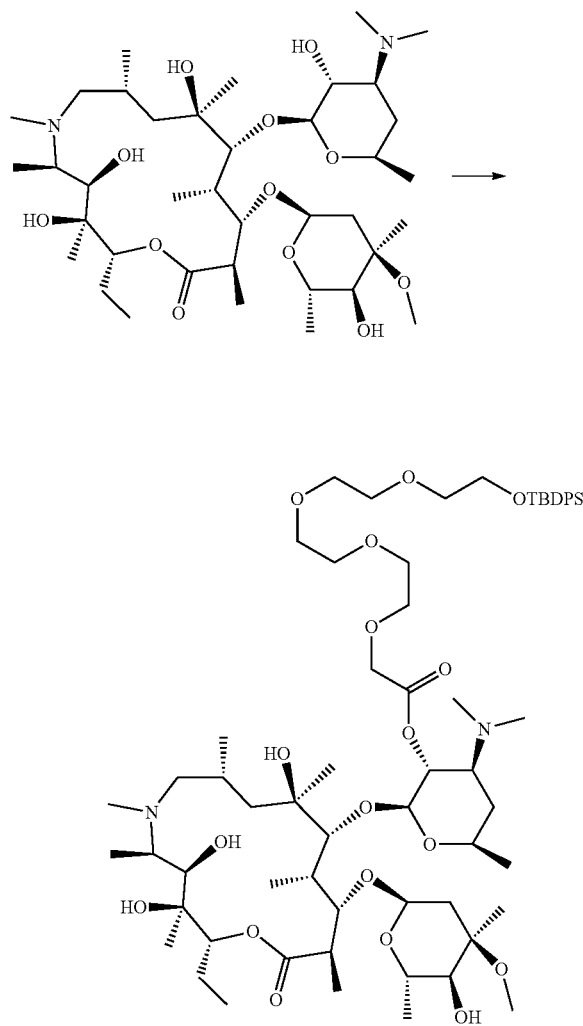

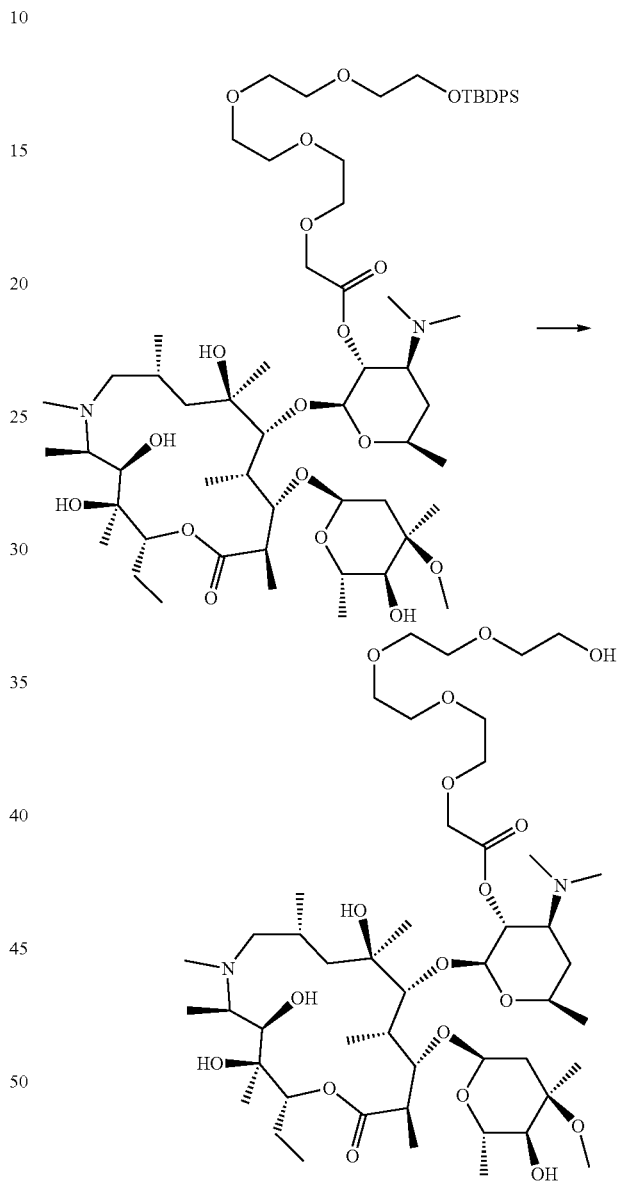

2,2-Dimethyl-3,3-diphenyl-4,7,10,13,16-pentaoxa-3-silaoctadecan-18-oic acid (101 mg, 0.210 mmol) and DCC (45 mg, 0.220 mmol) were dissolved in dry DCM (5 mL). The mixture was stirred at room temperature for 2 hours. Azithromycin dihydrate (120 mg, 0.150 mmol) was added and the mixture stirred at room temperature for 40 hours. The solvent was evaporated in vacuo and the residue dissolved in EtOAc (30 mL). The solution was stored in the freezer for 16 hours and the resulting solution filtered. The solvent was evaporated in vacuo and the residue dissolved in DCM (30 mL). The solution washed with sat. $NaHCO_{3(aq)}$ (20 mL), then dried ($MgSO_4$), filtered and the solvent evaporated in vacuo. The crude product was purified by flash chromatography (Biotage SP1; 10 g SNAP cartridge) eluting with isohexane→3:1 isohexane-acetone (1% TEA) to reveal the title compound as a colourless gum (143 mg, 57%). LCMS (Method D): Rt=2.74 min; [M+H]+=1222.1

(2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 2,2-dimethyl-3,3-diphenyl-4,7,10,13,16-pentaoxa-3-silaoctadecan-18-oate (130 mg, 0.110 mmol) was dissolved in anhydrous THF (5 mL). Tetrabutylammonium fluoride hydrate (1 M in THF, 350 µL, 0.350 mmol) was added and the mixture stirred at room temperature for 2 hours. The resulting mixture was diluted with sat. $NaHCO_{3(aq)}$ (10 mL) and DCM (20 mL)

and the layers separated. The aqueous phase was extracted with DCM (2×20 mL) and the combined organics dried (MgSO$_4$), filtered and the solvent evaporated in vacuo. The crude product was purified by flash chromatography (Biotage SP1; 10 g SNAP cartridge) eluting with isohexane→3:1 isohexane-acetone (1% TEA)→acetone (1% TEA) to yield the title compound as a colourless gum (23 mg, 22%). LCMS (Method C): Rt=3.29 min; [M+H]+=984.0

Chemical Synthesis Example 5

Step 1: tert-Butyl 1-hydroxy-3,6,9,12-tetraoxapentadecan-15-oate

-continued

Tetraethylene glycol (5.0 g, 25.7 mmol) was dissolved in anhydrous THF (60 mL). Sodium hydride (60% dispersion in oil, 52 mg, 1.30 mmol) was added and stirred until gas evolution had stopped. tert-Butyl-acrylate (1.5 mL, 10.2 mmol) was added portion-wise over a 2-hour period and the mixture stirred at room temperature for 2 hours. The mixture was quenched with sat. brine solution (20 mL) and the THF evaporated in vacuo. The residue was dissolved in DCM (60 mL) and the solution washed with sat. brine solution (30 mL). The organic phase was dried (MgSO$_4$), filtered and the solvent evaporated in vacuo. The crude product was purified by flash chromatography eluting with DCM→10% MeOH-DCM to yield the title compound as a pale-yellow oil (2.48 g, 75%). $^1$H-NMR (400 MHz, CDCl$_3$) δ 3.56-3.70 (m, 18H), 2.67 (s, 1H), 2.47 (t, J=6.6 Hz, 2H), 1.41 (s, 9H)

Step 2: tert-Butyl 2,2-dimethyl-3,3-diphenyl-4,7,10,13,16-pentaoxa-3-silanonadecan-19-oate

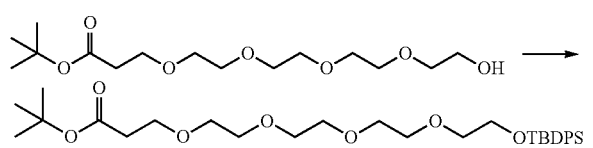

tert-Butyl 1-hydroxy-3,6,9,12-tetraoxapentadecan-15-oate (1.20 g, 3.72 mmol) and imidazole (305 mg, 4.48 mmol) were dissolved in dry DMF (15 mL). tert-Butylchlorodiphenylsilane (1.15 mL, 4.42 mmol) was added dropwise and the mixture stirred at room temperature for 18 hours. The solvent was evaporated in vacuo and the residue partitioned between DCM (60 mL) and sat. brine solution (40 mL). The layers were separated and the organic phase dried (MgSO$_4$), filtered and the solvent evaporated in vacuo. The crude product was purified by flash chromatography (Biotage SP1; 50 g SNAP cartridge) eluting with DCM→5% MeOH-DCM to yield the title compound as a colourless (1.96 g, 94%). $^1$H-NMR (400 MHz, CD$_2$Cl$_2$) δ 7.66-7.68 (m, 4H), 7.35-7.41 (m, 6H), 3.78 (t, J=5.0 Hz, 2H), 3.64 (t, J=6.4 Hz, 2H), 3.54-3.59 (m, 14H), 2.43 (t, J=6.4 Hz, 2H), 1.41 (s, 9H), 1.02 (s, 9H)

Step 3: 2,2-Dimethyl-3,3-diphenyl-4,7,10,13,16-pentaoxa-3-silanonadecan-19-oic acid

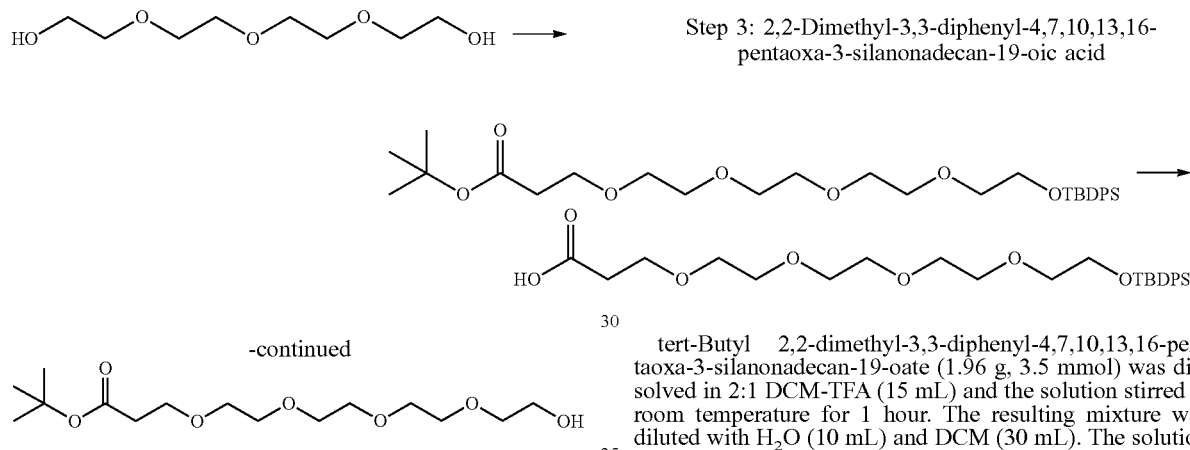

tert-Butyl 2,2-dimethyl-3,3-diphenyl-4,7,10,13,16-pentaoxa-3-silanonadecan-19-oate (1.96 g, 3.5 mmol) was dissolved in 2:1 DCM-TFA (15 mL) and the solution stirred at room temperature for 1 hour. The resulting mixture was diluted with H$_2$O (10 mL) and DCM (30 mL). The solution was stirred vigorously to mix the phases and the solution basified to pH 3 with 2 M NaOH. The layers were separated and the aqueous phase extracted with DCM (30 mL). The combined organics were evaporated in vacuo and the crude product purified by flash chromatography (Biotage SP1; 50 g SNAP cartridge) eluting with DCM→10% MeOH-DCM to yield the title compound as a colourless oil (0.926 g, 52%). $^1$H-NMR (400 MHz, CD$_2$Cl$_2$) δ 7.63-7.69 (m, 4H), 7.34-7.40 (m, 6H), 3.78 (t, J=5.0 Hz, 2H), 3.70 (t, J=6.0 Hz, 2H), 3.54-3.62 (m, 14H), 2.54 (t, J=6.0 Hz, 2H), 0.99-1.04 (m, 9H)

Step 4: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 2,2-dimethyl-3,3-diphenyl-4,7,10,13,16-pentaoxa-3-silanonadecan-19-oate

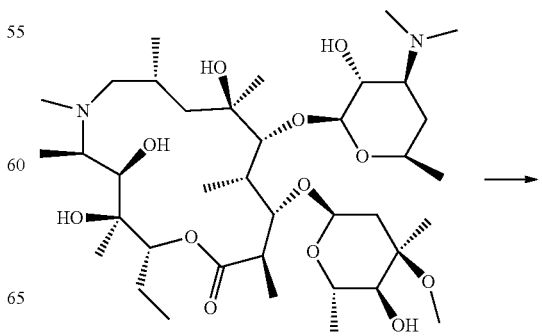

63

-continued

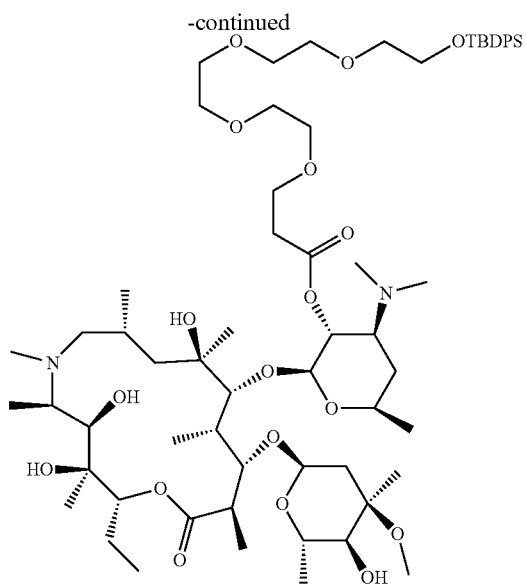

2,2-Dimethyl-3,3-diphenyl-4,7,10,13,16-pentaoxa-3-silanonadecan-19-oic acid (82 mg, 0.160 mmol), azithromycin dihydrate (105 mg, 0.130 mmol) and COMU (280 mg, 0.650 mmol) were dissolved in anhydrous DCM (5 mL). DIPEA (175 µL, 1.00 mmol) was added and the mixture stirred at room temperature for 20 hours. The resulting mixture was diluted with DCM (50 mL) and the solution washed with sat. NaHCO$_{3(aq)}$ (2×50 mL). The organic phase was dried (MgSO$_4$), filtered and the solvent evaporated in vacuo. The crude product was purified by flash chromatography (Biotage SP1; 10 g SNAP cartridge) eluting with isohexane→3:1 isohexane-acetone (1% TEA) to yield the title compound as a pale-yellow gum (119 mg, 59%). LCMS (Method D): Rt=2.72 min; [M+H]=1236.1

Step 5: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 1-hydroxy-3,6,9,12-tetraoxapentadecan-15-oate

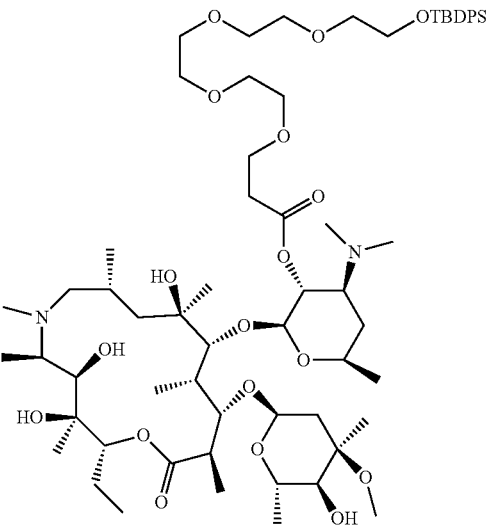

64

-continued (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 2,2-dimethyl-3,3-diphenyl-4,7,10,13,16-pentaoxa-3-silanonadecan-19-oate (57 mg, 0.050 mmol) was dissolved in anhydrous THF (5 mL). Tetrabutylammonium fluoride hydrate (1 M in THF, 155 µL, 0.155 mmol) was added and the mixture stirred at room temperature for 2 hours. The resulting mixture was quenched with sat. NaHCO$_{3(aq)}$ (10 mL) and the solution extracted with DCM (2×25 mL). The combined organics were dried (MgSO$_4$), filtered and the solvent evaporated in vacuo. The crude product was purified by flash chromatography (Biotage SP1; 10 g SNAP cartridge) eluting with isohexane→3:1 isohexane-acetone (1% TEA)→acetone (1% TEA) to yield the title compound as an off-white gum which solidified upon scratching (36 mg, 78%). LCMS (Method D): Rt=1.87 min; [M+H]+=998.0

Chemical Synthesis Example 6

Step 1: (R)-1-(tert-Butoxy)-1-oxopropan-2-yl N-acetyl-S-(bis(4-methoxyphenyl)(phenyl)methyl)-L-cysteinate

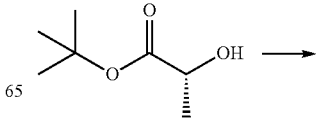

-continued

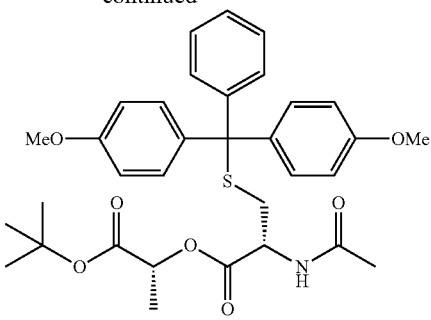

N-Acetyl-S-(bis(4-methoxyphenyl)(phenyl)methyl)-L-cysteine (800 mg, 1.72 mmol), tert-butyl (2S)-2-hydroxypropanoate (260 mg, 1.78 mmol) and triphenylphosphine (680 mg, 2.59 mmol) were dissolved in anhydrous DCM (20 mL). Diisopropyl azodicarboxylate (500 µL, 2.55 mmol) was added drop-wise and the mixture stirred at r.t. for 3 hours. The solvent was evaporated in vacuo and the crude product purified by flash chromatography eluting with iso-hexane→1:1 EtOAc-isohexane to yield (R)-1-(tert-butoxy)-1-oxopropan-2-yl N-acetyl-S-(bis(4-methoxyphenyl)(phenyl)methyl)-L-cysteinate (1.06 g, 104%) as an off-white solid. LCMS (Method D): Rt=3.59 mins; [M+Na]+=616.2

Step 2: (R)-2-((Acetyl-L-cysteinyl)oxy)propanoic acid

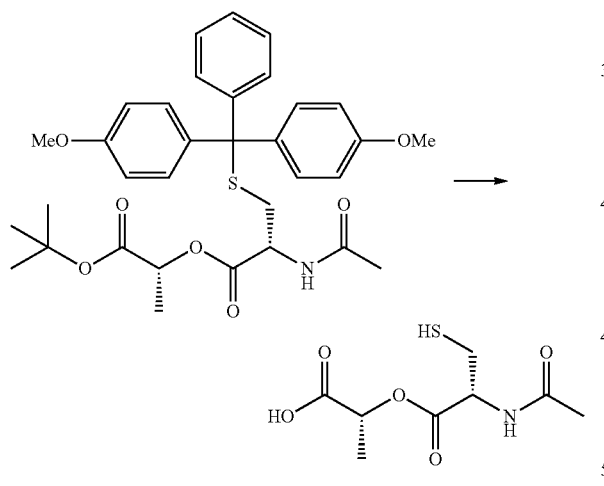

(R)-1-(tert-Butoxy)-1-oxopropan-2-yl N-acetyl-S-(bis(4-methoxyphenyl)(phenyl)methyl)-L-cysteinate (1.06 g, 1.79 mmol) was dissolved in DCM (10 mL) and TFA (10 mL). Triethylsilane (1000 µL, 6.26 mmol) was added and the mixture stirred at r.t. for 3 hours. TFA (2 mL) was added and the mixture stirred at r.t. for 30 minutes. The solvent was evaporated in vacuo. The residue was dissolved in DCM (30 mL) and the solvent evaporated in vacuo. Approximately 10% of the crude residue was purified by reversed-phase HPLC. Fractions containing desired product were combined and the solution frozen (−78° C.). The solvent was then evaporated by lyophilisation to yield (R)-2-((Acetyl-L-cysteinyl)oxy)propanoic acid (13 mg, 31%) as a white solid. $^1$H-NMR (400 MHz, MeOD) δ 5.18-4.98 (m, 1H), 4.77-4.62 (m, 1H), 3.08-2.75 (m, 2H), 2.15-1.89 (m, 3H), 1.62-1.38 (m, 3H)

Step 3: (R)-2-((N-Acetyl-S-(bis(4-methoxyphenyl)(phenyl)methyl)-L-cysteinyl)oxy)propanoic acid

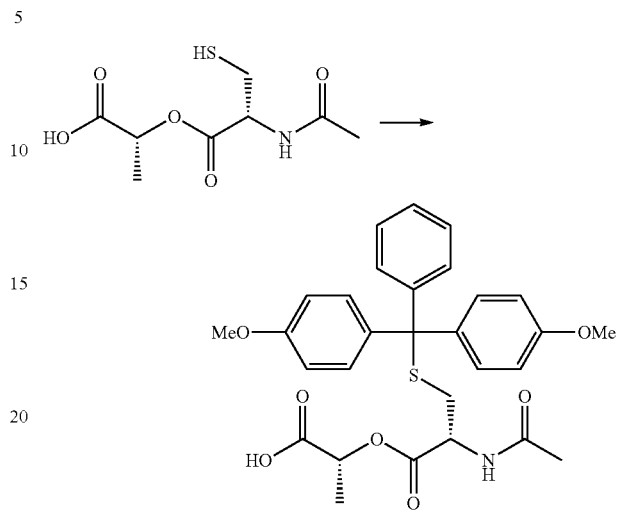

(R)-2-((Acetyl-L-cysteinyl)oxy)propanoic acid (900 mg, 0.910 mmol) and 4,4'-Dimethoxytrityl chloride (280 mg, 0.826 mmol) were dissolved in anhydrous DCM (20 mL). TEA (0.50 mL, 3.59 mmol) was added and the mixture stirred at r.t. for 2 hours. The mixture was diluted with DCM (40 mL) and the solution washed with sat. $NH_4Cl_{(aq)}$ (40 mL). The organic phase was dried ($MgSO_4$), filtered and the solvent evaporated in vacuo. The crude product was purified by flash chromatography (Biotage SP1; 25 g SNAP cartridge) eluting with EtOAc→20% MeOH-EtOAc to yield (R)-2-((N-acetyl-S-(bis(4-methoxyphenyl)(phenyl)methyl)-L-cysteinyl)oxy)propanoic acid (403 mg, 82%) as a pale pink solid. LCMS (Method D): Rt=3.52 mins; [M−H]−=536.2

Step 4: (R)-1-(((2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-1-oxopropan-2-yl N-acetyl-S-(bis(4-methoxyphenyl)(phenyl)methyl)-L-cysteinate

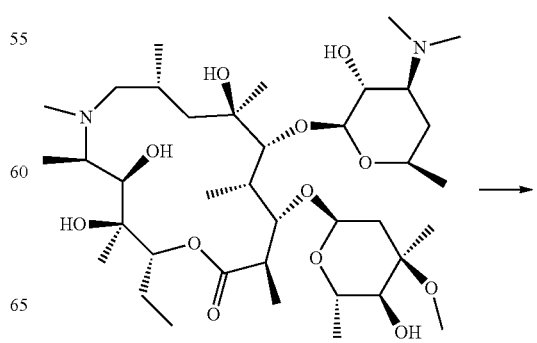

-continued

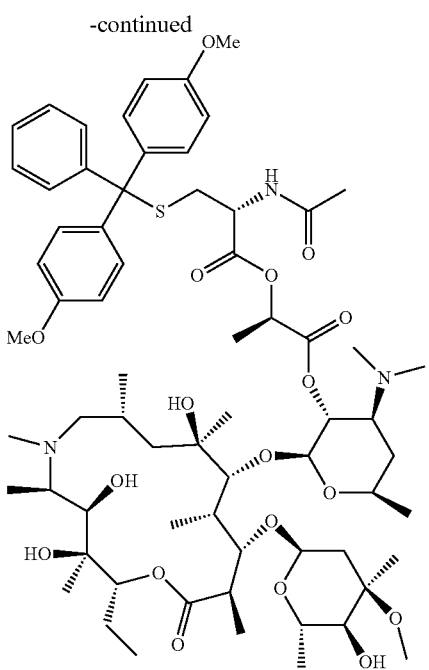

Azithromycin dihydrate (280 mg, 0.357 mmol), (R)-2-((N-acetyl-S-(bis(4-methoxyphenyl)(phenyl)methyl)-L-cysteinyl)oxy)propanoic acid (200 mg, 0.372 mmol) and TCFH (350 mg, 1.25 mmol) were dissolved in anhydrous DCE (10 mL). DIPEA (400 µL, 2.30 mmol) was added and the mixture stirred at 40° C. for 3 hours. The mixture was diluted with DCM (30 mL) and the solution washed successively with sat. $NH_4Cl_{(aq)}$ (2×30 mL), $H_2O$ (20 mL) and sat. brine solution (20 mL). The organic phase was dried ($MgSO_4$), filtered and the solvent evaporated in vacuo. The crude product was purified by flash chromatography (Biotage SP1; 10 g SNAP cartridge) eluting with isohexane→3:1 isohexane-acetone (1% TEA) to yield (R)-1-(((2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-1-oxopropan-2-yl N-acetyl-S-(bis(4-methoxyphenyl)(phenyl)methyl)-L-cysteinate (220 mg, 49%) as an off-white solid. LCMS (Method D): Rt=2.62 mins; [M+H]+=1269.2

Step 5: (R)-1-(((2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-1-oxopropan-2-yl acetyl-L-cysteinate

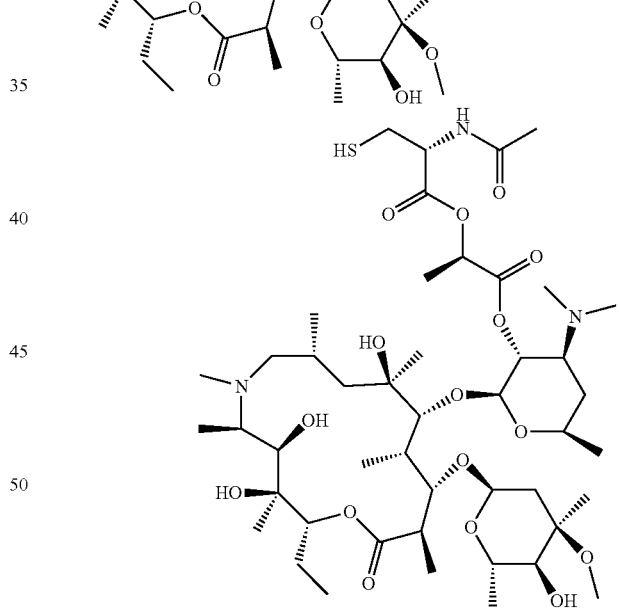

(R)-1-(((2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-1-oxopropan-2-yl N-acetyl-S-(bis(4-methoxyphenyl)(phenyl)methyl)-L-cysteinate (75 mg, 0.0591 mmol) was dissolved in anhydrous DCM (8 mL). Formic acid (900 µL) and triethylsilane (40 µL, 0.250 mmol) were added and the mixture stirred at r.t. for 2 hours. Formic acid (100 µL) was added and the mixture stirred at r.t. for 30 minutes. The mixture was diluted with isohexane (50 mL) and water (30 mL) and the layers separated. The aqueous phase was washed successively with 9:1 isohexane-DCM (50 mL) and DCM (3×30 mL). The aqueous phase was basified to pH4 and the solution then extracted with DCM (3×30 mL), the combined organics were dried, filtered and the solvent evaporated in vacuo to yield (R)-1-(((2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)-1-oxopropan-2-yl acetyl-L-cysteinate (14 mg, 25%) as a pale yellow solid. LCMS (Method D): Rt=1.98 mins; [M+H]+=967.0

Chemical Synthesis Example 7

Step 1: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl(S)-2-(((R)-2-(benzyloxy)propanoyl)oxy)propanoate

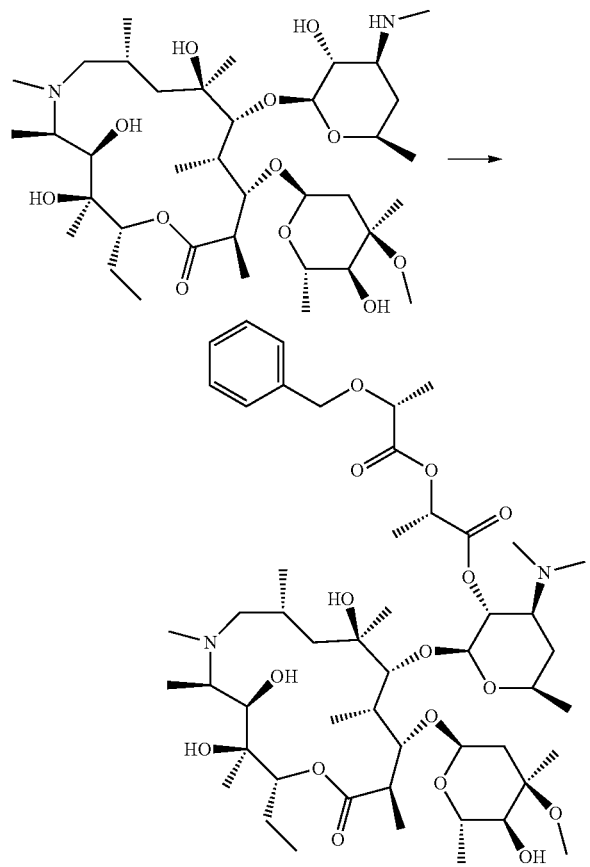

To a stirred solution of (R)-(+)-2-benzyloxypropionic acid (72.1 mg, 0.400 mmol) and DIPEA (70 μL, 0.400 mmol) in anhydrous DCM (4 mL) was added COMU (171 mg, 0.400 mmol) and the resulting mixture stirred at r.t. for 5 minutes followed by the addition of L-(+)-lactic acid (30 μL, 0.400 mmol). The mixture was stirred at r.t. for 30 minutes. DIPEA (120 μL, 0.700 mmol), COMU (214 mg, 0.500 mmol) and azithromycin dihydrate (157 mg, 0.200 mmol) were added and the mixture stirred at r.t. for 4 hours. The mixture was diluted with DCM and sat. NaHCO₃ solution and the layers separated. The organic phase was washed successively with H₂O and sat. brine solution, dried (MgSO₄), filtered and the solvent evaporated in vacuo. The residue was partitioned between Et₂O/EtOAc and H₂O and the layers separated. The organic phase was washed with sat. brine solution, dried (MgSO₄), filtered and the solvent evaporated in vacuo. The crude product was purified by flash chromatography (Biotage SP1; 10 g SNAP cartridge) eluting with isohexane→20% acetone-isohexane (1% TEA) to yield (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (S)-2-(((R)-2-(benzyloxy)propanoyl)oxy)propanoate as a colourless gum (125 mg, 64%). LCMS (Method F): Rt=2.48 mins; [M+H]+=983.8

Step 2: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl(S)-2-(((R)-2-hydroxypropanoyl)oxy)propanoate

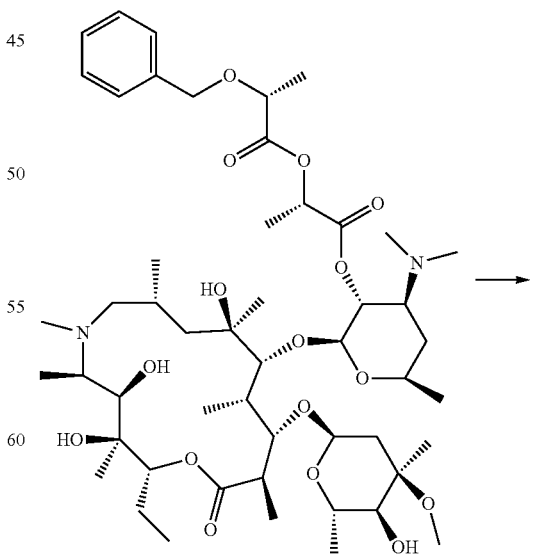

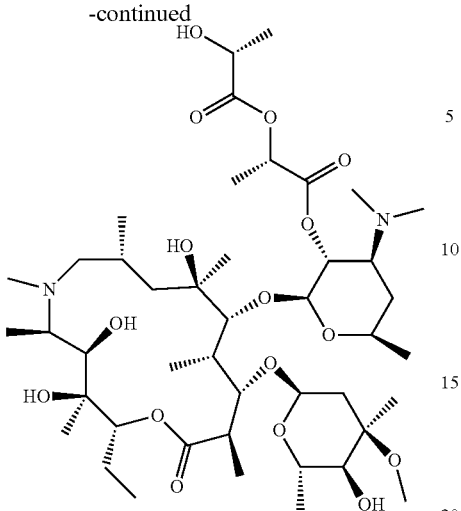

A stirred mixture of (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (S)-2-(((R)-2-(benzyloxy)propanoyl)oxy)propanoate (125 mg, 0.130 mmol), palladium 10% wt on carbon (67.7 mg, 0.0600 mmol) and ammonium formate (80.2 mg, 1.27 mmol) in EtOAc (3.5 mL) was heated at 50° C. for 1 h. The reaction mixture was diluted with EtOAc and filtered through celite, washing with EtOAc, the resulting filtrate was evaporated in vacuo. The crude product was purified by flash chromatography (Biotage SP1; 10 g SNAP cartridge) eluting with isohexane→acetone (1% TEA) to yield (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (S)-2-(((R)-2-hydroxypropanoyl)oxy)propanoate (38 mg, 33%) as a colourless gum. LCMS (Method E): Rt=7.95 mins; [M+H]+=894.0

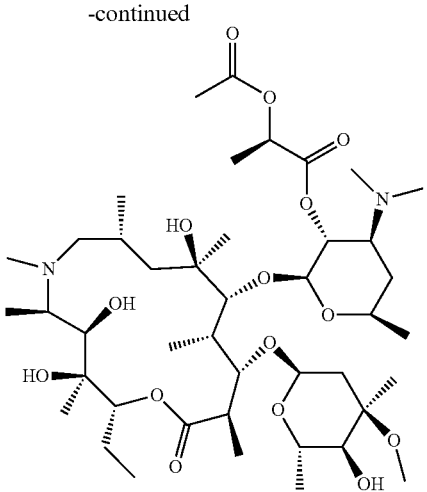

To a stirred solution of (R)-(+)-2-acetoxypropionic acid (45 µL, 0.401 mmol) in anhydrous DCE (8 mL) was added DIPEA (240 µL, 1.40 mmol), azithromycin dihydrate (315 mg, 0.401 mmol) and COMU (430 mg, 1.00 mmol). The solution was stirred at 60° C. for 1 hour. The solvent was evaporated in vacuo and the resulting residue dissolved in DCM. The solution was washed successively with sat. NaHCO$_{3(aq)}$ (20 mL), H$_2$O (20 mL) and sat. brine solution (20 mL). The organic phase was dried (MgSO$_4$), filtered and the solvent evaporated in vacuo. The crude reaction mixture was dissolved in EtOAc and diluted with Et$_2$O (60 mL) and washed successively with sat. NaHCO$_{3(aq)}$, H$_2$O and sat. brine solution. The organic phase was dried (MgSO$_4$), filtered and the solvent evaporated in vacuo. The crude product was purified by flash chromatography eluting with isohexane→acetone (1% TEA) to yield (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (R)-2-acetoxypropanoate (140 mg, 40%) as a pale yellow solid. LCMS (Method E): Rt=8.32 mins; [M+H]+=863.8

Chemical Synthesis Example 8

Step 1: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (R)-2-acetoxypropanoate Chemical Synthesis Example 9

Step 1: (2S,3R,4S,6R)-4-(Dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl 5-((R)-1,2-dithiolan-3-yl)pentanoate

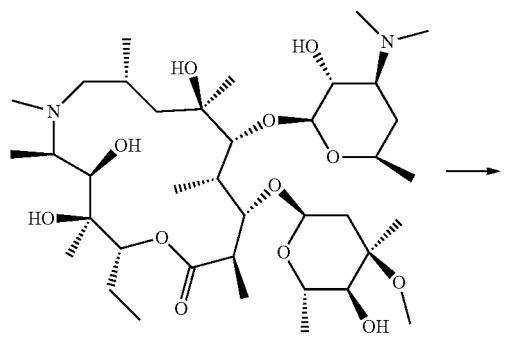

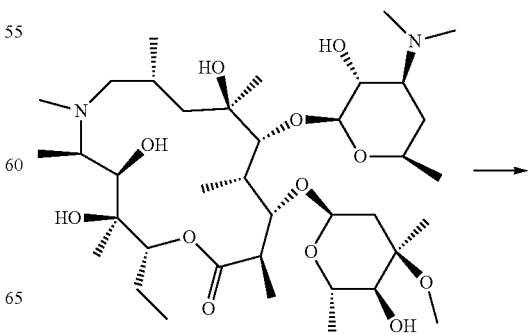

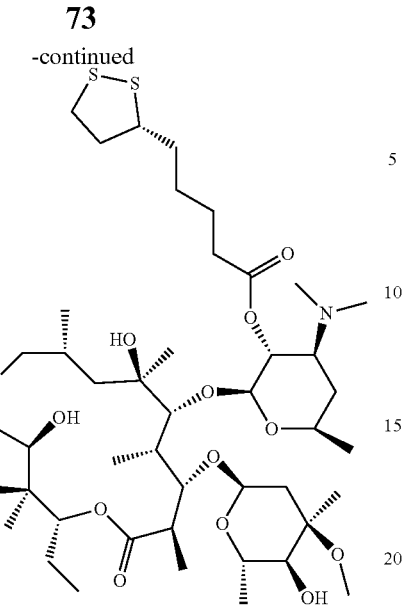
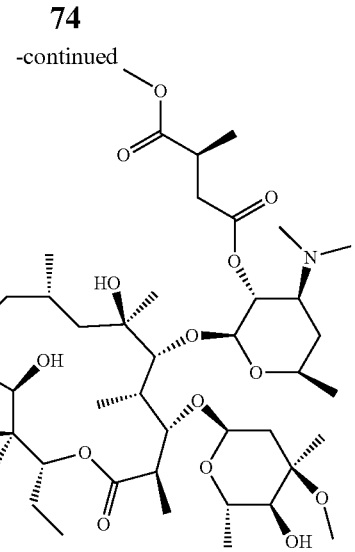

Azithromycin dihydrate (120 mg, 0.153 mmol), lipoic acid (40 mg, 0.194 mmol) and COMU (230 mg, 0.537 mmol) were dissolved in anhydrous DCE (5 mL). DIPEA (150 μL, 0.861 mmol) was added and the mixture stirred at 40° C. for 18 hours. The mixture was diluted with DCM (50 mL) and the solution washed with sat. $NH_4Cl$(aq) (3×40 mL), $H_2O$ (30 mL) and sat. brine solution (30 mL). The solution was dried ($MgSO_4$), filtered and the solvent evaporated in vacuo. The sample flask was purged with $N_2$, sealed and stored in the freezer for 60 hours. The crude product was purified by flash chromatography (Biotage SP1; 10 g SNAP cartridge) eluting with isohexane→1:1 isohexane-EtOAc to yield [(2S,3R,4S,6R)-4-(dimethylamino)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-tetrahydropyran-2-yl]oxy-3,5,6,8,10,12,14-heptamethyl-15-oxo-1-oxa-6-azacyclopentadec-11-yl]oxy]-6-methyl-tetrahydropyran-3-yl]5-[(3R)-dithiolan-3-yl]pentanoate (39 mg, 27%) as a yellow sticky solid.

LCMS (DMX133_A021219-144_: Rt=2.31 mins (>95%) [M+H]+=937.8. LCMS (Method B): Rt=2.31 mins; [M+H]+=937.8

Chemical Synthesis Example 10

Step 1: Methyl (R)-2-(((((2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)carbonyl)oxy)propanoate

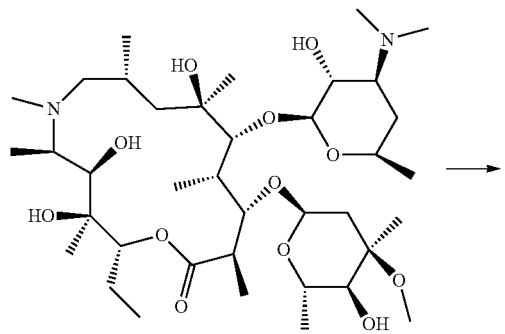

To a stirred solution of azithromycin dihydrate (200 mg, 0.255 mmol) in anhydrous DMF (2 mL) at 0° C. under an atmosphere of $N_2$ was added DIPEA (270 μL, 1.53 mmol) and 1-chloroethyl chloroformate (330 μL, 0.306 mmol). The mixture was stirred at 0° C. for 5 min. (R)-Methyl 2-hydroxypropanoate (240 μL, 0.255 mmol) was added and the reaction heated at 55° C. for 1 h. The reaction mixture was allowed to stand at r.t. for 64 hours. The mixture was diluted with DCM and washed with sat. $NH_4Cl_{(aq)}$ (2×10 mL) and the layers separated. The aqueous phase was extracted with DCM (10 mL) and the combined organics washed successively with 1:1 $H_2O$/sat. brine solution (40 mL) and sat. brine solution (10 mL), dried ($MgSO_4$), filtered and the solvent evaporated in vacuo. The residue was dissolved in DCM and purified by flash column chromatography (Biotage SP1; 10 g SNAP cartridge) eluting with isohexane→acetone (1% TEA). The crude product was further purified by flash chromatography (Biotage SP1; 10 g SNAP cartridge) eluting with isohexane→6:4 acetone-isohexane (1% TEA). The crude product was further purified by reversed-phase HPLC, fractions containing desired product were combined and extracted with DCM. The combined organics were washed successively with $H_2O$ and sat. brine solution, dried ($MgSO_4$) filtered and the solvent evaporated in vacuo to yield methyl (R)-2-(((((2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)carbonyl)oxy)propanoate as a white solid (2 mg, 1%). LCMS (Method B): Rt=1.49 mins; [M+H]+=879.7

Chemical Synthesis Example 11

Step 1: (2S,3R,4S,6R)-4-(Dimethylamino)-2-(((2R, 3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl acetate Step 2: (2R,3R,4R,5R,8R,10R,11R,12S,13S,14R)-11-(((2S,3R,4S,6R)-3-Acetoxy-4-(dimethylamino)-6-methyltetrahydro-2H-pyran-2-yl)oxy)-2-ethyl-3,10-dihydroxy-3-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-4-yl 2-(benzyloxy)acetate

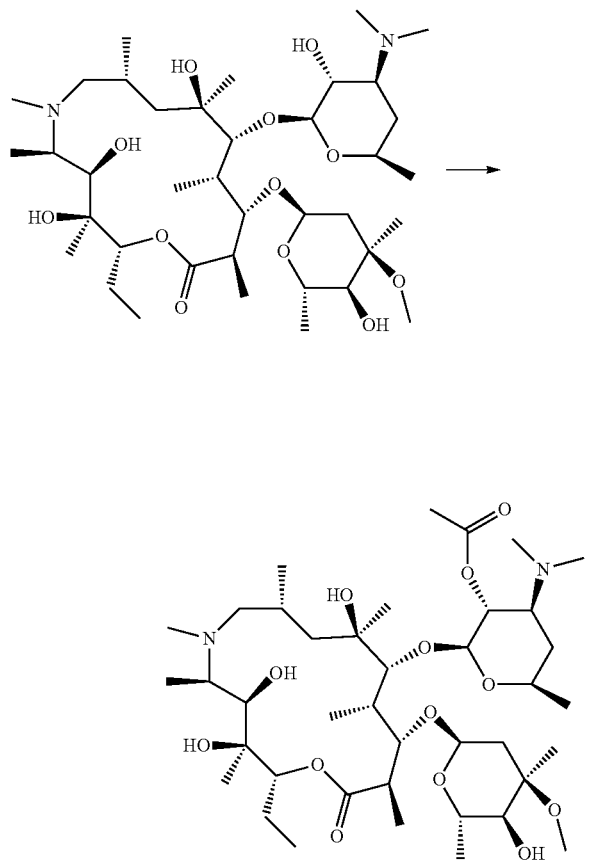

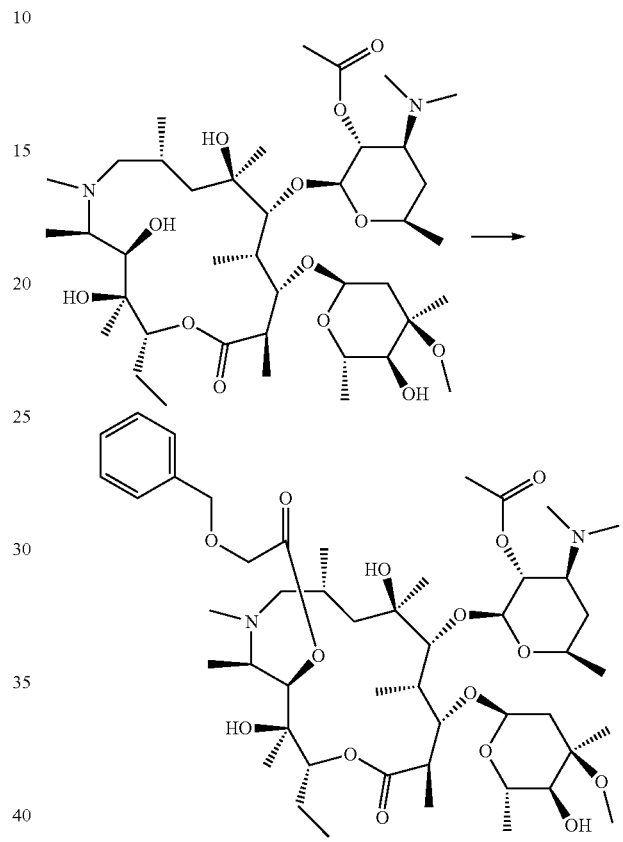

A solution of acetic anhydride (260 µL, 2.75 mmol) in anhydrous DCM (5 mL) was added drop-wise to a stirred solution of azithromycin dihydrate (2.00 g, 2.55 mmol) and pyridine (210 µL, 2.60 mmol) in anhydrous DCM (20 mL). The mixture was stirred at r.t. for 3 hours. Acetic anhydride (80 µL, 0.846 mmol) was added drop-wise over 5 minutes and the mixture stirred at r.t. for 1.5 hours. The mixture was diluted with DCM (40 mL) and the solution washed successively with saturated $NH_4Cl_{(aq)}$ (2×40 mL), $H_2O$ (2×20 mL), saturated $NaHCO_{3(aq)}$ (40 mL) and sat. brine solution (40 mL). The organic phase was dried ($MgSO_4$), filtered and the solvent evaporated in vacuo to yield (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl acetate (1.15 g, 57%) as a pale yellow solid. LCMS (Method D): Rt=1.93 mins; [M+H]+=791.9.

Benzyloxyacetic acid (65 mg, 0.390 mmol) was dissolved in anhydrous DCM (5 mL). Oxalyl chloride (140 µL, 1.63 mmol) was added followed by anhydrous DMF (100 µL) and the mixture stirred at r.t. for 1.5 hours. The solvent was evaporated in vacuo and the residue dissolved in DCM (10 mL). The solvent was evaporated in vacuo and the residue dissolved in anhydrous DCM (5 mL). (2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl acetate (200 mg, 0.250 mmol) and pyridine (10 µL, 0.120 mmol) were added and the mixture stirred at r.t. for 1 hour, followed by reflux for 1 hour. Benzyloxyacetic acid (42 mg, 0.253 mmol) was dissolved in anhydrous DCM (5 mL). Oxalyl chloride (90 µL, 1.05 mmol) was added followed by anhydrous DMF (100 µL) and the mixture stirred at room temperature for 1.5 hours. The solvent was evaporated in vacuo and the residue dissolved in DCM (10 mL). The solvent was evaporated in vacuo. Anhydrous DCM (2 mL) and anhydrous pyridine (100 µL, 0.120 mmol) were added and the solution added to the reaction mixture and stirred at reflux for 1.5 hours. TEA (90 µL, 0.650 mmol) was added and the mixture stirred at reflux for 1.5 hours.

Benzyloxyacetic acid (42 mg, 0.253 mmol) was dissolved in anhydrous DCM (5 mL). Oxalyl chloride (90 µL, 1.05 mmol) was added followed by anhydrous DMF (100 µL) and the mixture stirred at room temperature for 1.5 hours. The solvent was evaporated in vacuo and the residue dissolved in DCM (10 mL). The solvent was evaporated in vacuo. DCM (2 mL), anhydrous pyridine (100 µL, 0.120 mmol) and TEA (90 µL, 0.650 mmol) were added and the solution added to the reaction mixture drop-wise. The reaction mixture was stirred at reflux for 6 hours. The mixture was diluted with DCM (10 mL) and the solution washed with sat. NaHCO$_{3(aq)}$ (20 mL), dried (MgSO$_4$), filtered and the solvent evaporated in vacuo. The crude product was purified by flash chromatography eluting with isohexane→3:1 isohexane-acetone (1% TEA) to yield (2R,3R,4R,5R,8R,10R,11R,12S,13S,14R)-11-(((2S,3R,4S,6R)-3-acetoxy-4-(dimethylamino)-6-methyltetrahydro-2H-pyran-2-yl)oxy)-2-ethyl-3,10-dihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-4-yl 2-(benzyloxy)acetate (47 mg, 20%) as a pale yellow solid. LCMS (Method D): Rt=2.18 mins; [M+H]+=939.9.

Step 3: (2R,3R,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,10-dihydroxy-3-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-4-yl 2-(benzyloxy)acetate (2R,3R,4R,5R,8R,10R,11R,12S,13S,14R)-11-(((2S,3R,4S,6R)-3-Acetoxy-4-(dimethylamino)-6-methyltetrahydro-2H-pyran-2-yl)oxy)-2-ethyl-3,10-dihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-4-yl 2-(benzyloxy)acetate (36 mg, 0.0400 mmol) was dissolved in MeOH (5 mL) and the mixture stirred at 60° C. for 5 hours. The solvent was evaporated in vacuo and the crude product purified by flash chromatography (Biotage SP1; 10 g SNAP cartridge) eluting with isohexane→3:1 isohexane-acetone (1% TEA) to yield (2R,3R,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,10-dihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-4-yl 2-(benzyloxy)acetate (17 mg, 49%) as a pale yellow gum. LCMS (Method D): Rt=2.13 mins; [M+H]+=897.9

Step 4: (2R,3R,4R,5R,8R,10R,11R,12S,13S,14R)-11-(((2S,3R,4S,6R)-4-(Dimethylamino)-3-hydroxy-6-methyltetrahydro-2H-pyran-2-yl)oxy)-2-ethyl-3,10-dihydroxy-3-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-4-yl 2-hydroxyacetate

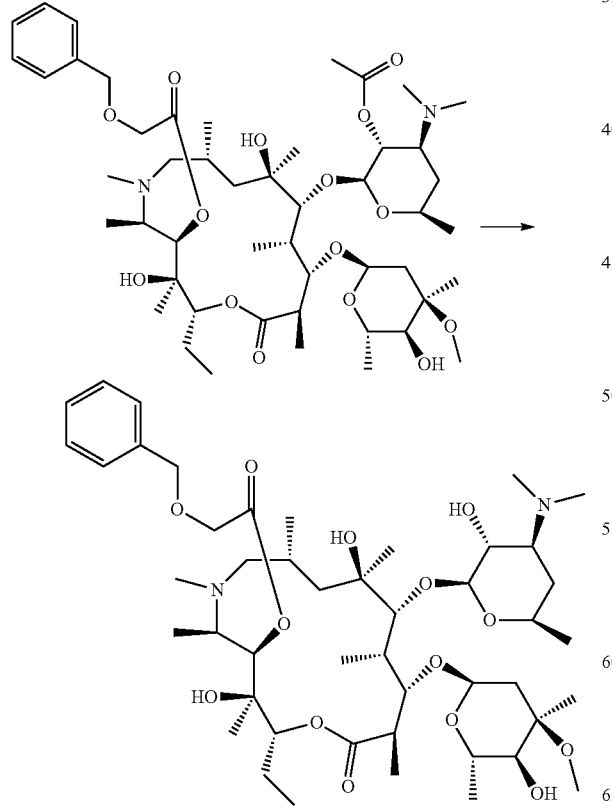

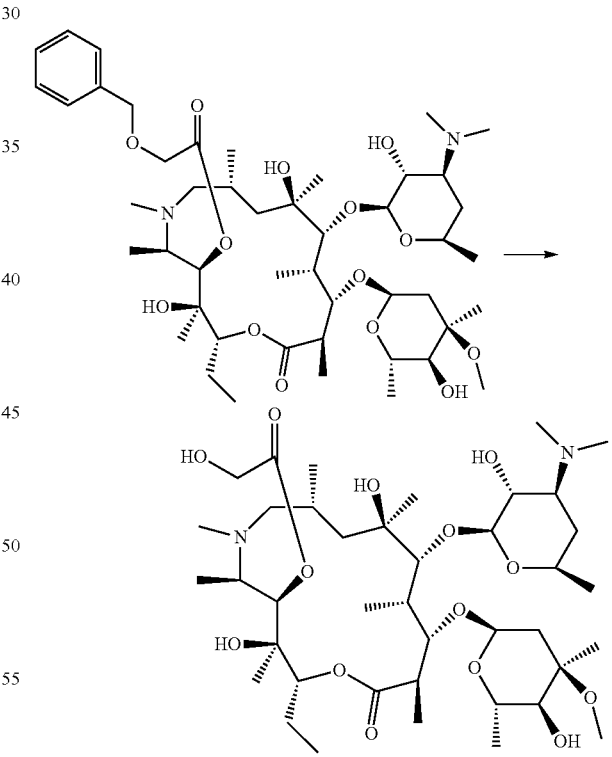

(2R,3R,4R,5R,8R,10R,11R,12S,13S,14R)-11-(((2S,3R,4S,6R)-4-(Dimethylamino)-3-hydroxy-6-methyltetrahydro-2H-pyran-2-yl)oxy)-2-ethyl-3,10-dihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-4-yl 2-(benzyloxy)acetate (15 mg, 0.0200 mmol) was dissolved in EtOAc (5 mL). Palladium 10% wt on carbon (9.00 mg, 0.0100 mmol) was added and the mixture stirred at 70° C. for 1 minute. Ammonium formate (15.0 mg, 0.240 mmol) was added in one portion and the mixture stirred at 70° C. for 16 hours. Palladium 10% wt on carbon (18 mg, 0.169 mmol) and ammonium formate (50 mg, 0.786 mmol) were added and the mixture stirred at 70° C. for 98 hours. The mixture was filtered through celite, washing with EtOAc (50 mL). The filtrate was washed successively with sat. $NaHCO_{3(aq)}$ (20 mL) and sat. brine solution (20 mL). The organic phase was dried ($MgSO_4$), filtered and the solvent evaporated in vacuo to yield (2R,3R,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,10-dihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-4-yl 2-hydroxyacetate (10.0 mg, 74%) as a white solid. LCMS (Method D): Rt=1.69 mins; [M+H]+=807.8.

Chemical Synthesis Example 12

Step 1: (2S,3R,4S,6R)-2-(((2R,3R,4R,5R,8R,10R,11R,12S,13S,14R)-4-Acetoxy-2-ethyl-3,10-dihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-1-yl)oxy)-4-(dimethylamino)-6-methyltetrahydro-2H-pyran-3-yl acetate

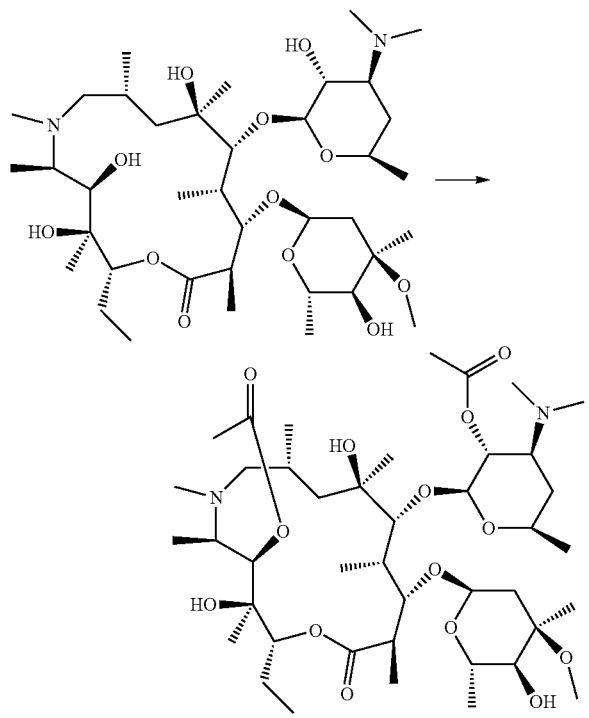

Azithromycin dihydrate (300 mg, 0.382 mmol) was dissolved in anhydrous DCM (10 mL). Acetic anhydride (90 μL, 0.952 mmol) and pyridine (90 μL, 1.11 mmol) were added and the mixture stirred at 40° C. for 108 hours. The mixture was diluted with DCM (40 mL) and the solution washed successively with sat. $NH_4Cl_{(aq)}$ (3×25 mL), water (25 mL) and sat. brine solution (25 mL). The organic phase was dried ($MgSO_4$), filtered and the solvent evaporated in vacuo to yield (2S,3R,4S,6R)-2-(((2R,3R,4R,5R,8R,10R,11R,12S,13S,14R)-4-acetoxy-2-ethyl-3,10-dihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-4-(dimethylamino)-6-methyltetrahydro-2H-pyran-3-yl acetate (201 mg, 63%) as a colourless gum. LCMS (Method D): Rt=1.86 mins; [M+H]+=833.8.

Step 2: (2R,3R,4R,5R,8R,10R,11R,12S,13S,14R)-11-(((2S,3R,4S,6R)-4-(Dimethylamino)-3-hydroxy-6-methyltetrahydro-2H-pyran-2-yl)oxy)-2-ethyl-3,10-dihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-4-yl acetate

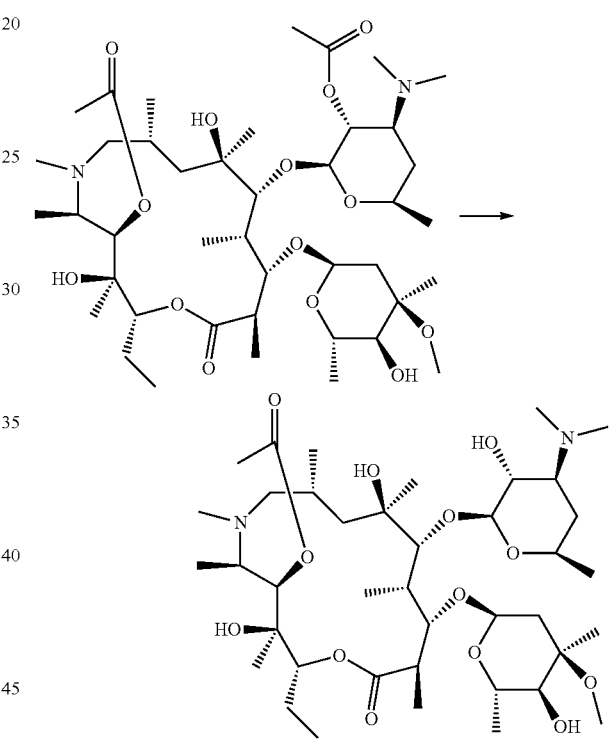

(2S,3R,4S,6R)-2-(((2R,3R,4R,5R,8R,10R,11R,12S,13S,14R)-4-Acetoxy-2-ethyl-3,10-dihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-4-(dimethylamino)-6-methyltetrahydro-2H-pyran-3-yl acetate (201 mg, 0.241 mmol) was dissolved in anhydrous MeOH (10 mL) and the mixture stirred at 50° C. for 4 hours. The solvent was evaporated in vacuo. The crude product was purified by flash chromatography eluting with isohexane→3:1 isohexane-acetone (1% TEA). The crude product was re-purified by flash chromatography eluting with isohexane→3:1 isohexane-acetone (1% TEA) to yield (2R,3R,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,10-dihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-4-yl acetate (25 mg, 13%) as a colourless gum which solidified to a white solid upon scratching. LCMS (Method D): Rt=1.77 mins; [M+H]+=791.9.

Chemical Synthesis Example 13

Step 1: (2S,3R,4S,6R)-4-(Dimethylamino)-2-(((3aR, 4R,7R,8S,9S,10R,11R,13R,16R,16aS)-4-ethyl-11-hydroxy-8-(((2R,4R,5S,6S)-5-hydroxy-4-methoxy-4, 6-dimethyltetrahydro-2H-pyran-2-yl)oxy)-2-isopropyl-3a, 7,9,11,13,15,16-heptamethyl-6-oxotetradecahydro-[1,3,2]dioxazolo[4,5-c][1]oxa[6] azacyclopentadecin-10-yl)oxy)-6-methyltetrahydro-2H-pyran-3-yl acetate Step 2: (2S,3S,4R,6R)-6-(((3aR,4R,7R,8S,9S,10R, 11R,13R,16R,16aS)-10-(((2S,3R,4S,6R)-3-Acetoxy-4-(dimethylamino)-6-methyltetrahydro-2H-pyran-2-yl)oxy)-4-ethyl-11-hydroxy-2-isopropyl-3a,7,9,11, 13,15,16-heptamethyl-6-oxotetradecahydro-[1,3,2] dioxazolo[4,5-c][1]oxa[6]azacyclopentadecin-8-yl) oxy)-4-methoxy-2,4-dimethyltetrahydro-2H-pyran-3-yl acetate

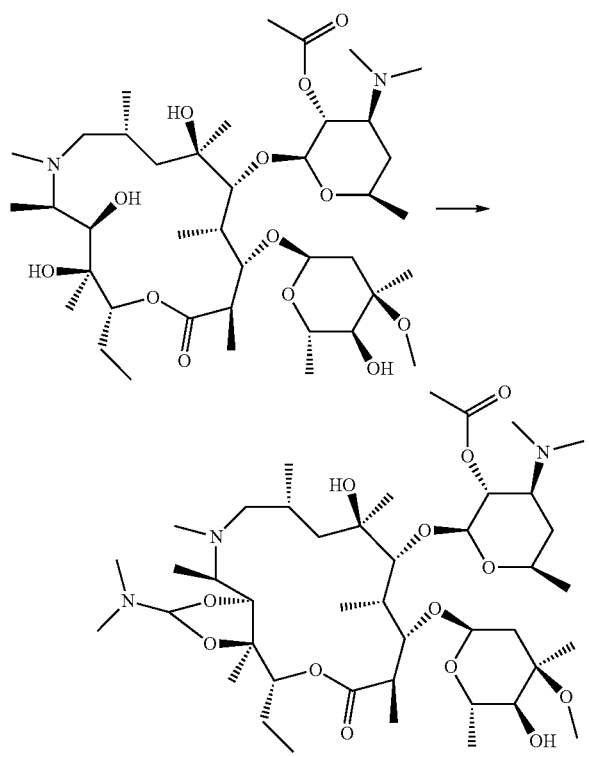

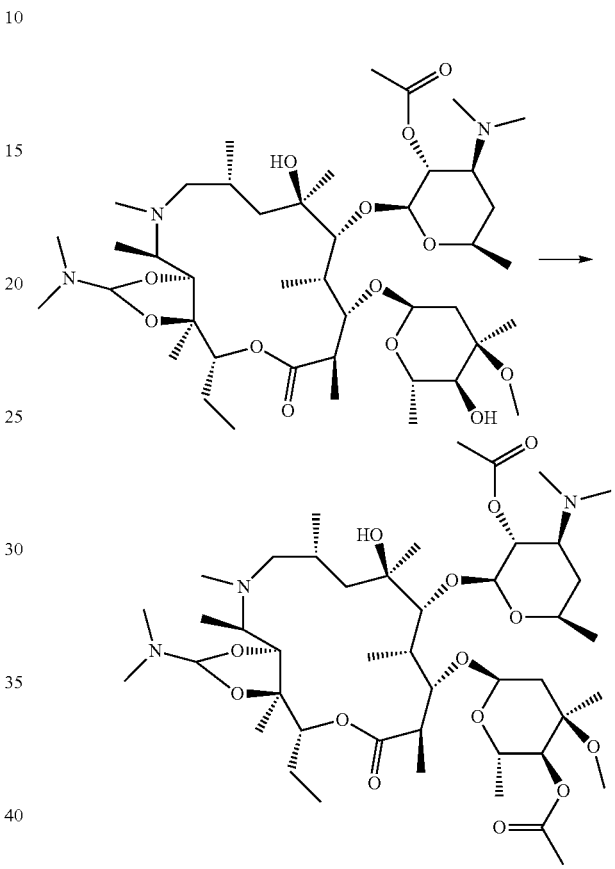

(2S,3R,4S,6R)-4-(Dimethylamino)-2-(((2R,3S,4R,5R, 8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl (R)-2-acetoxypropanoate (500 mg, 0.632 mmol) was dissolved in chloroform (5 mL). N,N-Dimethylformamide dimethyl acetal (600 µL, 4.52 mmol) was added and the mixture stirred at 55° C. for 16 hours. The solvent was evaporated in vacuo. The crude product was purified by flash chromatography (Biotage SP1; 10 g SNAP cartridge) eluting with isohexane→7:1 isohexane-acetone (1% TEA) to yield (2S,3R,4S,6R)-4-(dimethylamino)-2-(((3aR,4R,7R,8S,9S,10R,11R,13R,16R, 16aS)-4-ethyl-11-hydroxy-8-(((2R,4R,5S,6S)-5-hydroxy-4-methoxy-4,6-dimethyltetrahydro-2H-pyran-2-yl)oxy)-2-isopropyl-3a,7,9,11,13,15,16-heptamethyl-6-oxotetradecahydro-[1,3,2]dioxazolo[4,5-c][1]oxa[6] azacyclopentadecin-10-yl)oxy)-6-methyltetrahydro-2H-pyran-3-yl acetate (421 mg, 79%) as a white solid. LCMS (Method D): Rt=2.03 mins; [M+H]+=846.8.

(2S,3R,4S,6R)-4-(Dimethylamino)-2-(((3 aR,4R,7R,8S, 9S,10R,11R,13R,16R,16aS)-4-ethyl-11-hydroxy-8-(((2R, 4R,5S,6S)-5-hydroxy-4-methoxy-4,6-dimethyltetrahydro-2H-pyran-2-yl)oxy)-2-isopropyl-3a,7,9,11,13,15,16-heptamethyl-6-oxotetradecahydro-[1,3,2]dioxazolo[4,5-c] [1]oxa[6]azacyclopentadecin-10-yl)oxy)-6-methyltetrahydro-2H-pyran-3-yl acetate (150 mg, 0.177 mmol) and 4-(dimethylamino)pyridine (5.0 mg, 0.0409 mmol) were dissolved in anhydrous DCM (10 mL). TEA (150 µL, 1.08 mmol) and acetic anhydride (100 µL, 1.06 mmol) were added and the mixture stirred at r.t. for 48 hours. The mixture was diluted with DCM (40 mL) and the solution washed successively with sat. NH$_4$Cl$_{(aq)}$ (3×25 mL), water (2×25 mL) and sat. brine solution (25 mL). The organic phase was dried (MgSO$_4$), filtered & the solvent evaporated in vacuo. (2S,3S,4R,6R)-6-(((3aR,4R,7R,8S,9S,10R,11R, 13R,16R,16aS)-10-(((2S,3R,4S,6R)-3-Acetoxy-4-(dimethylamino)-6-methyltetrahydro-2H-pyran-2-yl)oxy)-4-ethyl-11-hydroxy-2-isopropyl-3a,7,9,11,13,15,16-heptamethyl-6-oxotetradecahydro-[1,3,2]dioxazolo[4,5-c][1]oxa[6] azacyclopentadecin-8-yl)oxy)-4-methoxy-2,4-dimethyltetrahydro-2H-pyran-3-yl acetate (129 mg, 82%) was obtained as a white solid. LCMS (Method D): Rt=2.10 mins; [M+H]+=888.9

Step 3: (2S,3S,4R,6R)-6-(((2R,3S,4R,5R,8R,10R,11R,12S,13S,14R)-11-(((2S,3R,4S,6R)-4-(Dimethylamino)-3-hydroxy-6-methyltetrahydro-2H-pyran-2-yl)oxy)-2-ethyl-3,4,10-trihydroxy-3,5,6,8,10,12,14-heptamethyl-15-oxo-1-oxa-6-azacyclopentadecan-13-yl)oxy)-4-methoxy-2,4-dimethyltetrahydro-2H-pyran-3-yl acetate

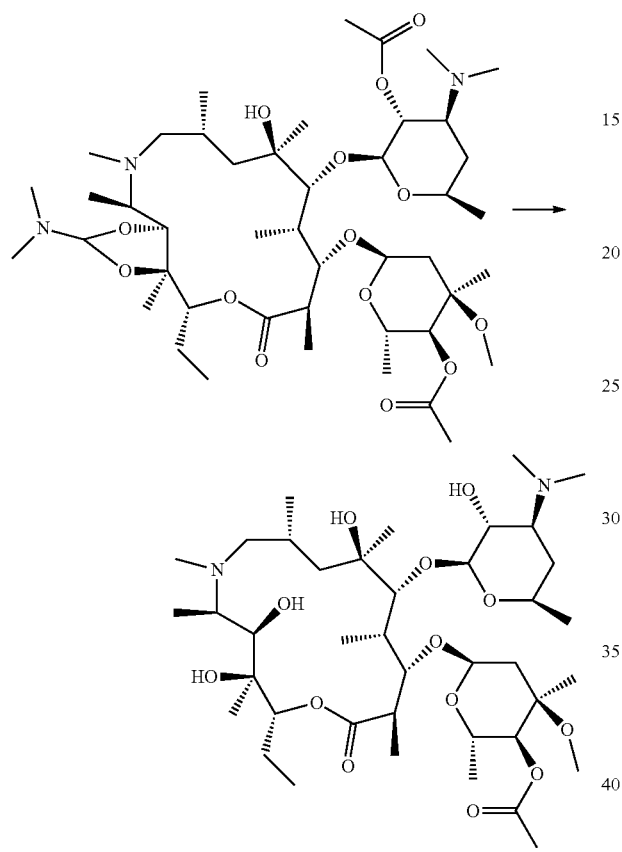

(2S,3S,4R,6R)-6-(((3aR,4R,7R,8S,9S,10R,11R,13R,16R,16aS)-10-(((2S,3R,4S,6R)-3-Acetoxy-4-(dimethylamino)-6-methyltetrahydro-2H-pyran-2-yl)oxy)-4-ethyl-11-hydroxy-2-isopropyl-3a,7,9,11,13,15,16-heptamethyl-6-oxotetradecahydro-[1,3,2]dioxazolo[4,5-c][1]oxa[6]azacyclopentadecin-8-yl)oxy)-4-methoxy-2,4-dimethyltetrahydro-2H-pyran-3-yl acetate (129 mg, 0.145 mmol) was dissolved in anhydrous MeOH (5 mL). Formic acid (50 µL, 1.33 mmol) was added and the mixture stirred at 55° C. for 16 hours. The mixture was diluted with DCM (40 mL) and the solution washed successively with sat. NH₄Cl(aq) (3×25 mL), water (2×25 mL) and sat. brine solution (25 mL). The organic phase was dried (MgSO₄), filtered & the solvent evaporated in vacuo. The crude product was purified by flash chromatography (Biotage SP1; 10 g SNAP cartridge) eluting with isohexane→3:1 isohexane-acetone (1% TEA) to yield (2S,3S,4R,6R)-6-(((2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-3,5,6,8,10,12,14-heptamethyl-15-oxo-1-oxa-6-azacyclopentadecan-13-yl)oxy)-4-methoxy-2,4-dimethyltetrahydro-2H-pyran-3-yl acetate (58 mg, 51%) as a colourless gum which solidifies to a white solid upon scratching. LCMS (Method D): Rt=1.76 mins; [M+H]+=791.8

Chemical Synthesis Example 14

Step 1. Methyl N-acetyl-S-((((2S,3R,4S,6R)-4-(dimethylamino)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)carbonyl)-L-cysteinate

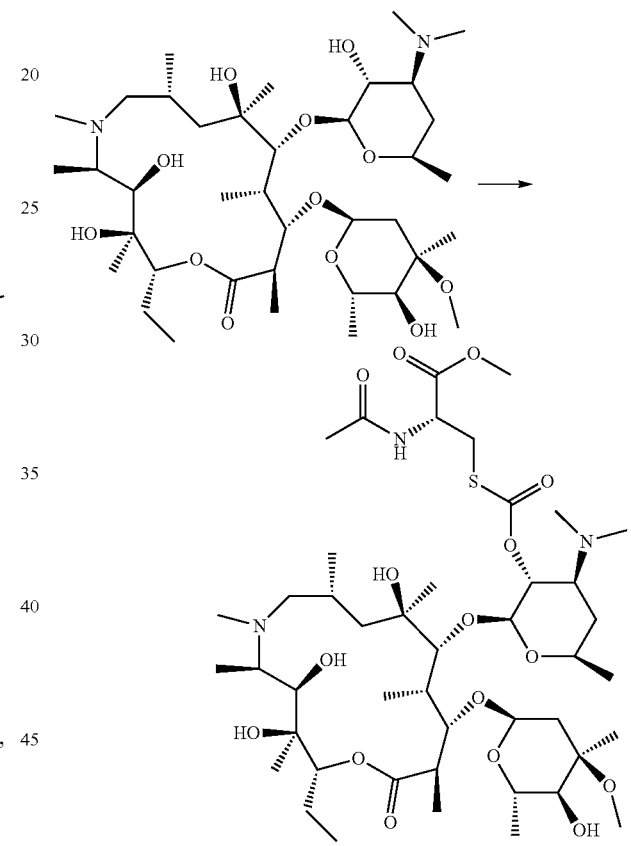

Azithromycin dihydrate (100 mg, 0.127 mmol) was dissolved in anhydrous DCM (5 mL). MgSO₄ was added and the mixture stirred for 1 minute. The solution was then filtered. To the filtrate was added TEA (100 µL, 0.717 mmol) and triphosgene (23 mg, 0.0775 mmol) and the mixture stirred at r.t. for 1 hour. N-Acetyl-L-cysteine methyl ester (45 mg, 0.254 mmol) was added and the mixture stirred at r.t. for 30 minutes. Triphosgene (23 mg, 0.0775 mmol) was added and the mixture stirred at r.t. for 16.5 hours. The mixture was diluted with DCM (40 mL) and the solution washed successively with sat. NaHCO₃(aq) (20 mL) and sat. brine solution (20 mL). The organic phase was dried (MgSO₄), filtered and the solvent evaporated in vacuo. The crude product was purified by flash chromatography (Biotage SP1; 10 g SNAP cartridge) eluting with isohexane→3:1 isohexane-acetone (1% TEA) to yield methyl N-acetyl-S-((((2S,3R,4S,6R)-4-(dimethylamino)-2-(((2R, 3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-6-methyltetrahydro-2H-pyran-3-yl)oxy)carbonyl)-L-cysteinate (49 mg, 40%) as a colourless gum. LCMS (Method D): Rt=1.83 mins; [M+H]+=952.8

II. Biological Evaluation

Example 1: Rabbit Cornea Homogenate Stability Assay

Determining Rabbit Cornea Homogenate stability of the test compounds was performed using HPLC-MS. The assay was performed at two concentrations of Rabbit Cornea Homogenate (0.15 mg/ml and 0.45 mg/ml total protein) so that any hydrolysis observed could be assigned as esterase dependent or not.

Rabbit Cornea Homogenisation

Five rabbit corneas (e.g. New Zealand Whites) of approx. 50 mg each were sliced and scraped with a scalpel and tweezers until reduced to small (1-3 mm), thin pieces. These were transferred into a tared vial and accurately weighed, then diluted with 10 volumes aqueous PBS pH7.4

Sample was cooled intermittently on ice and shear homogenized for 3 minutes, then centrifuged for 3 min at 3000 rpm. The supernatant was pipetted off into a vial, and total protein concentration determined at 280 nm. Sample was stored at −78° C.

Rabbit Cornea Esterase Assay
Preparation of Stock Solutions:

10 mM Compound stocks were diluted to 100 μM in a 96 deep-well plate: 10 μl of 10 mM Compound stock was added to 990 μl 50 mM HEPES, pH7.5 buffer.

Compounds were further diluted to 10 μM: 100 μl of 100 μM compound was added to 900 μl 50 mM HEPES, pH7.5 buffer.

Esterase homogenate was diluted to 300 ng/μl and 900 ng/μl
Assay Conditions:

A heater shaker was set to 37° C. Into a suitable 96 well plate (Run Plate), 75 μl of 300 or 900 ng/μl esterase homogenate was pipetted into each of the required wells (2 min, 5 min, 10 min, 20 min and 45 min). The plate was sealed and then warmed at 37° C. for 5 min.

Another 96 well PCR plate was put on ice (Kill Plate). To this was added 100 μl of MeCN to each well, labelled 0 min 2 min, 5 min, 10 min, 20 min and 45 min. The plate was covered to minimise evaporation.

For the T=0 sample only, to the 100 μl cold MeCN stop solution was added 50 μl of 300 or 900 ng/μl esterase homogenate followed by 50 μl of 10 μM compound solution For the remaining timepoints, 75 μl of 10 μM compound solution was added to the Run Plate starting from T=45 min row and ending with T=2 min row.

At the appropriate time point, 100 μl of the assay mixture was added to the matching kill plate well containing 100 μl of cold MeCN.

Samples were analysed as soon as practicable by LCMS (Waters Xevo TQ-S or Micromass Ultima).

Parent conjugate and parent concentrations were determined against appropriate standard response curves and the half-life ($T_{1/2}$) of the parent conjugate was calculated using the peak area of the parent conjugate at each time point in the linear region of the log-linear plot.

Hydrolysis Rates of Example Compounds

TABLE 3

| Compound | $T_{1/2}$ Esterase (min) (0.15 mg/ml Homogenate) | $T_{1/2}$ Esterase (min) (0.45 mg/ml Homogenate) | $T_{1/2}$ Aq Stability (min) |
| --- | --- | --- | --- |
| 1 | Could not be determined due to rapid hydrolysis | Could not be determined due to rapid hydrolysis | ND, estimated <3 in HEPES pH 7.5 |
| 2 | Could not be determined due to rapid hydrolysis | Could not be determined due to rapid hydrolysis | <3 HEPES pH 7.5 |
| 3 | 35 Not Esterase dependant | 39 Not Esterase dependant | 42 HEPES pH 7.5 |
| 4 | Could not be determined due to rapid hydrolysis | Could not be determined due to rapid hydrolysis | 5.7 HEPES pH 7.5 |
| 5 | 21 Not Esterase dependant | 24 Not Esterase dependant | 72 HEPES pH 7.5 |
| 6 | Could not be determined due to rapid hydrolysis | Could not be determined due to rapid hydrolysis | ND, estimated <3 in HEPES pH 7.5 |
| 7 | Could not be determined due to rapid hydrolysis | Could not be determined due to rapid hydrolysis | ND, estimated <3 in HEPES pH 7.5 |
| 8 | Could not be determined due to rapid hydrolysis | Could not be determined due to rapid hydrolysis | ND, estimated <3 in HEPES pH 7.5 |
| 9 | Could not be determined due to rapid hydrolysis | Could not be determined due to rapid hydrolysis | ND, estimated <3 in HEPES pH 7.5 |
| 10 | 53 Not Esterase dependant | 49 Not Esterase dependant | ND, estimated as ca. 51 from esterase assay |
| 11 | >120 | >120 | >120 HEPES pH 7.5 |
| 12 | >120 | >120 | >120 HEPES pH 7.5 |
| 13 | >120 | >120 | >120 HEPES pH 7.5 |
| 14 | >120 | >120 | >120 HEPES pH 7.5 |

Example 2: Aqueous Hydrolysis Stability Assay

Determination of aqueous stability of the test compounds was performed using HPLC-MS. A test compound 10 mM stock solution was prepared in DMSO. 10 μl of the DMSO stock solution was dissolved in 990 μl of 50 mM HEPES pH 7.5 buffer or 1:1 (v/v) of Acetonitrile:Water to make a 100 μM solution. Final DMSO concentration was 1%. The solution was kept at room temperature and injected without delay into the LCMS (Waters Xevo TQ-S or Micromass Ultima). Additional injections were performed at appropriate time points. Half-life ($T_{1/2}$) of the parent conjugate was calculated using the peak area of the parent conjugate at each time point in the linear region of the log-linear plot.

Example 3: Mouse Model of Experimental Dry Eye Disease

Female C57BL/6 mice (6-8 weeks old) or female HEL BCR Tg mice (6-8 weeks old) are commercially obtained. Experimental dry eye is induced as described by Niederkorn, et al. (J. Immunol. 2006, 176:3950-3957) and Dursun et al. (Invest. Ophthalmol. Vis. Sci. 2002, 43:632-638). In brief, mice are exposed to desiccating stress in perforated cages with constant airflow from fans positioned on both sides and room humidity maintained at 30% to 35%. Injection of scopolamine hydrobromide (0.5 mg/0.2 mL; Sigma- Aldrich, St. Louis, Mo.) is administered subcutaneously, three times a day (8:00 AM, 12:00 noon, and 5:00 PM), on alternating hind-flanks to augment disease. Mice are exposed to desiccating stress for 3 weeks. Untreated control mice are maintained in a nonstressed environment at 50% to 75% relative humidity without exposure to forced air. Test animals are exposed to test compound and subsequently tear samples are obtained to determine stability of test compounds, and tissue samples are taken to determine presence of pro-inflammatory biomarkers.

II. Preparation of Pharmaceutical Dosage Forms

Example 1: Solution for Topical Ophthalmic Use

The active ingredient is a compound of Table 1, or a pharmaceutically acceptable salt thereof, and is formulated as a solution with a concentration of between 0.1-1.5% w/v.

We claim:

1. An ophthalmic pharmaceutical composition comprising a compound having a structure represented by Formula (Ia):

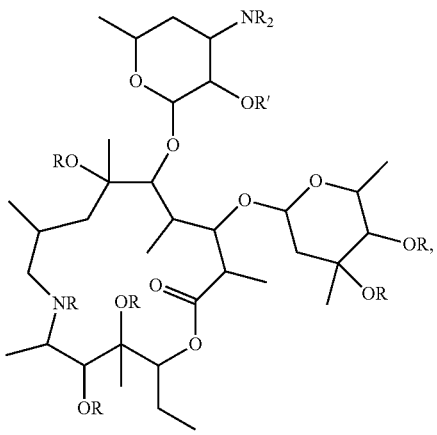

Formula (Ia)

wherein,
each R is independently H, substituted or unsubstituted alkyl, or substituted or unsubstituted heteroalkyl;
R' is D-L-;
D is a radical of a keratolytic agent;
L is a linker,
wherein R' is not —(C=O)-unsubstituted alkyl;
or a pharmaceutically acceptable salt or solvate thereof,
the ophthalmic pharmaceutical composition being suitable for administration on or around the surface of the eye.

2. The ophthalmic pharmaceutical composition of claim 1, wherein the compound has a structure represented by the following formula:

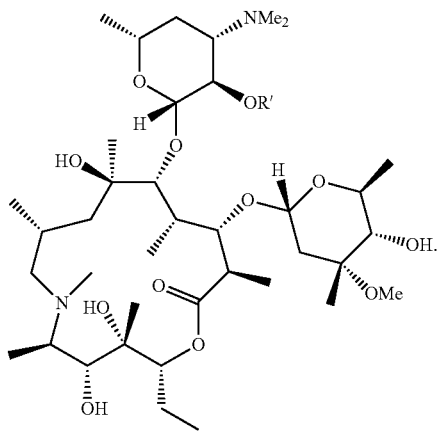

3. The ophthalmic pharmaceutical composition of claim 1, wherein L comprises one or more linker group, each linker group being independently selected from the group consisting of a bond, —O—, alkyl (alkylenyl), heteroalkyl (heteroalkylenyl), ester, and carbonyl (>C=O).

4. The ophthalmic pharmaceutical composition of claim 1, wherein L is a bond.

5. The ophthalmic pharmaceutical composition of claim 1, wherein R' is alkyl or heteroalkyl substituted with at least one oxo, and further optionally substituted.

6. The ophthalmic pharmaceutical composition of claim 1, wherein R' is:

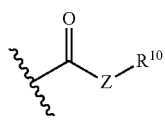

wherein:
Z is —$(CR^8R^9)_m$—;
m is 1-6;
$R^8$ and $R^9$ are each independently H, halo, alkoxy, alkyl, or haloalkyl; and
$R^{10}$ is —OH, —O(C=O)alkyl, substituted alkyl, alkoxy, heterocyclyl, or aryl, wherein alkoxy, heterocyclyl, and aryl is optionally substituted.

7. The ophthalmic pharmaceutical composition of claim 6, wherein $R^8$ and $R^9$ are each independently H or $C_1$-$C_6$ alkyl.

8. The ophthalmic pharmaceutical composition of claim 6, wherein m is 1-4.

9. The ophthalmic pharmaceutical composition of claim 6, wherein:
Z is —$(CR^8R^9)_m$—;
m is 1-4;
$R^8$ and $R^9$ are each independently H or alkyl; and
$R^{10}$ is optionally substituted heterocyclyl.

10. The ophthalmic pharmaceutical composition of claim 6, wherein:
  Z is —CH₂— or —CH(CH₃)—; and
  R¹⁰ is —OH, alkoxy, or aryl, the alkoxy and aryl being optionally substituted.

11. The ophthalmic pharmaceutical composition of claim 6, wherein R¹⁰ is —O(C=O)alkyl, wherein the —O(C=O)alkyl is substituted with one or more substituent, each substituent being independently selected from the group consisting of oxo, —SH, and —NHCOCH₃.

12. The ophthalmic pharmaceutical composition of claim 6, wherein R¹⁰ is —OH, —(OCH₂CH₂)₄OH, —CH₂(OCH₂CH₂)₄OH, —(C=O)CH₃,

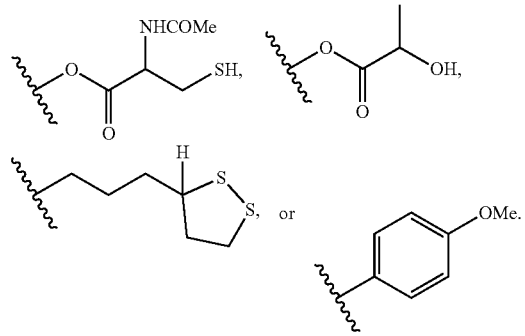

13. The ophthalmic pharmaceutical composition of claim 1, wherein R' is:

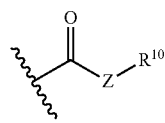

wherein:
  Z is O; and
  R¹⁰ is alkyl, the alkyl being substituted with heteroalkyl.

14. The ophthalmic pharmaceutical composition of claim 1, wherein R' is:

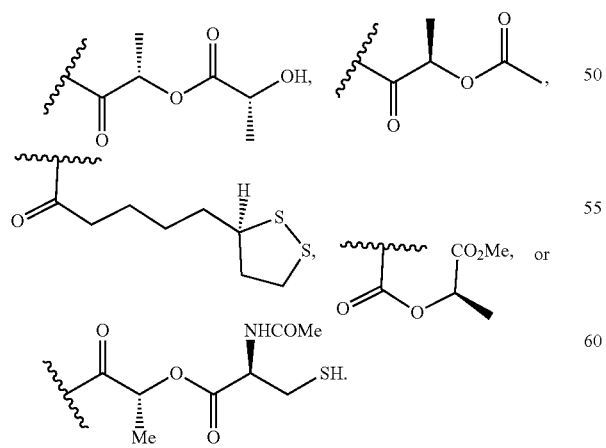

15. The ophthalmic pharmaceutical composition of claim 1, wherein the compound has the structure:

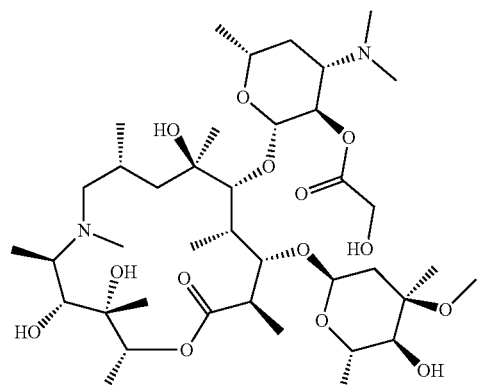

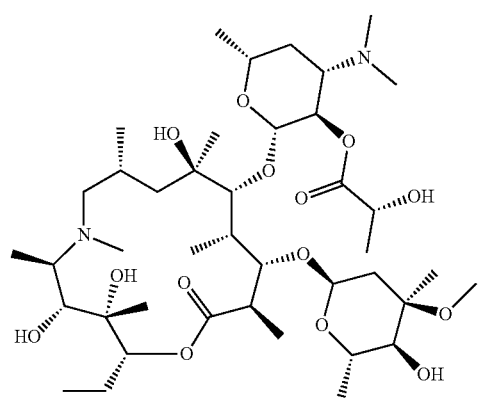

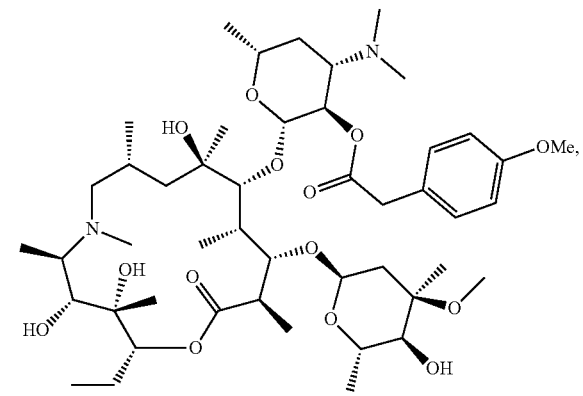

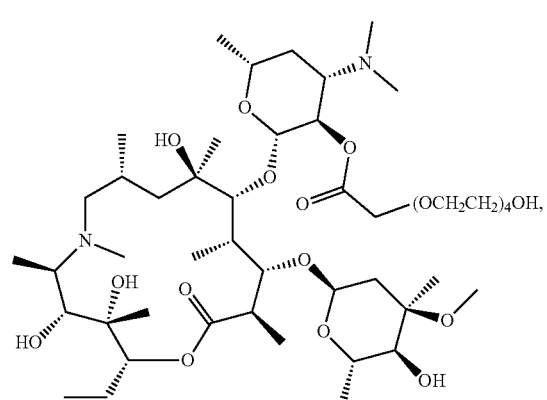

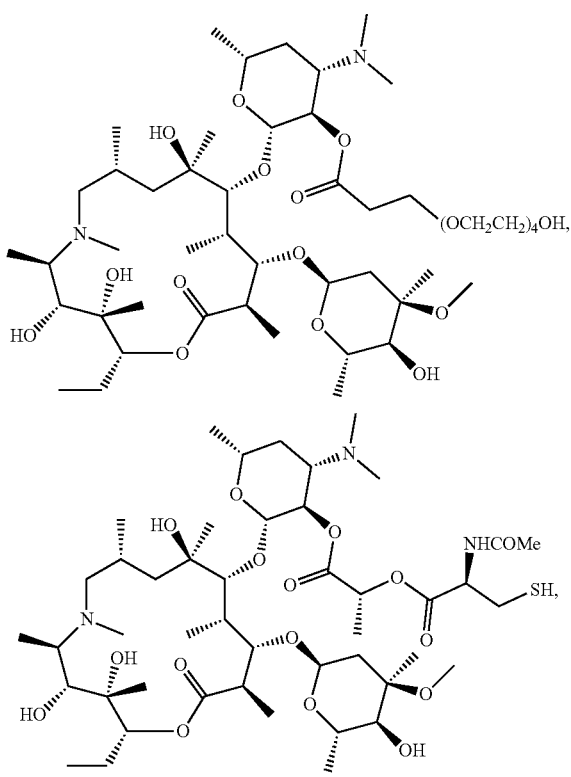
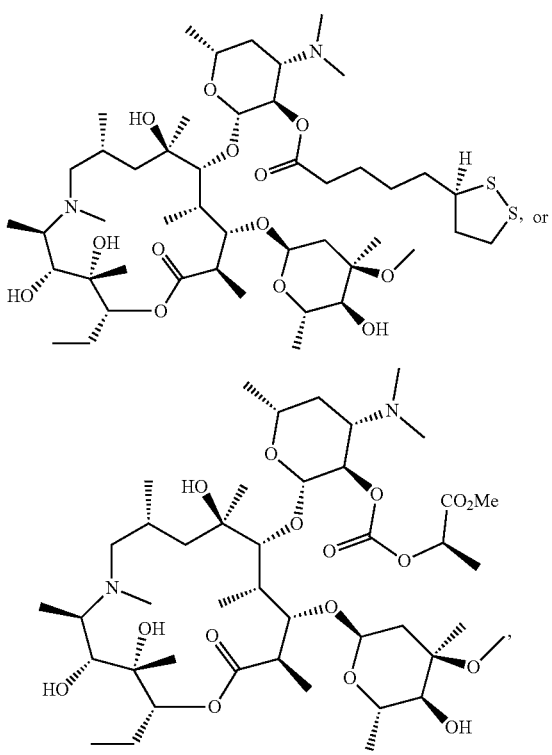
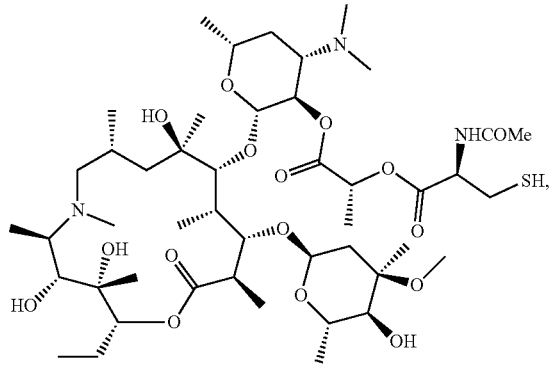
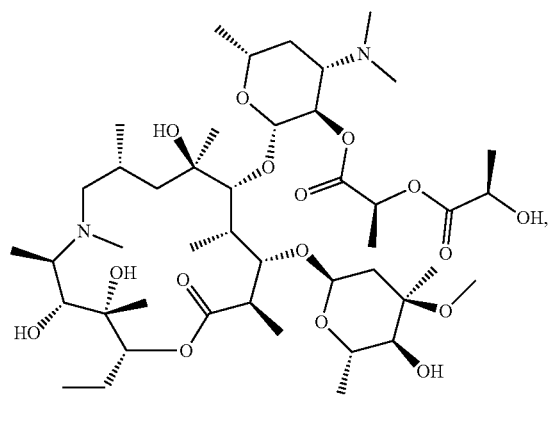
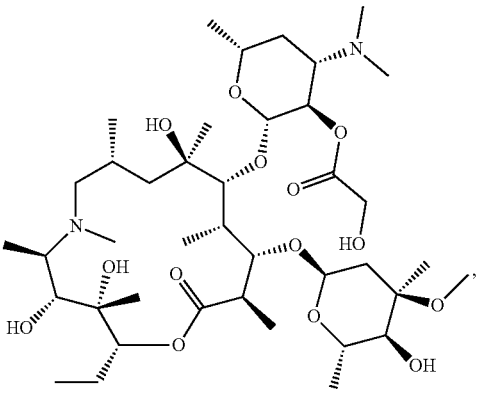
or a pharmaceutically acceptable salt or solvate thereof.
16. A compound having the structure:
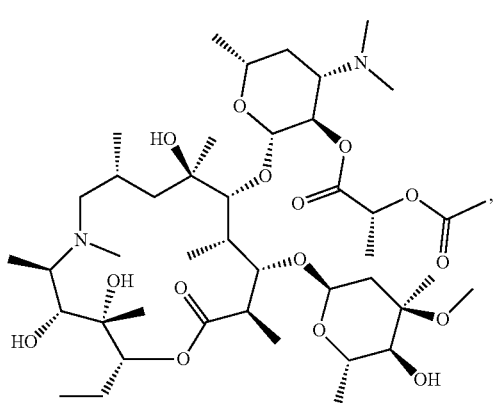
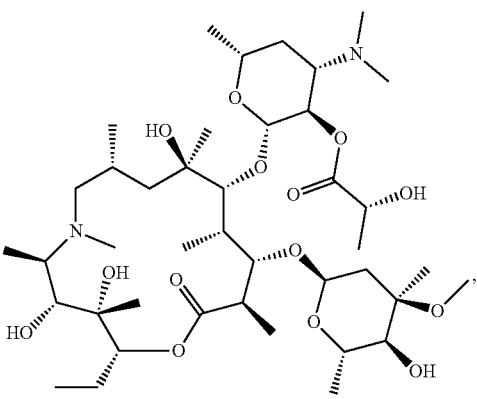

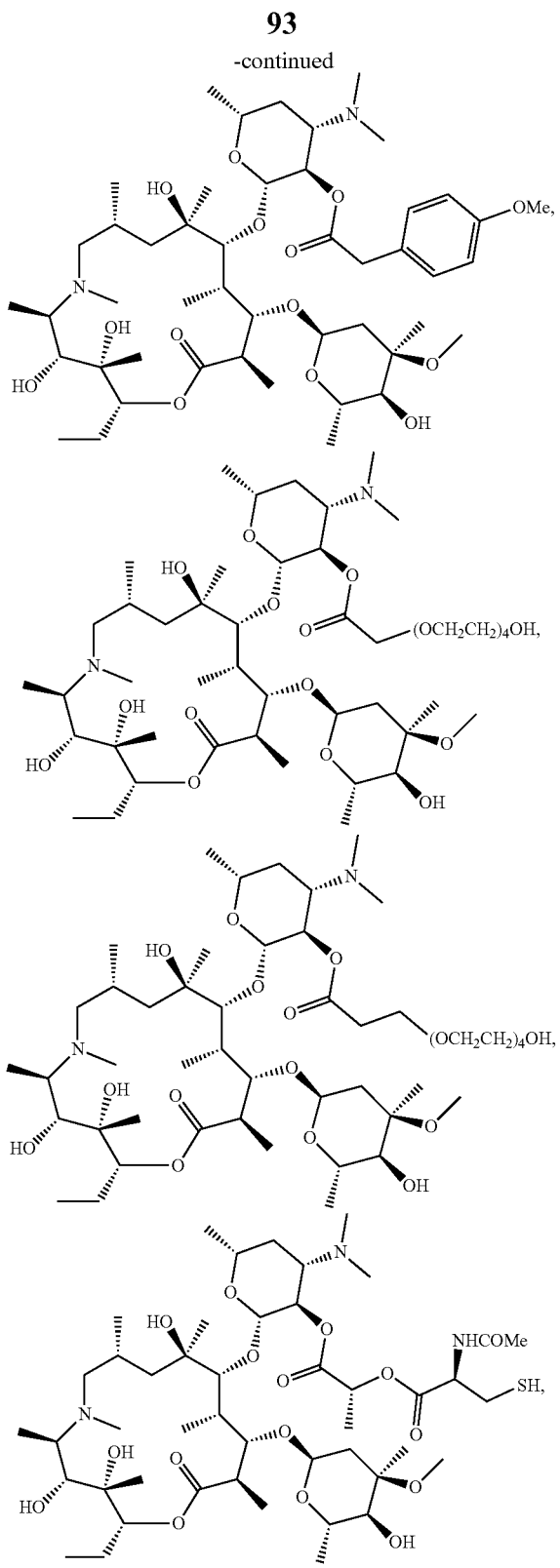

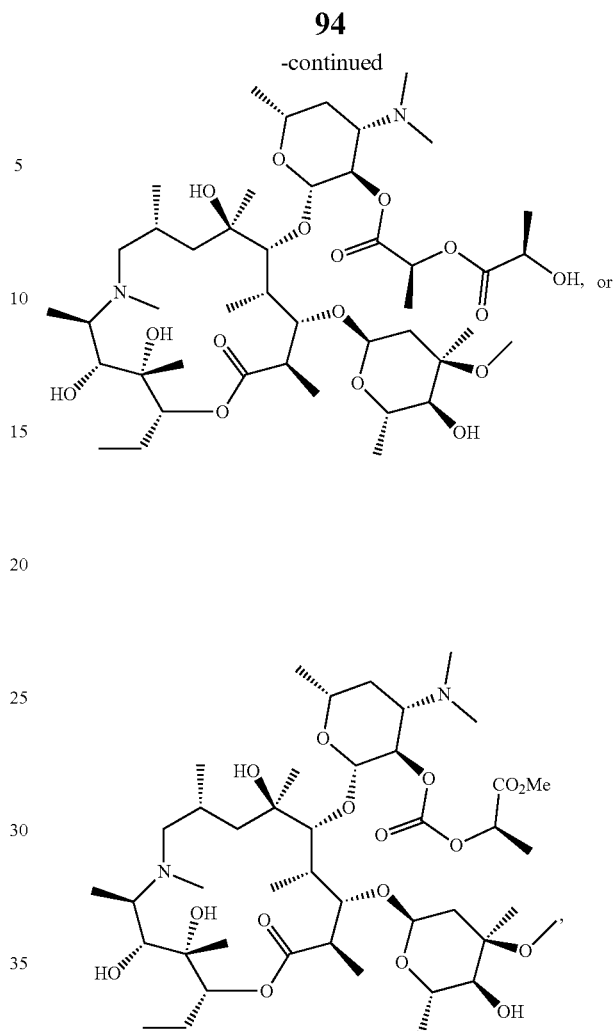

or a pharmaceutically acceptable salt or solvate thereof.

17. The ophthalmic pharmaceutical composition of claim 1, wherein the ophthalmic pharmaceutical composition is suitable for periocular administration.

18. A method of treating an ocular disease or disorder in an individual, comprising providing on or around the surface of the eye of the individual a composition of claim 1.

19. The method of claim 18, wherein the ocular disease or disorder is associated with keratosis, microbial infiltration, microbial infection, inflammation, or any combination thereof.

20. The ophthalmic pharmaceutical composition of claim 1, wherein the linker is a hydrolyzable linker.

* * * * *